United States Patent
Ruoslahti et al.

(10) Patent No.: US 10,179,801 B2
(45) Date of Patent: Jan. 15, 2019

(54) TRUNCATED LYP-1 PEPTIDES AND METHODS AND COMPOSITIONS USING TRUNCATED LYP-1 PEPTIDES

(75) Inventors: Erkki Ruoslahti, Buellton, CA (US);
Tambet Teesalu, Goleta, CA (US);
Kazuki Sugahara, Goleta, CA (US);
Lise Roth, Strasbourg (FR)

(73) Assignee: SANFORD-BURNHAM MEDICAL RESEARCH INSTITUTE, La Jolla, CA (US)

( * ) Notice: Subject to any disclaimer, the term of this patent is extended or adjusted under 35 U.S.C. 154(b) by 1789 days.

(21) Appl. No.: 13/594,194

(22) Filed: Aug. 24, 2012

(65) Prior Publication Data

US 2015/0259380 A1    Sep. 17, 2015

Related U.S. Application Data

(60) Provisional application No. 61/527,789, filed on Aug. 26, 2011.

(51) Int. Cl.
| | |
|---|---|
| C07K 7/06 | (2006.01) |
| A61K 31/337 | (2006.01) |
| C07K 7/08 | (2006.01) |
| C07K 14/47 | (2006.01) |
| A61K 38/08 | (2006.01) |
| A61K 45/06 | (2006.01) |
| A61K 47/62 | (2017.01) |
| A61K 47/69 | (2017.01) |

(52) U.S. Cl.
CPC .............. *C07K 7/06* (2013.01); *A61K 31/337* (2013.01); *A61K 38/08* (2013.01); *A61K 45/06* (2013.01); *A61K 47/62* (2017.08); *A61K 47/6929* (2017.08); *A61K 47/6953* (2017.08); *C07K 7/08* (2013.01); *C07K 14/4748* (2013.01)

(58) Field of Classification Search
None
See application file for complete search history.

(56) References Cited

U.S. PATENT DOCUMENTS

| | | |
|---|---|---|
| 4,016,100 A | 4/1977 | Suzuki |
| 4,089,801 A | 5/1978 | Schneider |
| 4,235,871 A | 11/1980 | Papahadjopoulos |
| 4,745,160 A | 5/1988 | Churchill |
| 4,853,228 A | 8/1989 | Wallach |
| 5,013,497 A | 5/1991 | Yiournas |
| 5,410,016 A | 4/1995 | Hubbell |
| 5,412,072 A | 5/1995 | Sakurai |
| 5,449,513 A | 9/1995 | Yokoyama |
| 5,474,848 A | 12/1995 | Wallach |
| 5,534,499 A | 7/1996 | Ansell |
| 5,554,728 A | 9/1996 | Basava |
| 5,628,936 A | 5/1997 | Wallach |
| 5,653,996 A | 8/1997 | Hsu |
| 5,693,751 A | 12/1997 | Sakurai |
| 5,885,613 A | 3/1999 | Holland |
| 5,916,596 A | 6/1999 | Desai |
| 5,926,720 A | 7/1999 | Kataoka |
| 5,929,177 A | 7/1999 | Kataoka |
| 6,177,542 B1 | 1/2001 | Ruoslahti |
| 6,420,339 B1 | 7/2002 | Gregg |
| 6,506,405 B1 | 1/2003 | Desai |
| 6,530,944 B2 | 3/2003 | West |
| 6,537,579 B1 | 3/2003 | Desai |
| 6,552,170 B1 | 4/2003 | Thompson |
| 6,576,239 B1 | 6/2003 | Ruoslahti |
| 6,673,580 B2 | 1/2004 | Koren |
| 6,828,401 B2 | 12/2004 | Nho |
| 6,869,932 B2 | 3/2005 | Veronese |
| 7,544,767 B2 | 6/2009 | Ruoslahti |
| 2001/0021500 A1 | 9/2001 | Welch |
| 2002/0055174 A1 | 5/2002 | Rittner |
| 2002/0068272 A1 | 6/2002 | Larocca |
| 2002/0132990 A1 | 9/2002 | Huston |
| 2003/0003100 A1 | 1/2003 | Levy |
| 2003/0077289 A1 | 4/2003 | Wang |
| 2003/0082143 A1 | 5/2003 | Larocca |
| 2003/0082176 A1 | 5/2003 | LeBowitz |
| 2003/0083261 A1 | 5/2003 | Yu |
| 2003/0125283 A1 | 7/2003 | Gatenby |
| 2003/0148263 A1 | 8/2003 | Larocca |
| 2003/0166601 A1 | 9/2003 | Woodle |

(Continued)

FOREIGN PATENT DOCUMENTS

| | | |
|---|---|---|
| EP | 0045665 | 2/1982 |
| WO | 9632434 | 10/1996 |

(Continued)

OTHER PUBLICATIONS

Isidro-Llobet et al., "Amino Acid-Protecting Groups", Chem. Rev., 2009, p. 2455-2504 (Year: 2009).*
Laakkonen et al., "A tumor-homing peptide with a targeting specificity related to lymphatic vessels", Nature Med., 751-755, 2002 (Year: 2002).*
U.S. Appl. No. 08/996,883, filed Dec. 23, 1997, Ansell.
Acevedo, et al, "Semaphorin 3A suppresses VEGF-mediated angiogenesis yet acts as a vascular permeability factor" , Blood ,111:2674-80 (2008).
Agemy, et al., "Nanoparticle-induced vascular blockade in human prostate cancer" , Blood, 116(15):2847-56 (2010).
Agemy et al., "Targeted nanoparticle enhanced proapoptotic peptide as potential therapy for glioblastoma" , PNAS, 10817450-5 (2011).

(Continued)

*Primary Examiner* — Lianko G Garyu
(74) *Attorney, Agent, or Firm* — Pabst Patent Group LLP

(57) ABSTRACT

Disclosed are compositions and methods useful for targeting and internalizing molecules into cells of interest and for penetration by molecules of tissues of interest. The compositions and methods are based on peptide sequences, such as truncated LyP-1 peptides, that are selectively internalized by a cell, penetrate tissue, or both. The disclosed internalization and tissue penetration is useful for delivering therapeutic and detectable agents to cells and tissues of interest.

47 Claims, 7 Drawing Sheets

Specification includes a Sequence Listing.

(56) References Cited

U.S. PATENT DOCUMENTS

| | | |
|---|---|---|
| 2004/0005309 A1 | 1/2004 | LeBowitz |
| 2004/0219169 A1 | 11/2004 | Bermudes |
| 2005/0004002 A1 | 1/2005 | Desai |
| 2005/0038239 A1 | 2/2005 | Catchpole |
| 2005/0071088 A1 | 3/2005 | Landfield |
| 2005/0147993 A1 | 7/2005 | Khan |
| 2005/0233356 A1 | 10/2005 | Jones |
| 2005/0260756 A1 | 11/2005 | Troy |
| 2005/0281805 A1 | 12/2005 | LeBowitz |
| 2006/0014712 A1 | 1/2006 | Neuman |
| 2006/0051315 A1 | 3/2006 | Scaria |
| 2006/0070133 A1 | 3/2006 | Dean |
| 2006/0147922 A1 | 7/2006 | Watts |
| 2006/0147997 A1 | 7/2006 | Ramakrishnan |
| 2006/0154340 A1 | 7/2006 | Louie |
| 2006/0210526 A1 | 9/2006 | Brocchini |
| 2006/0233807 A1 | 10/2006 | Svanborg |
| 2006/0242725 A1 | 10/2006 | Strong |
| 2006/0257942 A1 | 11/2006 | Waldo |
| 2007/0111251 A1 | 5/2007 | Rosania |
| 2007/0111270 A1 | 5/2007 | Zhang |
| 2007/0157328 A1 | 7/2007 | Ramrakha |
| 2007/0212332 A1 | 9/2007 | Baylink |
| 2007/0231862 A1 | 10/2007 | Diamond |
| 2007/0287680 A1 | 12/2007 | Cuchelkar |
| 2007/0292920 A1 | 12/2007 | Lin |
| 2008/0234183 A1 | 9/2008 | Hallbrink |
| 2008/0305119 A1 | 12/2008 | Dewhurst |
| 2008/0311136 A1 | 12/2008 | Beusker |
| 2009/0031733 A1 | 2/2009 | Weaver |
| 2009/0087899 A1 | 4/2009 | McKnight |
| 2009/0176660 A1 | 7/2009 | Yla-Herttuala |
| 2009/0176710 A1 | 7/2009 | Hadwiger |
| 2009/0186802 A1 | 7/2009 | Alluis |
| 2009/0226372 A1 | 9/2009 | Ruoslahti |
| 2009/0246133 A1 | 10/2009 | Ruoslahti |
| 2009/0257951 A1 | 10/2009 | Ruoslahti |
| 2009/0258926 A1 | 10/2009 | Divita |
| 2009/0280058 A1 | 11/2009 | Troy |
| 2009/0305329 A1 | 12/2009 | Szilak |
| 2009/0317802 A1 | 12/2009 | Bhatia |
| 2009/0325866 A1 | 12/2009 | Kim |
| 2010/0016215 A1 | 1/2010 | Moulton |
| 2010/0022466 A1 | 1/2010 | Raucher |
| 2010/0048487 A1 | 2/2010 | Uno |
| 2010/0061932 A1 | 3/2010 | Brock |
| 2010/0061942 A1 | 3/2010 | Ma |
| 2010/0099627 A1 | 4/2010 | Seger |
| 2010/0143454 A1 | 6/2010 | McLinden |
| 2010/0322862 A1 | 12/2010 | Ruoslahti |
| 2013/0115167 A1* | 5/2013 | Ruoslahti .............. A61K 51/08 424/1.69 |

FOREIGN PATENT DOCUMENTS

| | | |
|---|---|---|
| WO | 9633233 | 10/1996 |
| WO | 9700623 | 1/1997 |
| WO | 2006136586 | 12/2006 |

OTHER PUBLICATIONS

Allam, et al., "Cholera toxin triggers apoptosis in human lung cancer cell lines", Cancer Res. 57:2615-8 (1997).

Almquist, et al., "Synthesis and biological activity of a ketomethylene analogue of a tripeptide inhibitor of angiotensin converting enzyme", J Med Chem 23:1392-8 (1980).

Arap, et al., "Cancer treatment by targeted drug delivery to tumor vasculature in a mouse model", Science 279:377-380 (1998).

Bagri, et al, "Neuropilins in tumor biology", Clin. Cancer Res.,15(6):1860-4 ( 2009).

Batzri, et al., "Single bilayer liposomes prepared without sonication", Biochim Biophys Acta, 298:1015-9 (1973).

Becker,et al, "Neuropilin-1 regulates vascular endothelial growth factor-mediated endothelial permeability", Circ Res., 96(12):1257-65 (2005).

Benner, "Expanding the genetic lexicon: incorporating non-standard amino acids into proteins by ribosome-based synthesis", TIB Tech, 12, 158-63 (1994).

Berg, et al., "Physiological functions of endosomal proteolysis", Biochem. J., 307: 313-326 (1995).

Brewis, et al., "Particle assembly incorporating a VP22-BH3 fusion protein, facilitating intracellular delivery, regulated release, and apoptosis", Mol. Ther., 7:262-70 (2003).

Cahill et al., "Site specific mutagenesis with unnatural amino acids", TIBS, 14(10):400-3 (1989).

Caunt, et al, "Blocking neuropilin-2 function inhibits tumor cell metastasis", Cancer Cell,13(4):331-42 (2008).

Curnis,et al., "Coupling tumor necrosis factor-a with av integrin ligands improves its antineoplastic activity", Cancer Res. 64:565-571 (2004).

Deamer, et al., "Large volume liposomes by an ether vaporization method", Biochim Biophys Acta, 443:629-634 (1976).

Derossi, et al., "Trojan peptides: the penetratin system for intracellular delivery", Trends Cell Biol. 8:84-7 (1998).

Dervan and Burli, "Sequence-specific DNA recognition by polyamides", Curr Opin Chem Biol, 3(6):688-93 (1999).

Duckert, et al., "Prediction of proprotein convertase cleavage sites", Protein Eng. Design & Selection, 17(1):107-12 (2004).

Eliceiri and Cheresh, "Adhesion events in angiogenesis", Curr Opin Cell Biol 13:563-68 (2001).

Ellerby, et al., "Anti-cancer activity of targeted pro-apoptotic peptides", Nat. Med., 5:1032-8 (1999).

Elliott, et al. (1997) Intercellular trafficking and proten delivery by a herpesvirus structural proten, Cell, 88, 223-33 (1997).

Ellis, "The role of neuropilins in cancer" ,Mol Cancer Ther., 5(5):1099-107 ( 2006).

Fenart and Cecchelli, "Protein transport in cerebral endothelium", Meth Mole Med., 89:277-90 (2003).

Ferreira, et al.,"In uence of differentsilica dericatives in the immobilization and stabilization of a Bacillus licheniformls protease (Subtilisin Carlsberg)", J Mol Catal B: Enzymatic, 21:189-99 (2003).

Finlayson, "Albumin products" ,Seminars in Thrombosis and Hemostasis, 6:85-120 (1980).

Fogal, "Mitochondrial/cell-surface protein p32/gC1qR as a molecular target in tumor cells and tumor stroma", Cancer Res., 68(17):7210-8 (2008).

Gao, et al., "Quantum-dot nanocrystals for ultrasensitive biological labeling and multicolor optical encoding", J. Biomed. Opt. 7:532-7 (2002).

Glutzman-Poltorak, et al, "Neuropilin-2 is a receptor for the vascular endothelial growth factor (VEGF) forms VEGF-145 and VEGF-165 (Corrected)", J Biol.Chem., 275(24):18040-5 (2000).

Guttmann-Raviv, et al, "The neuropilins and their role in tumorigenesis and tumor progression" ,Cancer Lett., 231(1):1-11 (2006).

Hagedorn and Bikfalvi, "Target molecules for anti-angiogenic therapy: from basic research to clinical trials", Crit. Rev. Oncol. Hematol. 34:89-110 (2000).

Hamzah, et al., "Vascular Targeting of Anti-CD40/IL2 into Autochthonous Tumors Enhances Immunotherapy", J. Clin. Invest., 118:1691-99 (2008).

Han, et al., "Quantum-dot-tagged microbeads for multiplexed optical coding of biomolecules", Nat Biotechnol., 19: 631-5 (2001).

Hann, "On the double bond isostere of the peptide bond: preparation of an enkephalln analogue", J. Chem. Soc Perkin Trans. I 307-314 (1982).

Haspel, et al, "Binding of a C-end rule peptide to the neuropilin-1 receptor: a molecular modeling approach", Biochemistry, 50(10):1755-62 (2011).

Hauser, et al., "Oxygen transport responses to colloids and crystalloids in critically ill surgical patients", Surg Gynecol Obstet, 150:811-6 (1980).

Heldin,et al., "High interstitial fluid pressure—an obstacle in cancer therapy", Nat Rev Cancer 4:806-13 (2004).

(56) References Cited

OTHER PUBLICATIONS

Hoffman, et al., "Progressive vascular changes in a transgenic mouse model of squamous cell carcinoma", Cancer Cell, 4:383-91 (2003).
Holladay, et al., "Synthesis of hydroxyethylene and ketomethylene dipeptide isosteres", Tetrahedron Lett., 24:4401-4 (1983).
Hooper, et al., "Membrane protein secretasee", Biochem. J. 321:265-79 (1997).
Hruby, "Conformational restrictions of biologically active peptides via amino acid side chain groups", Life Sci., 31:189-99 (1982).
Hudson, et al., "Methionine enkephalin and isosteric analogues. I. Synthesis on a phenolic resin support", Int J Pept Prot Res 14:177-85 (1979).
Ibba, et al., "Towards engineering proteins by site-directed incorporation in vivo of non-natural amino acid", Biotechnology, 12, 678-82 (1994).
Ibba, "Strategies for in vitro and in vivo translation with nonnatural amino acid", Biotechnology & Genetic Engineering Reviews, 13, 197-216 (1995).
Jain, et al, "Transport of molecules, particles, and cells in solid tumors", Annu Rev Biomed Eng., 1:241-63 (1999).
Jennings-White, et al., "Synthesis of ketomethylene analogs of dipeptides", Tetrahedron Lett 23: 2533 (1982).
Joyce, et al.,"Stage-specific vascular markers revealed by phage display in a mouse model of pancreatic islet tumorigenesis", Cancer Cell, 4:393.403 (2003).
Karmali, et al., "Targeting of albumin-embedded paclitaxel nanoparticles to tumors", Nanomedicine 5:73-82 (2009).
Kirsch, et al., "Anti-angiogenic treatment strategies for malignant brain tumors", J. Neurooncol. 50:149-163 (2000).
Kohori, et al., "Control of adriamycin cytotoxic activity using thermally responsive polymeric micelles composed of poly(N-isopropylacrylamide-co-N,N-dimethylacrylamide)-b-poly(D,L-lactide).—", Colloids Surfaces B: Biointerfaces 16: 195-205, (1999).
Kohori, et al., "Preparation and characterization of thermally Responsive block copolymer micelles comprising poly(N-isopropylacrylamide-b-D,L-lactide)", J. Control. Rel., 55:87-98, (1998).
Kreitman and Pastan, "Recombinant toxins containing human granulocyte-macrophage colony-stimulating factor and either pseudomonas exotoxin or diphtheria toxin kill gastrointestinal cancer and leukemia cells", Blood, 90:252-9 (1997).
Laakkonen, et al., "A tumor-homing peptide with a targeting specificity related to lymphatic vessels", Nature Med., 8:751-55 (2002).
Laakkonen, et al., "Antitumor activity of a homing peptide that targets tumor lymphatics and tumor cells", PNAS, 101:9381-86 (2004).
Liggins and Burt, "Polyether-polyester diblock copolymers for the preparation of paclitaxel loaded polymeric micelle formulations", Adv. Drug Del. Rev., 54:191-202 (2002).
Lin, et al., "Photonic pseudo-gap-based modification of photoluminescence from CdS nanocrystal satellites around polymer microspheres in a photonic crystal", Appl. Phys Lett. 2002, 81:3134 (2002).
Mamluk, et al, "Soluble neuropilin targeted to the skin inhibits vascular permeability",Angiogenesis,8(3):217-27 (2005).
Martin, et al., "Cancer gene therapy by thyroid hormone-mediated expression of toxin genes", Cancer Res. 60:3218-24 (2000).
Meade and Dowdy, "Exogenous siRNA delivery using peptide transduction domains/cell penetrating peptides", Adv. Drug Delivery Reviews. 59(2-3):134-40 (2007).
Moghimi, et al. "Long-circulating and target-specific nanoparticles: Theory to practice", Pharm. Rev., 53:283-318 (2001).
Murakami and Etlinger, "Degradation of proteins with blocked amino groups by cytoplasmic proteases", Biochem. Biophys. Res. Comm., 146:1249-59 (1987).
Murphy, et al., "Nanoparticle-mediated drug delivery to tumor vasculature suppresses metastasis", PNAS, 105:9343-8 (2008).
Osborne and Coronado-Heinsohn, Targeting the epidermal growth factor receptor in breast cancer cell lines with a recombinant ligand fusion toxin (DAB389EGF). Cancer J. Sci. Am., 2:175 (1996).
Pai, et al., "Microscopic flow visualization system for fluids in magnetic field", Mag. & Magnetic Mater., 194:262-6 (1999).
Papahadjopoulos, et al., "Phospholipid model membranes. I. Structural characteristics of hydrated liquid crystals", Biochim Biophys Acta., 135:624-38 (1968).
Park, et al.,"Systematic surface engineering of magnetic nanoworms for in vivo tumor targeting", Small, 5:694-700 (2009).
Pierschbacher and Ruoslahtii, "Cell attachment activity of fibronectin can be duplicated by small synthetic fragments of the molecule", Nature, 309:30-3 (1984).
Pirollo, et al.,"Materializing the potential of small interfering RNA via a tumor-targeting nanodelivery system", Cancer Res.,67:2938-43 (2007).
Ruoslahti, et al., "Targeting of drugs and nanoparticles to tumors", J Cell Biol., 188(6):759-68 (2010).
Ruoslahti, "Specialization of tumour vasculature", Nat. Rev. Cancer, 2:83-90 (2002).
Ruoslahti, "The RGD story: a personal account", Matrix Biol., 22:459-65 (2003).
Simberg, et al., "Biomimetic amplification of nanoparticle homing to tumors", PNAS, 104:932-6 (2007).
Sipkins, et al., "Detection of tumor angiogenesis in vivo by alphaVbeta3-targeted magnetic resonance imaging", Nat. Med., 4:623-6 (1998).
Smyth and Trapani, "Granzymes: exogenous proteinases that induce target cell apoptosis", Immunology Today, 16: 202-6 (1995).
Soker, et al., "Neuropilin-1 is expressed by endothelial and tumor cells as an isoform-specific receptor for vascular endothelial growth factor", Cell, 92:735-45 (1998).
Spatola, et al., "Structure-activity relationships of enkephalins containing serially replaced thiomethylene amide bond surrogates", Life Scie 38: 1243-9 (1986).
Sugahara, et al., "Coadminlstration of a Tumor-Penetrating Peptide Enhances the Efficacy of Cancer Drugs", Science, 328:1031-5 (2010).
Sugahara, et al.,"TIssue-penetrating delivery of compounds and nanoparticles into tumors", Cancer Cell, 16(6):510-20 (2009).
Talanian, et al., "Substrate specificities of caspase family proteases", J. Biol. Chem., 272: 9677-9682 (1997).
Teesalu, et al., "C-end rule peptides mediate neuropilin-1-dependent cell, vascular, and tissue penetration", PNAS, 106(38):16157-16162 (2009).
Thorek, et al, "Superparamagnetic iron oxide nanoparticle probes for molecular imaging",Ann Biomed Eng.,24(1):23-38 (2006).
Thornberry, et al., "A combinatorial approach defines specificities of members of the caspase family and granzyme B. Functional relationships established for key mediators of apoptosis", J. Biol. Chem. 272:17907-17911 (1997).
Thorson, et al.,"A biosynthetic approach for the incorporation of unnatural amino acids into proteins", Methods in Molec. Biol., 77:43-73 (1991).
Tkachenko et al., "Multifunctional gold nanoparticle-peptide complexes for nuclear targeting", J Am Chem Soc., 125:4700-01(2003).
Tullis, "Albumin. 1. Background and use", JAMA, 237(4):355-60 (1977A).
Tullis, "Albumin. 2. Guidelines for clinical use", JAMA, 237(5):460-63 (1977B).
Tuzar and Kratochvil, "Block and graft copolymer micelles in solution", Adv. Colloid Interface Sci., 6:201-32 (1976).
Von Maltzahn, et al, "In vivo tumor cell targeting with "click" nanoparticles",Bioconjug Chem., 19(8):1570-8 (2008).
Wang, et al., "Composite photonic crystals from semiconductor nanocrystal/polyelectrolyte-coated colloidal spheres", Chem. Mater., 15:2724-9 (2003).
Wemmer and Dervan, "Targeting the minor groove of DNA", Curr Opin Struct Biol, 7(3):355-61 (1997).
Werb, "ECM and cell surface proteolysls: regulating cellular ecology", Cell, 91:439-442 (1997).
Wilhelm, et al., "Poly(styrene-ethylene oxide) block copolymer micelle formation in water: a fluorescence probe study.", Macromolecules 24:1033-40 (1991).

(56) References Cited

OTHER PUBLICATIONS

Wolfsberg, et al., "ADAM, a novel family of membrane proteins containing a Disintegrin and Metalloprotease domain: multipotential functions in cell-cell and cell-matrix interactions", J. Cell Biol., 131:275-278 (1995).
Zhang, et al., "Development of amphiphilic dibiock copolymers as micellar carriers of taxol", Int. J. Pharm. 132: 195-206, (1996).
Zhang, et al., "Molecular profiling of heart endothelial cells", Circulation. 112:1601-11 (2005).
Zoller, "New recombinant DNA methodology for protein engineering", Current Opin. in Biotech., 3:348-54 (1992).
Zorko and Langel, "Cell-penetrating peptides: mechanism and kinetics of cargo delivery" ,Adv Drug Deilv Rev. 57:529-45 (2005).

\* cited by examiner

TRUNCATED LYP-1 PEPTIDES AND METHODS AND COMPOSITIONS USING TRUNCATED LYP-1 PEPTIDES

CROSS-REFERENCE TO RELATED APPLICATIONS

This application claims benefit of U.S. Provisional Application No. 61/527,789, filed Aug. 26, 2012. Application No. 61/527,789, filed Aug. 26, 2012, is hereby incorporated herein by reference in its entirety.

STATEMENT REGARDING FEDERALLY SPONSORED RESEARCH

This invention was made with government support under grant W81XWH-09-1-0698 from the Department of Defense (DOD). The government has certain rights in the invention.

REFERENCE TO SEQUENCE LISTING

The Sequence Listing submitted Jan. 30, 2018, as a text file named "SBMRI_58_8402_AMD_AFD_Sequence_Listing.txt," created on Jan. 23, 2018, and having a size of 41,097 bytes is hereby incorporated by reference pursuant to 37 C.F.R. § 1.52(e)(5).

FIELD OF THE INVENTION

The present invention relates generally to the field of molecular medicine, more specifically, to cell and tissue-targeting peptides.

BACKGROUND OF THE INVENTION

Peptides that are internalized into cells are commonly referred to as cell-penetrating peptides. There are two main classes of such peptides: hydrophobic and cationic (Zorko and Langel, 2005). The cationic peptides, which are commonly used to introduce nucleic acids, proteins into cells, include the prototypic cell-penetrating peptides (CPP), Tat, and penetratin (Derossi et al., 1998; Meade and Dowdy, 2007). A herpes virus protein, VP22, is capable of both entering and exiting cells and carrying a payload with it (Elliott and O'Hare, 1997; Brewis et al., 2003). A major limitation of these peptides as delivery vehicles is that they are not selective; they enter into all cells.

Tissue penetration is a serious limitation in the delivery of compositions to cells. Comparison of the distribution of fluorescein-labeled peptides to that of iron oxide particles coated with the same peptide shows that the particles remain close to the tumor blood vessels, whereas the fluorescent peptide reaches all areas of the tumor. The frequently cited "leakiness" of tumor vessels does not appear to substantially mitigate this problem. Moreover, anti-angiogenic treatments that cause "normalization" of tumor vasculature (Jain, 2005), creating a need to target tumors whose vasculature is not leaky. Thus, it is important to find new ways of improving the passage of diverse compositions into the extravascular space. A number of proteins are known to translocate through the endothelium of blood vessels, including the blood-brain barrier. A prime example is transferrin, which is carried across the blood-brain barrier by the transferrin receptor. This system has been used to bring other payloads into the brain (Li et al., 2002; Fenart and Cecchelli, 2003). Peptide signals for endothelial transcytosis that can mediate translocation of compositions from the circulation into tissues is useful.

Thus, there is a need for new therapeutic strategies for selectively targeting various types of cells, and for internalizing proteins and peptides into those cells and penetration of tissue by proteins and peptides. There is also a need for increasing the delivery of compounds and compositions to and into cells and tissues. The present invention satisfies these needs by providing peptides that can be selectively targeted, and selectively internalized, by cells and/or can penetrate tissue. Related advantages also are provided.

BRIEF SUMMARY OF THE INVENTION

Disclosed are peptides that target tumor vasculature, are readily internalized into adjacent cells, and extensively penetrate and invade tumor tissue. The disclosed peptides can also mediate targeting, internalization, and tissue penetration of compounds and compositions coupled to, associated with, conjugated to, or even co-administered with the peptide. Examples of the disclosed peptides include peptides where the C-terminal end of the peptide consists of the amino acid sequence CGNKRTR (SEQ ID NO:4) and peptides consisting of CGNKRTR (SEQ ID NO:4). The disclosed peptides can be used in and with a variety of compositions and methods to, for example, enhancing internalization, penetration, or both of such compositions into or through a cell, tissue, or both. Such compositions and methods are also disclosed herein.

Disclosed are peptides where the C-terminal end of the peptide consists of the amino acid sequence CGNKRTR (SEQ ID NO:4). In some forms, the peptide can be a modified peptide. In some forms, the peptide can be a methylated peptide. In some forms, one or more of the methylated peptide can comprise a methylated amino acid segment. In some forms, the peptide can be N- or C-methylated in at least one position.

Also disclosed are compositions comprising the disclosed peptide. In some forms, the composition can further comprise a co-composition, where the peptide and the co-composition are not covalently coupled or non-covalently associated with each other. In some forms, the composition can further comprise a cargo composition, where the peptide and the cargo composition are covalently coupled or non-covalently associated with each other.

In some forms, the peptide can selectively home to a tumor. In some forms, the peptide can selectively home to tumor vasculature. In some forms, the peptide and the co-composition are not bound to each other. In some forms, the co-composition and/or cargo composition can comprise a therapeutic agent. In some forms, the co-composition and/or cargo composition can comprise a detection agent. In some forms, the co-composition and/or cargo composition can comprise a carrier, vehicle, or both. In some forms, the co-composition and/or cargo composition can comprise a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, an anti-angiogenic agent, or a combination.

In some forms, the peptide can be an activatable peptide. The activatable peptide can be a protease-activatable peptide. The protein or peptide can be circular. The protein or peptide can be linear.

In some forms, the peptide can be comprised in a tLyP-1 composition. In some forms, the tLyP-1 composition can comprise one or more cargo compositions. In some forms, the tLyP-1 composition can comprise one or more homing molecules. In some forms, the peptide can be comprised in a tLyP-1 conjugate. In some forms, the tLyP-1 conjugate can comprise one or more cargo compositions. In some forms, the tLyP-1 conjugate can comprise one or more homing molecules. In some forms, the composition can comprise a plurality of cargo compositions. In some forms, the composition can comprise a plurality of copies of the peptide. In some forms, the composition can comprise a plurality of co-compositions.

In some forms, the composition can further comprise a surface molecule and a plurality of membrane perturbing molecules. In some forms, the composition can further comprise one or more homing molecules, wherein the homing molecules selectively home to tumor vasculature. In some forms, the co-composition can comprise a surface molecule, one or more homing molecules, and a plurality of membrane perturbing molecules, wherein the homing molecules selectively home to tumor vasculature. In some forms, the cargo composition can comprise a surface molecule, one or more homing molecules, and a plurality of membrane perturbing molecules, wherein the homing molecules selectively home to tumor vasculature.

In some forms, one or more of the homing molecules can comprise the amino acid sequence CGKRK (SEQ ID NO:1) or a conservative derivative thereof, the amino acid sequence CRKDKC (SEQ ID NO:2) or a conservative derivative thereof, or a combination. In some forms, one or more of the homing molecules can comprise the amino acid sequence CGKRK (SEQ ID NO:1) or a conservative variant thereof. In some forms, one or more of the homing molecules can comprise the amino acid sequence CGKRK (SEQ ID NO:1). In some forms, all of the one or more homing molecules can comprise the amino acid sequence CGKRK (SEQ ID NO:1) or a conservative derivative thereof, the amino acid sequence CRKDKC (SEQ ID NO:2) or a conservative derivative thereof, or a combination.

In some forms, one or more of the membrane perturbing molecules can comprise the amino acid sequence $_D$(KLAKLAK)$_2$ (SEQ ID NO:3) or a conservative variant thereof, (KLAKLAK)$_2$ (SEQ ID NO:3) or a conservative variant thereof, (KLAKKLA)$_2$ (SEQ ID NO:5) or a conservative variant thereof, (KAAKKAA)$_2$ (SEQ ID NO:6) or a conservative variant thereof, or (KLGKKLG)$_3$ (SEQ ID NO:7) or a conservative variant thereof, or a combination. In some forms, one or more of the membrane perturbing molecules can comprise the amino acid sequence $_D$(KLAKLAK)$_2$ (SEQ ID NO:3), (KLAKLAK)$_2$ (SEQ ID NO:3), (KLAKKLA)$_2$ (SEQ ID NO:5), (KAAKKAA)$_2$ (SEQ ID NO:6), or (KLGKKLG)$_3$ (SEQ ID NO:7), or a combination. In some forms, one or more of the membrane perturbing molecules can comprise the amino acid sequence $_D$(KLAKLAK)$_2$ (SEQ ID NO:3) or a conservative variant thereof. In some forms, one or more of the membrane perturbing molecules can comprise the amino acid sequence $_D$(KLAKLAK)$_2$ (SEQ ID NO:3).

In some forms, one or more of the membrane perturbing molecules can be conjugated to one or more of the homing molecules. In some forms, the homing molecules can be conjugated with the surface molecule. In some forms, the membrane perturbing molecules can be conjugated with the surface molecule. In some forms, one or more of the conjugated homing molecules can be indirectly conjugated to the surface molecule via a linker, one or more of the conjugated membrane perturbing molecules can be indirectly conjugated to the surface molecule via a linker, or both. In some forms, the composition can further comprise a plurality of linkers. In some forms, at least one of the linkers can comprise polyethylene glycol.

In some forms, the composition can bind inside tumor blood vessels. In some forms, the composition can be internalized in cells. In some forms, the composition can penetrate tissue. In some forms, the composition can reduce tumor growth.

In some forms, the surface molecule can comprise a nanoparticle, a nanoworm, an iron oxide nanoworm, an iron oxide nanoparticle, an albumin nanoparticle, a liposome, a micelle, a phospholipid, a polymer, a microparticle, or a fluorocarbon microbubble. In some forms, the composition can comprise at least 100 homing molecules. In some forms, the composition can comprise at least 1000 homing molecules. In some forms, the composition can comprise at least 10,000 homing molecules. In some forms, the composition can comprise at least 100 membrane perturbing molecules. In some forms, the composition can comprise at least 1000 membrane perturbing molecules. In some forms, the composition can comprise at least 10,000 membrane perturbing molecules. In some forms, the composition can comprise at least 100 copies of the peptide. In some forms, the composition can comprise at least 1000 copies of the peptide. In some forms, the composition can comprise at least 10,000 copies of the peptide.

In some forms, the composition, tLyP-1 composition, co-composition, or cargo composition can comprise a plurality of surface molecules, a plurality of homing molecules and a plurality of cargo molecules. In some forms, the composition, tLyP-1 composition, co-composition, or cargo composition can comprise one or more surface molecules, a plurality of homing molecules and a plurality of cargo molecules. In some forms, the composition, tLyP-1 composition, co-composition, or cargo composition can comprise a plurality of surface molecules, one or more homing molecules and a plurality of cargo molecules. In some forms, the composition, tLyP-1 composition, co-composition, or cargo composition can comprise a plurality of surface molecules, a plurality of homing molecules and one or more cargo molecules. In some forms, the composition, tLyP-1 composition, co-composition, or cargo composition can comprise one or more surface molecules, one or more homing molecules and a plurality of cargo molecules. In some forms, the composition, tLyP-1 composition, co-composition, or cargo composition can comprise one or more surface molecules, a plurality of homing molecules and one or more cargo molecules. In some forms, the composition, tLyP-1 composition, co-composition, or cargo composition can comprise a plurality of surface molecules, one or more homing molecules and one or more cargo molecules.

In some forms, the composition, tLyP-1 composition, co-composition, or cargo composition can comprise a surface molecule, a plurality of homing molecules and a plurality of cargo molecules, wherein one or more of the homing molecules and one or more of the cargo molecules are associated with the surface molecule. In some forms, the composition, tLyP-1 composition, co-composition, or cargo composition can comprise a surface molecule, a plurality of homing molecules and a plurality of cargo molecules, wherein a plurality of the plurality of homing molecules and a plurality of the plurality of cargo molecules are associated with the surface molecule. In some forms, the composition, tLyP-1 composition, co-composition, or cargo composition can comprise a surface molecule, a plurality of homing molecules and a plurality of cargo molecules, wherein the homing molecules and the cargo molecules are associated with the surface molecule.

In some forms, the composition, tLyP-1 composition, co-composition, or cargo composition can comprise a surface molecule, wherein the surface molecule is multivalent for homing molecules and cargo molecules. In some forms, the composition, tLyP-1 composition, co-composition, or cargo composition can comprise a surface molecule, wherein the surface molecule is multivalent for homing molecules and comprises one or more cargo molecules. In some forms, the composition, tLyP-1 composition, co-composition, or cargo composition can comprise a surface molecule, wherein the surface molecule is multivalent for cargo molecules and comprises one or more homing molecules. In some forms, the composition, tLyP-1 composition, co-composition, or cargo composition can comprise a surface molecule, wherein the surface molecule is multivalent for conjugates, wherein one or more of the conjugates comprise one or more homing molecules and one or more cargo molecules. In some forms, the composition, tLyP-1 composition, co-composition, or cargo composition can comprise a surface molecule, wherein the surface molecule is multivalent for conjugates, wherein one or more of the conjugates comprise a plurality of homing molecules and a plurality cargo molecules. In some forms, the composition, tLyP-1 composition, co-composition, or cargo composition can comprise a surface molecule, wherein the surface molecule is multivalent for conjugates, wherein one or more of the conjugates comprise a homing molecule and a cargo molecule. In some forms, the composition, tLyP-1 composition, co-composition, or cargo composition can comprise a surface molecule, wherein the surface molecule is multivalent for conjugates, wherein each of the conjugates comprises a plurality of homing molecules and a plurality cargo molecules. In some forms, the composition, tLyP-1 composition, co-composition, or cargo composition can comprise a surface molecule, wherein the surface molecule is multivalent for conjugates, wherein each of the conjugates comprises a homing molecule and a cargo molecule.

In some forms, the composition, tLyP-1 composition, co-composition, or cargo composition can comprise a surface molecule, wherein the surface molecule comprises one or more conjugates, wherein one or more of the conjugates comprise one or more homing molecules and one or more cargo molecules. In some forms, the composition, tLyP-1 composition, co-composition, or cargo composition can comprise a surface molecule, wherein the surface molecule comprises one or more conjugates, wherein one or more of the conjugates comprise a plurality of homing molecules and a plurality cargo molecules. In some forms, the composition, tLyP-1 composition, co-composition, or cargo composition can comprise a surface molecule, wherein the surface molecule comprises one or more conjugates, wherein one or more of the conjugates comprise a homing molecule and a cargo molecule. In some forms, the composition, tLyP-1 composition, co-composition, or cargo composition can comprise a surface molecule, wherein the surface molecule comprises one or more conjugates, wherein each of the conjugates comprises a plurality of homing molecules and a plurality cargo molecules. In some forms, the composition, tLyP-1 composition, co-composition, or cargo composition can comprise a surface molecule, wherein the surface molecule comprises one or more conjugates, wherein each of the conjugates comprises a homing molecule and a cargo molecule.

In some forms, one or more of the membrane perturbing molecules can be conjugated to one or more of the homing molecules. In some forms, one or more of the conjugated membrane perturbing molecules and homing molecules can be covalently coupled. In some forms, one or more of the covalently coupled membrane perturbing molecules and homing molecules can comprise fusion peptides. In some forms, the homing molecules can be conjugated with the surface molecule. In some forms, one or more of the conjugated homing molecules can be directly conjugated to the surface molecule. In some forms, one or more of the conjugated homing molecules can be indirectly conjugated to the surface molecule. In some forms, one or more of the homing molecules can be covalently coupled to the surface molecule. In some forms, one or more of the covalently coupled homing molecules can be directly covalently coupled to the surface molecule. In some forms, one or more of the covalently coupled homing molecules can be indirectly covalently coupled to the surface molecule. In some forms, the membrane perturbing molecules can be conjugated with the surface molecule. In some forms, one or more of the conjugated membrane perturbing molecules are directly conjugated to the surface molecule. In some forms, one or more of the conjugated membrane perturbing molecules can be indirectly conjugated to the surface molecule. In some forms, one or more of the membrane perturbing molecules can be covalently coupled to the surface molecule. In some forms, one or more of the covalently coupled membrane perturbing molecules can be directly covalently coupled to the surface molecule. In some forms, one or more of the covalently coupled membrane perturbing molecules can be indirectly covalently coupled to the surface molecule.

In some forms, the surface molecule can comprise a nanoparticle. In some forms, the surface molecule can comprise a nanoworm. In some forms, the surface molecule can comprise an iron oxide nanoworm. In some forms, the surface molecule can comprise an iron oxide nanoparticle. In some forms, the surface molecule can comprise an albumin nanoparticle. In some forms, the surface molecule can comprise a liposome. In some forms, the surface molecule can comprise a micelle. In some forms, the surface molecule comprises a phospholipid. In some forms, the surface molecule comprises a polymer. In some forms, the surface molecule can comprise a microparticle. In some forms, the surface molecule can comprise a fluorocarbon microbubble.

In some forms, the composition, tLyP-1 composition, co-composition, or cargo composition can comprise at least 100 homing molecules. In some forms, the composition, tLyP-1 composition, co-composition, or cargo composition can comprise at least 1000 homing molecules. In some forms, the composition, tLyP-1 composition, co-composition, or cargo composition can comprise at least 10,000 homing molecules. In some forms, the composition, tLyP-1 composition, co-composition, or cargo composition can comprise at least 100 membrane perturbing molecules. In some forms, the composition, tLyP-1 composition, co-composition, or cargo composition can comprise at least 1000 membrane perturbing molecules. In some forms, the composition, tLyP-1 composition, co-composition, or cargo composition can comprise at least 10,000 membrane perturbing molecules. In some forms, the composition, tLyP-1 composition, co-composition, or cargo composition can comprise at least 100 tLyP-1 peptides. In some forms, the composition, tLyP-1 composition, co-composition, or cargo composition can comprise at least 1000 tLyP-1 peptides. In some forms, the composition, tLyP-1 composition, co-composition, or cargo composition can comprise at least 10,000 tLyP-1 peptides.

In some forms, one or more of the homing molecules can be modified homing molecules. In some forms, one or more of the homing molecules can comprise a methylated homing molecule. In some forms, one or more of the methylated homing molecules can comprise a methylated amino acid segment. In some forms, one or more of the membrane perturbing molecules can be modified membrane perturbing molecules. In some forms, one or more of the membrane perturbing molecules can comprise a methylated membrane perturbing molecule. In some forms, one or more of the methylated membrane perturbing molecules can comprise a methylated amino acid segment. In some forms, the amino acid segment can be N- or C-methylated in at least one position.

In some forms, the composition can further comprise one or more moieties. In some forms, the moieties can be independently selected from the group consisting of, for example, an anti-angiogenic agent, a pro-angiogenic agent, a cancer chemotherapeutic agent, a cytotoxic agent, a polypeptide, a nucleic acid molecule, a small molecule, an image contrast agent, a fluorophore, fluorescein, rhodamine, a radionuclide, indium-111, technetium-99, carbon-11, and carbon-13. In some forms, at least one of the moieties can be a therapeutic agent. In some forms, the therapeutic agent can be Abraxane. In some forms, the therapeutic agent can be paclitaxel. In some forms, the therapeutic agent can be taxol. In some forms, at least one of the moieties can be a detectable agent. In some forms, the detectable agent can be FAM.

In some forms, one or more of the homing molecules can comprise the amino acid sequence CGKRK (SEQ ID NO:1), where one or more of the membrane perturbing molecules can comprise the amino acid sequence $_D$(KLAKLAK)$_2$ (SEQ ID NO:3), where one or more of the homing molecules can be indirectly conjugated to the surface molecule via a linker, and where one or more of the membrane perturbing molecules can be indirectly conjugated to the surface molecule via a linker. In some forms, at least one of the linkers can comprise polyethylene glycol.

Also disclosed are methods of enhancing internalization, penetration, or both of a co-composition into or through a cell, tissue, or both. In some forms, the method can comprising exposing the cell, tissue, or both to the co-composition and a tLyP-1 composition, thereby enhancing internalization, penetration, or both of the co-composition into or through the cell, tissue, or both. The tLyP-1 composition can comprise any of the disclosed tLyP-1 peptides or any of the disclosed compositions that comprise a tLyP-1 peptide. In some forms, the tLyP-1 composition and the co-composition are not covalently coupled or non-covalently associated with each other prior to exposing the cell, tissue, or both.

Also disclosed are methods of enhancing internalization, penetration, or both of a cargo composition into or through a cell, tissue, or both. In some forms, the method can comprise exposing the cell, tissue, or both to the cargo composition and a tLyP-1 composition, thereby enhancing internalization, penetration, or both of the cargo composition into or through the cell, tissue, or both. The tLyP-1 composition can comprise any of the disclosed tLyP-1 peptides or any of the disclosed compositions that comprise a tLyP-1 peptide. In some forms, the tLyP-1 composition and the cargo composition can be covalently coupled or non-covalently associated with each other.

Also disclosed are methods of enhancing internalization, penetration, or both into or through a cell, tissue, or both. In some forms, the method can comprise exposing the cell, tissue, or both to a tLyP-1 composition, thereby enhancing internalization, penetration, or both into or through the cell, tissue, or both. The tLyP-1 composition can comprise any of the disclosed tLyP-1 peptides or any of the disclosed compositions that comprise a tLyP-1 peptide.

In some forms, the cell, tissue, or both can be in a subject. In some forms, the cell, tissue, or both can be exposed to the tLyP-1 composition and the co-composition by administering the tLyP-1 composition and the co-composition to the subject. In some forms, the cell, tissue, or both can be exposed to the tLyP-1 composition and the cargo composition by administering the tLyP-1 composition and the cargo composition to the subject. In some forms, the cell, tissue, or both can be exposed to the tLyP-1 composition by administering the tLyP-1 composition to the subject.

In some forms, the tLyP-1 composition can selectively home to a tumor. In some forms, the tLyP-1 composition can selectively home to tumor vasculature. In some forms, the tLyP-1 composition and the co-composition can be administered to the subject simultaneously. In some forms, the tLyP-1 composition and the co-composition can be administered to the subject in a single composition comprising the tLyP-1 composition and the co-composition. In some forms, the tLyP-1 composition and the co-composition can be administered to the subject in separate compositions. In some forms, the tLyP-1 composition and the co-composition can be administered to the subject at different times. In some forms, the tLyP-1 composition and the co-composition can be administered to the subject in separate compositions. In some forms, the tLyP-1 composition and the co-composition can be administered to the subject by separate routes.

In some forms, the tLyP-1 composition and the co-composition are not bound to each other. In some forms, the tLyP-1 composition, co-composition, and/or cargo composition can comprise a therapeutic agent. In some forms, the tLyP-1 composition, co-composition, and/or cargo composition can comprise a detection agent. In some forms, the tLyP-1 composition, co-composition, and/or cargo composition can comprise a carrier, vehicle, or both. In some forms, the tLyP-1 composition, co-composition, and/or cargo composition can comprise a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, an anti-angiogenic agent, a pro-angiogenic agent, or a combination.

In some forms, the tLyP-1 composition can comprise one or more accessory molecules. In some forms, the cell, tissue, or both can be exposed to a plurality of homing molecules. In some forms, the cell, tissue, or both can be exposed to a plurality of cargo compositions. In some forms, the cell, tissue, or both can be exposed to a plurality of tLyP-1 compositions. In some forms, the cell, tissue, or both can be exposed to a plurality of co-compositions.

In some forms, the tLyP-1 composition, co-composition, and/or cargo composition can have a therapeutic effect. In some forms, the therapeutic effect can be a slowing in the increase of or a reduction of tumor burden. In some forms, the therapeutic effect can be a slowing of the increase of or reduction of tumor size. In some forms, the subject can have one or more sites to be targeted, where the tLyP-1 composition, co-composition, and/or cargo composition homes to one or more of the sites to be targeted. In some forms, the subject can have a tumor, where the tLyP-1 composition, co-composition, and/or cargo composition has a therapeutic effect on the tumor. In some forms, the tLyP-1 composition, co-composition, and/or cargo composition can penetrate tissue. In some forms, the tLyP-1 composition, co-composition, and/or cargo composition can penetrate tumor tissue.

The peptide can be an activatable peptide. The peptide can be a protease-activatable peptide. The protein or peptide can be circular (cyclic) or can contain a loop. The peptide can be at the C-terminal end of the protein or peptide. The peptide can comprise a terminal carboxyl group. A blocking group can be coupled to the terminal carboxyl group. The bond coupling the blocking group and the terminal carboxyl group can be selected to be cleavable by a protease, enzyme, cleaving agent, and/or cleaving conditions present in proximity to the cell of interest. The blocking group can be coupled to the C-terminal amino acid of the peptide. The blocking group can be coupled to an amino acid of the peptide other than the C-terminal amino acid of the peptide. The blocking group can comprise or consist of an amino acid or an amino acid sequence.

Also disclosed are methods of producing an activatable peptide that can be activated in proximity to a cell of interest, the method comprising forming an activatable peptide wherein a blocking group is coupled to a peptide via a cleavable bond, wherein the cleavable bond is cleavable by an enzyme, cleaving agent, and/or cleaving conditions present in proximity to the cell of interest. Also disclosed are methods of producing an activatable peptide that can be activated in proximity to a cell of interest, the method comprising forming an activatable peptide wherein a blocking group is coupled to a peptide via a cleavable bond, wherein the cleavable bond is cleavable by an enzyme, cleaving agent, and/or cleaving conditions present in proximity to the cell of interest. The cell can be in a subject. The enzyme, cleaving agent, and/or cleaving conditions that is present in proximity to the cell of interest can be identified. The enzyme, cleaving agent, and/or cleaving conditions present in proximity to the cell of interest can be identified prior to forming the activatable peptide. The cleavable bond can be selected based on the enzyme that is present in proximity to the cell of interest. The cleavable bond can be selected based on the cleaving agent present at site where the peptide is delivered, homes, travels or accumulates, such as the cell of interest. The cleavable bond can be selected based on the cleaving conditions present at site where the peptide is delivered, homes, travels or accumulates, such as the cell of interest. The cleavable bond can be selected prior to forming the activatable peptide. The peptide can comprise a terminal carboxyl group, wherein the blocking group is coupled to the terminal carboxyl group. Also disclosed are methods of producing an activatable peptide, the method comprising forming an activatable peptide wherein a blocking group is coupled to a peptide via a cleavable bond. The cleavable bond can be cleaved in any suitable way. For example, the cleavable bond can be cleaved enzymatically or non-enzymatically. For enzymatic cleavage, the cleaving enzyme can be supplied or can be present at a site where the peptide is delivered, homes, travels or accumulates. For example, the enzyme can be present in proximity to a cell to which the peptide is delivered, homes, travels, or accumulates. For non-enzymatic cleavage, the peptide can be brought into contact with a cleaving agent, can be placed in cleaving conditions, or both. A cleaving agent is any substance that can mediate or stimulate cleavage of the cleavable bond. Cleaving conditions can be any solution or environmental conditions that can mediate or stimulate cleavage of the cleavable bond.

Also disclosed are methods of forming an activatable peptide, the method comprising causing a blocking group to be covalently coupled to a peptide, wherein a bond coupling the blocking group and the peptide is cleavable. Also disclosed are methods of forming an activatable peptide, the method comprising causing a blocking group to be covalently coupled to an amino acid sequence, wherein the amino acid sequence comprises a peptide the peptide, wherein a bond coupling the blocking group and the peptide is cleavable. Also disclosed are methods of forming an activatable peptide, the method comprising (a) selecting an amino acid sequence for internalization into a cell and/or penetration of tissue, wherein the amino acid sequence comprises a peptide, and (b) causing a blocking group to be covalently coupled to the peptide, wherein a bond coupling the blocking group and the peptide is cleavable. The blocking group covalently coupled to the peptide reduces or prevents internalization into a cell and/or penetration of tissue. The blocking group covalently coupled to the peptide can reduce or prevent internalization into a cell and/or penetration of tissue compared to the same peptide with no blocking group. For example, an amino acid sequence comprising tLyP-1 sequence-cleavage site-homing module can be made and then tested for activatability (via cleavage of the cleavage site, for example). For example, a pool of peptides having the amino acid sequence CGNKRTR-XXXXXXXXXXXXXXXXXX (SEQ ID NO:8) can be tested for homing and activatability. That is, such peptides can be identified by screens using libraries. The activatable peptide can comprise the selected amino acid sequence and the blocking group. The cell can be in a subject. The enzyme, cleaving agent, and/or cleaving conditions present in proximity to the cell of interest can be identified. The enzyme, cleaving agent, and/or cleaving conditions present in proximity to the cell of interest can be identified prior to forming the activatable peptide. The cleavable bond can be selected based on the enzyme that is present in proximity to the cell of interest. The cleavable bond can be selected based on the cleaving agent present at site where the peptide is delivered, homes, travels or accumulates, such as the cell of interest. The cleavable bond can be selected based on the cleaving conditions present at site where the peptide is delivered, homes, travels or accumulates, such as the cell of interest. The cleavable bond can be selected prior to forming the activatable peptide. The peptide can comprise a terminal carboxyl group, wherein the blocking group is coupled to the terminal carboxyl group.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figures 1A, 1B:
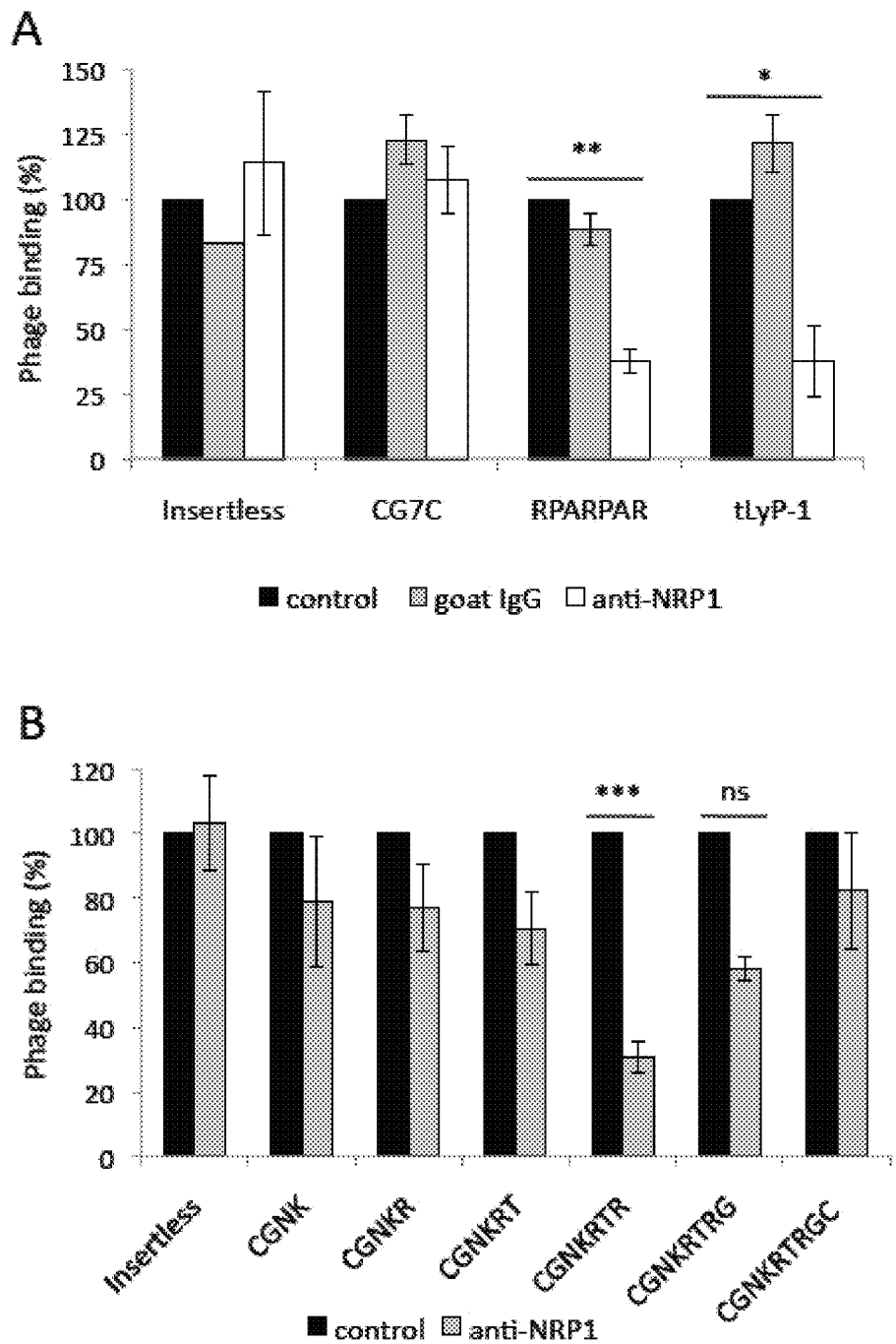
FIGS. 1A, 1B, and 1C show CGNKRTR (SEQ ID NO:4) is the active CendR element of LyP-1. A. DU145 cells were incubated with phage at 4° C. to assess NRP1 binding. Ligand-blocking anti-NRP1 inhibited binding of both CGNKRTR (SEQ ID NO:4) and RPARPAR phage (SEQ ID NO:9), whereas goat IgG had no effect. Insertless and CG7C control phage binding was not inhibited. Binding is expressed as percentage of binding in control conditions. (mean±SEM; n=4/group; * p<0.05; , p<0.01). B. DU145 cells were incubated with various truncated versions of LyP-1 phage at 4° C. to determine the minimum essential element for NRP1 binding. Ligand-blocking anti-NRP1 inhibited binding of CGNKRTR (SEQ ID NO:4) but not of the other phage. Insertless phage binding was not inhibited. Binding is expressed as percentage of binding in control conditions. Other phage peptides are CGNK (amino acids 1-4 of SEQ ID NO:10), CGNKR (amino acids 1-5 of SEQ ID NO:10), CGNKRT (amino acids 1-6 of SEQ ID NO:10), CGNKRTR (amino acids 1-7 of SEQ ID NO:10), CGNKRTRG (amino acids 1-8 of SEQ ID NO:10), CGNKRTRGC (SEQ ID NO:10). (mean±SEM; n=5/group; *, p<0.001; ns, not significant). C. Tissue distribution of intravenously injected phage after 15 min circulation in normal mice. tLyP-1 phage significantly accumulated in the lungs. The titer of phage is expressed as fold over control insertless phage. (mean±SEM; n=3/group; * p<0.05; , p<0.01; *, p<0.001).

The disclosed method and compositions can be understood more readily by reference to the following detailed description of particular embodiments and the Examples included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

B. General

Disclosed herein are peptides that enable intracellular delivery, exit and tissue penetration of compositions. The delivery can be targeted to cells or tissues of interest, such as tumors. Internalization of compositions (including nanoparticles, drugs, detectable markers, and other compounds) and their payload into target cells and penetration into target tissue can increase the efficiency of the targeting and the effectiveness of the payload.

A class of peptides was recently described that improves drug delivery by increasing penetration of drugs into solid tumors. These peptides contain a C-terminal C-end Rule (CendR) sequence motif (R/K)XX(R/K), which is responsible for cell internalization and tissue penetration activity. Tumor-specific CendR peptides contain a cryptic CendR motif that is proteolytically unmasked in tumor tissue. A previously described cyclic tumor-homing peptide, LyP-1 (sequence: CGNKRTRGC; SEQ ID NO:10), contains a CendR element and is capable of tissue penetration. Described herein is a truncated form of LyP-1, in which CendR motif is exposed (CGNKRTR; tLyP-1; SEQ ID NO:4), and inhibition of the CendR receptor, neuropilin-1 to show that LyP-1 and tLyP-1 internalized into cells through the CendR internalization pathway. It was discovered that neuropilin-2 binds tLyP-1 and that the binding activates the CendR pathway. The neuropilins are generally overexpressed in tumors (Bagri et al., 2009), and fluorescein-labeled tLyP-1 peptide and tLyP-1-conjugated nanoparticles show selective homing to tumors, penetrating from the blood vessels into the tumor parenchyma. The truncated peptide is more potent in this regard than the parent peptide LyP-1. These properties make tLyP-1 a useful tool for targeted delivery of therapeutic and diagnostic agents to breast cancers and perhaps other types of tumors as well.

Targeted delivery of therapeutic or diagnostic agents to tumors constitutes a major goal in cancer treatment. By increasing the amount of a drug reaching the tumor, efficacy is improved while side effects are reduced. This strategy relies on the identification of the molecular signature of tumor vessels, and development of specific affinity ligands to carry payloads to the tumor (Ruoslahti, 2002). Nanoparticles can be used to further improve drug delivery and efficacy by incorporating multiple functions and increasing the payload (Ruoslahti et al, 2010). However, dysfunctional tumor blood vessels and high interstitial pressure tend to prevent penetration of drugs and nanoparticles into the tumor tissue, limiting the efficacy of the treatments (Jain et al, 1999; Heldin et al, 2004).

Technology has recently been described that provides a way to overcome the limited tissue penetration. CendR peptides induce extravasation and tissue penetration via a mechanism that involves cell internalization (Teesalu et al, 2009; Sugahara et al, 2009, Sugahara et al, 2010). CendR peptides are defined by the presence of the motif R/KXXR/K (X represents any amino acid), which has to be at the C-terminus for the cell- and tissue-penetration activity. The receptor for the CendR motif was shown to be neuropilin 1 (NRP1) (Teesalu et al, 2009).

NRP1 is a modular transmembrane protein previously identified as a receptor for various forms and isoforms of VEGF and members of the class 3 semaphorin family (Takagi et al, 1987; He and Tessier-Lavigne, 1997, Kolodkin et al, 1997; Soker et al, 1998). Neuropilin 2 (NRP2), the second member of the neuropilin family, exhibits sequence and structure homology with NRP1, and shares common ligands NRP-1, $VEGFA_{165}$ among them (Chen et al, 1997; Kolodkin et al, 1997; Glutzman-Poltorak et al, 2000). However, there are also ligands that show selective affinity for one or the other NRP (Chen et al, 1997; Gluzman-Poltorak et al, 2000). Moreover, NRP1 and NRP2 display different expression patterns, with NRP2 (but not NRP1) overexpressed in tumor lymphatics (Caunt et al, 2008). In the CendR pathway, NRP1 appears to be essential for cell internalization and tissue penetration, whereas the role of NRP2 has not been investigated (Teesalu et al, 2009).

iRGD is a tumor penetrating peptide, which contains a RGD motif for recruitment to angiogenic blood vessels and a cryptic CendR motif that is proteolytically unmasked in tumor to trigger extravasation and tissue penetration (Sugahara et al, 2009, Sugahara et al, 2010). As a result of proteolytic cleavage, iRGD loses its affinity for the integrins, acquires NRP1-binding capacity, and induces extravasation (Sugahara et al, 2009). Importantly, co-injected drugs or particles penetrate inside the tumor parenchyma along with iRGD, allowing an increase of treatment efficacy in a number of different cancer models (Sugahara et al, 2010).

LyP-1 is a tumor-homing cyclic nonapeptide (sequence: CGNKRTRGC; SEQ ID NO:10) identified by phage display (Laakkonen et al, 2002). LyP-1 homes to tumor lymphatics, tumor cells, and tumor macrophages by specifically binding to its receptor p32, a mitochondrial protein expressed on the surface of these cells (Laakkonen et al, 2002; Fogal et al, 2008). LyP-1 also homes to atherosclerotic plaques and penetrates into their interior (Hamzah et al, 2011, Uchida et al, 2011). Similar to iRGD, LyP-1 contains a cryptic CendR motif, which is consistent with secondary binding to NRP1 (and perhaps to NRP2 in the lymphatics) and involvement of the CendR pathway. This is also consistent with previous studies showing that LyP-1 is able to extravasate and penetrate the tumor parenchyma (Laakkonen et al, 2002; Von Maltzahn et al, 2008; Karmali et al, 2009). Characterization of the LyP-1 internalization pathway, and of a LyP-1 derivative peptide with an active CendR element for tumor targeting is described herein.

Results in Example 1 show that the tumor homing peptide LyP-1 (Laakkonen et al, 2002) uses the CendR mechanism for cell internalization. Moreover, the results also show a novel tumor homing peptide, tLyP-1, which exhibits enhanced penetration capacity within tumor tissue compared to full-length LyP-1, even when tethered on nanoparticles.

It was discovered that evidence links LyP-1 to the CendR pathway (Teesalu et al, 2009; Sugahara et al, 2009). First, exposure of the CendR motif in LyP-1 triggers binding to the established CendR receptor, NRP1. Second, this binding is specific, and follows the C-end Rule—the CendR motif "KRTR" (amino acids 4-7 of SEQ ID NO:10) must possess a free C-terminus for the binding to occur. Third, when the CendR motif is exposed, the phage is internalized into cells, where it co-localizes with NRP1. Inhibition of the internalization by the prototypic CendR RPARPAR (SEQ ID NO:9) confirmed the involvement of the CendR pathway. These results indicate that the tumor-penetrating properties of LyP-1 depend on the exposure of the cryptic CendR motif.

The previously identified cryptic CendR peptide, iRGD, looses its affinity for the primary tumor receptor αv integrin after proteolytic cleavage, and acquires affinity for NRP1 (Sugahara et al, 2009). Similarly, LyP-1 CendR fragment exhibited a weak affinity for the primary receptor p32, indicating that cryptic CendR peptides follow a general pattern involving loss of affinity for the primary receptor after cleavage, and acquisition of an affinity for NRP1. It was realized that the full inhibition of LyP-1 internalization by the CendR fragment tLyP-1 indicates that internalization occurs through NRP, and not through p32, even though this cannot entirely be ruled out the participation of other binding molecules.

$VEGFA_{165}$, which induces vascular permeability through its interaction with NRP1 (Becker et al, 2005; Mamluk et al, 2005, Acevedo et al, 2008), binds to NRP2 as well (Soker et al, 1998; Glutzman-Poltorak et al, 2000). Interestingly, it was discovered that NRP2 is also a receptor for CendR peptides, although with a lower binding capacity compared to NRP1. Because NRP2 is expressed in tissues and cells where NRP1 is absent (Caunt et al, 2008). An ability to bind NRP2 might be crucial for penetration of CendR peptides in these specific tissues, an example of which may be tumor lymphatics, which express high levels of NRP2 and are a specific target of LyP-1 (Laakknone et al., 2002; 2004). Thus, the distinct properties of various CendR peptides increase the targeting possibilities offered by this technology.

The most significant and surprising discovery was the specific homing of the CendR fragment tLyP-1 to tumors, and its high penetration characteristics. The tLyP-1 peptide alone or conjugated to nanoparticles specifically homed to 3 different types of breast tumors, and spread widely within the tumor tissue. This significantly enhanced penetration compared to LyP-1 nanoparticles, which is likely due to the direct exposure of the CendR motif and the absence of proteolytic activity requirement.

tLyP-1 exhibited more specific homing properties than the prototypic CendR peptide RPARPAR (SEQ ID NO:9). RPARPAR nanoparticles spread widely in all the organs analyzed, whereas tLyP-1 specifically homed to tumors. The lower affinity of tLyP-1 for NRPs favors binding to tissues with the highest local concentration of NRPs: the tumors expressing high levels of NRPs.

The high expression of both NRP1 and NRP2 in tumors (Bagri et al, 2009) allows the use of tLyP-1 in tumor targeting. Homing of tLyP-1 in 3 different kinds of breast tumors is shown in Example 1: 4T1 tumors, which express high levels of both NRPs, MDA-MB-435, which express NRP2, and MDA-MB-231, which express NRP1. Moreover, NRP1 and NRP2 are also present in tumor vessels, with NRP1 being involved in cancer angiogenesis, and NRP2 in cancer lymphangiogenesis (Pan et al, 2007; Liang et al, 2007; Caunt et al, 2008; Dallas et al, 2008). tLyP-1 can thus be used to target a wide variety of solid tumors and to deliver therapeutic or diagnostic agents deep inside the tumor tissue. As a proof of principle, it is shown herein that tLyP-1 was able to carry fluorescein and superparamagnetic iron oxide nanoparticles to the tumor interior. Its strong tumor homing and penetrating properties make tLyP-1 an important addition to the arsenal of targeting agents for drug delivery.

The disclosed tLyP-1 peptides are CendR peptides. CendR peptides are different from the prototypic cell-penetrating peptides (CPPs) in that the cell-penetrating properties of CendR peptides depend on stereo-specific binding to a specific cell surface receptor, whereas both L-amino acid and D-amino acid CPPs are active (Langel, 2007; Meade and Dowdy, 2007). Moreover, the CendR peptides can be specific for a particular pathological lesion (such as tumors, as in the case of tLyP-1 peptides) or an individual tissue.

The ability of compositions to penetrate into the extravascular space is a major factor limiting the targeting efficacy of compositions in vivo. It has been discovered that a truncated form of the LyP-1 homing peptide includes a simple peptide motif, with a C-terminal element as a defining feature, that signals highly efficient internalization of phage and free peptides into cells. This internalization phenomenon has been named the "C-end rule" or "CendR".

Various compositions can be internalized through this mechanism. The CendR pathway can also be used for exit of compositions of interest from the vasculature and their spread into tissue. The C-terminal element can cause spread of compositions from the vasculature (and thus can be spread into tumor tissue from an intravenous injection, for example). CendR elements can also be used to mediate passage of compositions of interest through other CendR-capable membranes, such as mucous membranes and the blood-brain barrier. As used herein, "tissue penetration" and "penetration of tissue" refer to passage into or through a tissue beyond or through the outer or a first layer of cells or through a tissue membrane. Such passage or penetration through tissue (which can also be referred to as extravasation and tissue penetration) can be a function of, for example, cell internalization and passage between cells in the tissue. Throughout this application, when the term "tissue penetration" is used, it is understood that such penetration can also extend to other barriers and CendR-capable membranes found throughout the body, such as the blood brain barrier.

In the case of the disclosed tLyP-1 peptides, the sequence of the peptides provides both homing to tumor vasculature and cell internalization and tissue pentration at the site of accumulation. Unlike the known cell-penetrating peptides, the disclosed tLyP-1 internalizing element is position-dependent—it is inactive when present in positions other than the C-terminus of the peptide.

Co-compositions and cargos of various sizes can be used with the tLyP-1 peptides. Including a tLyP-1 peptide with a drug can result in a higher concentration of the drug in the tumor without affecting its concentration in non-tumor tissues. The disclosed methods and compositions can also result in a broader distribution of the drug within the tumor. As a result, anti-tumor activity can be enhanced. tLyP-1 peptides can be combined with numerous other elements, such as accessory molecules and homing motifs, as well as components to be delivered and internalized, such as co-compositions and cargo compositions.

Penetration into tumor tissue is an issue with all anti-cancer drugs because of the high intra-tumor fluid pressure that forces tissue fluid to flow out of the tumor, which works against diffusion of drugs into the extravascular tumor tissue (Jain et al., 2007). The presumed reasons are that the blood vessels tend to be leaky and the lymphatic vessels are poorly functional in tumors. If a drug were completely tumor-specific and innocuous in normal tissues (and if cost were not an issue), it would be possible to administer so much of that drug that it would overwhelm any barriers to the delivery of sufficient doses to all parts of the tumor. This obviously is not the case with anti-cancer agents; drug toxicity limits the dosing, and tumor penetration is a major obstacle. The disclosed methods and compositions can have the highest impact on drugs that either have penetration problems, or that are effective but highly toxic even at the standard therapeutic doses. Essentially all anti-cancer drugs have one or both of these problems.

It has been discovered that tLyP-1 peptides specifically increase the penetration of drugs into tumors and into other cells and tissues. Disclosed are tumor-homing peptides that specifically increase the penetration of drugs into tumors. These peptides specifically home to tumors, penetrate tissue, and internalize into cells. Drug, fluorophore, nanoparticle, etc., payloads attached to these peptides accumulate in tumors and penetrate deep into the extravascular tumor tissue. However, it has also been discovered that the payload does not need to be coupled to or associated with the tLyP-1 peptide. The free tLyP-1 peptide specifically induces tissue permeability in the tumor, allowing a co-injected drug, nanoparticle, etc., to extravasate and penetrate into tumor tissue. This same effect can be achieved with any cells and tissue with CendR receptors.

Tumor-penetrating tLyP-1 peptides can be used, for example, to augment tumor imaging and tumor treatment with anti-cancer drugs. FDA-approved imaging agents, such as iron oxide nanoparticle MRI contrast agent, can be injected into subjects with a tLyP-1 peptide followed by imaging. Any known or future drug can be used with tLyP-1 peptides to affect and inhibit tumor growth. For example, the co-composition can be any clinically used anti-cancer drugs. Drug accumulation and distribution in tumor tissue, as well as anti-tumor efficacy can be determined using known techniques (examples of such are described herein).

The disclosed enhancement of internalization and tissue penetration has broad application. Using the disclosed tLyP-1 peptides, the effective targeting, delivery, and penetration of any drug, compound or composition can be augmented and enhanced. The effect of tLyP-1 peptides has several significant implications. First, drugs and other compounds and compositions can be delivered to cells and tissues of interest at higher concentrations than is possible in standard therapy. This is a result of the increased internalization and tissue penetration mediated by the tLyP-1 peptide. This is particularly significant because the amount of drug that can be administered is generally limited by side effects. Increasing the drug concentration at the target without increasing the amount of drug administered can thus extend and enhance the effectiveness of any known or future drugs and therapeutics. When using tLyP-1 peptides, the increase in drug concentration only occurs in target cells and tissues and not in non-target tissues. In such cases, the efficacy of the treatment can be increased, while side effects can remain the same. Second, the dose or amount of drug or other compound or composition can be reduced without compromising the efficacy of the treatment. The tLyP-1 peptide would result in the same drug concentration at the target cell or tissue even though the amount of drug administered is less. Third, because the adjuvant tLyP-1 peptide and the drug, imaging agent, or other compound or composition need not be coupled to one another, a validated and approved tLyP-1 peptide can be used to augment any drug, imaging agent, or other compound or composition.

In another example, the tLyP-1 peptides can be used in nanomedicine. One of the main goals of nanomedicine is to design devices that surpass simple drugs by performing multiple functions in diagnosing, monitoring, and treating disease. New technologies can be applied to solve some of the main problems in the medical uses of multifunctional nanoparticles, such as poor penetration into extravascular tissue.

Disclosed are tLyP-1 compositions, tLyP-1 conjugates, tLyP-1 molecules, tLyP-1 proteins, and tLyP-1 peptides. tLyP-1 peptides are the basic feature of tLyP-1 compositions, tLyP-1 conjugates, tLyP-1 molecules, tLyP-1 proteins, and the like. tLyP-1 compositions are any composition, conglomeration, conjugate, molecule, protein, peptide, etc. that comprises a tLyP-1 peptide. tLyP-1 conjugates are associations, whether covalent or non-covalent, of a tLyP-1 peptide and one or more other elements, peptides, proteins, compounds, molecules, agents, compounds, etc. For example, a tLyP-1 conjugate can comprise a tLyP-1 peptide, tLyP-1 protein, tLyP-1 compound, tLyP-1 molecule, etc. tLyP-1 molecules are molecules that comprise a tLyP-1 peptide. For example, a tLyP-1 molecule can comprise a tLyP-1 protein, tLyP-1 peptide, etc. In general, tLyP-1 peptides, tLyP-1 proteins, tLyP-1 molecules, and tLyP-1 conjugates are all forms of tLyP-1 compositions. tLyP-1 compounds, tLyP-1 peptides and tLyP-1 proteins can be forms of tLyP-1 molecules. Unless the context indicates otherwise, reference to a tLyP-1 composition is intended to refer to tLyP-1 compositions, tLyP-1 molecules, tLyP-1 proteins, tLyP-1 peptides, and the like. A tLyP-1 component is any molecule, peptide, protein, compound, conjugate, composition, etc. that comprises a tLyP-1 peptide. Examples of tLyP-1 components include, for example, tLyP-1 compositions, tLyP-1 molecules, tLyP-1 proteins, and tLyP-1 peptides.

tLyP-1 components can comprise one or more tLyP-1 peptides. Where a tLyP-1 element comprises two or more tLyP-1 peptides, it is useful for the tLyP-1 component to be designed to allow some or all of the tLyP-1 peptides to be exposed at the C-terminus of a protein or peptide. This can be accomplished in numerous ways in, for example, conjugates and compositions. This can also be accomplished in, for example, branching peptides and proteins.

Disclosed are peptides that target tumor vasculature, are readily internalized into adjacent cells, and extensively penetrate and invade tumor tissue. The disclosed peptides can also mediate targeting, internalization, and tissue penetration of compounds and compositions coupled to, associated with, conjugated to, or even co-administered with the peptide. Examples of the disclosed peptides include peptides where the C-terminal end of the peptide consists of the amino acid sequence CGNKRTR (SEQ ID NO:4) and peptides consiting of CGNKRTR (SEQ ID NO:4). The disclosed peptides can be used in and with a variety of compositions and methods to, for example, enhancing internalization, penetration, or both of such compositions into or through a cell, tissue, or both. Such compositions and methods are also disclosed herein.

Disclosed are peptides where the C-terminal end of the peptide consists of the amino acid sequence CGNKRTR (SEQ ID NO:4). In some forms, the peptide can be a modified peptide. In some forms, the peptide can be a methylated peptide. In some forms, one or more of the methylated peptide can comprise a methylated amino acid segment. In some forms, the peptide can be N- or C-methylated in at least one position.

tLyP-1 peptides are peptides consiting of or having a C-terminal end with the amino acid sequence CGNKRTR (SEQ ID NO:4). tLyP-1 peptides can be composed of standard amino acids with standard peptide linkages or can be embodied in other than standard amino acids and/or with other than standard peptide linkages. tLyP-1 peptides can include modifications to the peptide, amino acids, and/or linkages. Examples of suitable modifications known to those in the art and are described elsewhere herein.

Variant tLyP-1 peptides can be used in place of or in addition to tLyP-1 peptides. Variant tLyP-1 peptides are not tLyP-1 peptides. Examples of variant tLyP-1 peptides include CGNKRTK/H (SEQ ID NO:13), CGNKRTK (SEQ ID NO:14), CGNKRTH (SEQ ID NO:15), CGNKRTKG (SEQ ID NO:18), CGNRRTR/K/H (SEQ ID NO:19), CGN-RRTR/K (SEQ ID NO:25), CGNRRTR/H (SEQ ID NO:26), CGNRRTK/H (SEQ ID NO:27), CGNRRTR (SEQ ID NO:28), CGNRRTK (SEQ ID NO:29), CGNRRTH (SEQ ID NO:30), CGNRRTKG (SEQ ID NO:31), CGNHRTR/K/H (SEQ ID NO:32), CGNHRTR/K (SEQ ID NO:33), CGNHRTR/H (SEQ ID NO:34), CGNHRTK/H (SEQ ID NO:35), CGNHRTR (SEQ ID NO:36), CGNHRTK (SEQ ID NO:37), CGNHRTH (SEQ ID NO:38), CGNHRTKG (SEQ ID NO:39), CGNR/K/HRTR (SEQ ID NO:40), CGNR/KRTR (SEQ ID NO:41), CGNR/HRTR (SEQ ID NO:42), CGNK/HRTR (SEQ ID NO:43), CGNRRTR (SEQ ID NO:44), CGNKRTR (SEQ ID NO:4), CGNHRTR (SEQ ID NO:36), CGNR/K/HRTK (SEQ ID NO:92), CGNR/KRTK (SEQ ID NO:93), CGNR/HRTK (SEQ ID NO:94), CGNK/HRTK (SEQ ID NO:95), CGNR/K/HRTH (SEQ ID NO:96), CGNR/KRTH (SEQ ID NO:97), CGNR/HRTH (SEQ ID NO:98), CGNK/HRTH (SEQ ID NO:99), CGNR/K/HRTKG (SEQ ID NO:100), CGNR/KRTKG (SEQ ID NO:101), CGNR/HRTKG (SEQ ID NO:102), and CGNK/HRTKG (SEQ ID NO:103).

Disclosed are compositions comprising the disclosed tLyP-1 peptide. In some forms, the composition can further comprise a co-composition, where the peptide and the co-composition are not covalently coupled or non-covalently associated with each other. In some forms, the composition can further comprise a cargo composition, where the peptide and the cargo composition are covalently coupled or non-covalently associated with each other.

In some forms, the peptide can selectively home to a tumor. In some forms, the peptide can selectively home to tumor vasculature. In some forms, the peptide and the co-composition are not bound to each other. In some forms, the co-composition and/or cargo composition can comprise a therapeutic agent. In some forms, the co-composition and/or cargo composition can comprise a detection agent. In some forms, the co-composition and/or cargo composition can comprise a carrier, vehicle, or both. In some forms, the co-composition and/or cargo composition can comprise a therapeutic protein, a therapeutic compound, a therapeutic composition, a cancer chemotherapeutic agent, a toxin, a cytotoxic agent, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, an anti-angiogenic agent, or a combination.

In some forms, the peptide can be comprised in a tLyP-1 composition. In some forms, the tLyP-1 composition can comprise one or more cargo compositions. In some forms, the tLyP-1 composition can comprise one or more homing molecules. In some forms, the peptide can be comprised in a tLyP-1 conjugate. In some forms, the tLyP-1 conjugate can comprise one or more cargo compositions. In some forms, the tLyP-1 conjugate can comprise one or more homing molecules. In some forms, the composition can comprise a plurality of cargo compositions. In some forms, the composition can comprise a plurality of copies of the peptide. In some forms, the composition can comprise a plurality of co-compositions.

In some forms, the composition can further comprise a surface molecule and a plurality of membrane perturbing molecules. In some forms, the composition can further comprise one or more homing molecules, wherein the homing molecules selectively home to tumor vasculature. In some forms, the co-composition can comprise a surface molecule, one or more homing molecules, and a plurality of membrane perturbing molecules, wherein the homing molecules selectively home to tumor vasculature. In some forms, the cargo composition can comprise a surface molecule, one or more homing molecules, and a plurality of membrane perturbing molecules, wherein the homing molecules selectively home to tumor vasculature.

In some forms, one or more of the homing molecules can comprise the amino acid sequence CGKRK (SEQ ID NO:1) or a conservative derivative thereof, the amino acid sequence CRKDKC (SEQ ID NO:2) or a conservative derivative thereof, or a combination. In some forms, one or more of the homing molecules can comprise the amino acid sequence CGKRK (SEQ ID NO:1) or a conservative variant thereof. In some forms, one or more of the homing molecules can comprise the amino acid sequence CGKRK (SEQ ID NO:1). In some forms, all of the one or more homing molecules can comprise the amino acid sequence CGKRK (SEQ ID NO:1) or a conservative derivative thereof, the amino acid sequence CRKDKC (SEQ ID NO:2) or a conservative derivative thereof, or a combination.

In some forms, one or more of the membrane perturbing molecules can comprise the amino acid sequence $_D$(KLAKLAK)$_2$ (SEQ ID NO:3) or a conservative variant thereof, (KLAKLAK)$_2$ (SEQ ID NO:3) or a conservative variant thereof, (KLAKKLA)$_2$ (SEQ ID NO:5) or a conservative variant thereof, (KAAKKAA)$_2$ (SEQ ID NO:6) or a conservative variant thereof, or (KLGKKLG)$_3$ (SEQ ID NO:7) or a conservative variant thereof, or a combination. In some forms, one or more of the membrane perturbing molecules can comprise the amino acid sequence $_D$(KLAKLAK)$_2$ (SEQ ID NO:3), (KLAKLAK)$_2$ (SEQ ID NO:3), (KLAKKLA)$_2$ (SEQ ID NO:5), (KAAKKAA)$_2$ (SEQ ID NO:6), or (KLGKKLG)$_3$ (SEQ ID NO:7), or a combination. In some forms, one or more of the membrane perturbing molecules can comprise the amino acid sequence $_D$(KLAKLAK)$_2$ (SEQ ID NO:3) or a conservative variant thereof. In some forms, one or more of the membrane perturbing molecules can comprise the amino acid sequence $_D$(KLAKLAK)$_2$ (SEQ ID NO:3).

In some forms, one or more of the membrane perturbing molecules can be conjugated to one or more of the homing molecules. In some forms, the homing molecules can be conjugated with the surface molecule. In some forms, the membrane perturbing molecules can be conjugated with the surface molecule. In some forms, one or more of the conjugated homing molecules can be indirectly conjugated to the surface molecule via a linker, one or more of the conjugated membrane perturbing molecules can be indirectly conjugated to the surface molecule via a linker, or both. In some forms, the composition can further comprise a plurality of linkers. In some forms, at least one of the linkers can comprise polyethylene glycol.

In some forms, the composition can bind inside tumor blood vessels. In some forms, the composition can be internalized in cells. In some forms, the composition can penetrate tissue. In some forms, the composition can reduce tumor growth.

In some forms, the surface molecule can comprise a nanoparticle, a nanoworm, an iron oxide nanoworm, an iron oxide nanoparticle, an albumin nanoparticle, a liposome, a micelle, a phospholipid, a polymer, a microparticle, or a fluorocarbon microbubble. In some forms, the composition can comprise at least 100 homing molecules. In some forms, the composition can comprise at least 1000 homing molecules. In some forms, the composition can comprise at least 10,000 homing molecules. In some forms, the composition can comprise at least 100 membrane perturbing molecules. In some forms, the composition can comprise at least 1000 membrane perturbing molecules. In some forms, the composition can comprise at least 10,000 membrane perturbing molecules. In some forms, the composition can comprise at least 100 copies of the peptide. In some forms, the composition can comprise at least 1000 copies of the peptide. In some forms, the composition can comprise at least 10,000 copies of the peptide.

In some forms, the composition, tLyP-1 composition, co-composition, or cargo composition can comprise a plurality of surface molecules, a plurality of homing molecules and a plurality of cargo molecules. In some forms, the composition, tLyP-1 composition, co-composition, or cargo composition can comprise one or more surface molecules, a plurality of homing molecules and a plurality of cargo molecules. In some forms, the composition, tLyP-1 composition, co-composition, or cargo composition can comprise a plurality of surface molecules, one or more homing molecules and a plurality of cargo molecules. In some forms, the composition, tLyP-1 composition, co-composition, or cargo composition can comprise a plurality of surface molecules, a plurality of homing molecules and one or more cargo molecules. In some forms, the composition, tLyP-1 composition, co-composition, or cargo composition can comprise one or more surface molecules, one or more homing molecules and a plurality of cargo molecules. In some forms, the composition, tLyP-1 composition, co-composition, or cargo composition can comprise one or more surface molecules, a plurality of homing molecules and one or more cargo molecules. In some forms, the composition, tLyP-1 composition, co-composition, or cargo composition can comprise a plurality of surface molecules, one or more homing molecules and one or more cargo molecules.

In some forms, the composition, tLyP-1 composition, co-composition, or cargo composition can comprise a surface molecule, a plurality of homing molecules and a plurality of cargo molecules, wherein one or more of the homing molecules and one or more of the cargo molecules are associated with the surface molecule. In some forms, the composition, tLyP-1 composition, co-composition, or cargo composition can comprise a surface molecule, a plurality of homing molecules and a plurality of cargo molecules, wherein a plurality of the plurality of homing molecules and a plurality of the plurality of cargo molecules are associated with the surface molecule. In some forms, the composition, tLyP-1 composition, co-composition, or cargo composition can comprise a surface molecule, a plurality of homing molecules and a plurality of cargo molecules, wherein the homing molecules and the cargo molecules are associated with the surface molecule.

In some forms, the composition, tLyP-1 composition, co-composition, or cargo composition can comprise a surface molecule, wherein the surface molecule is multivalent for homing molecules and cargo molecules. In some forms, the composition, tLyP-1 composition, co-composition, or cargo composition can comprise a surface molecule, wherein the surface molecule is multivalent for homing molecules and comprises one or more cargo molecules. In some forms, the composition, tLyP-1 composition, co-composition, or cargo composition can comprise a surface molecule, wherein the surface molecule is multivalent for cargo molecules and comprises one or more homing molecules. In some forms, the composition, tLyP-1 composition, co-composition, or cargo composition can comprise a surface molecule, wherein the surface molecule is multivalent for conjugates, wherein one or more of the conjugates comprise one or more homing molecules and one or more cargo molecules. In some forms, the composition, tLyP-1 composition, co-composition, or cargo composition can comprise a surface molecule, wherein the surface molecule is multivalent for conjugates, wherein one or more of the conjugates comprise a plurality of homing molecules and a plurality cargo molecules. In some forms, the composition, tLyP-1 composition, co-composition, or cargo composition can comprise a surface molecule, wherein the surface molecule is multivalent for conjugates, wherein one or more of the conjugates comprise a homing molecule and a cargo molecule. In some forms, the composition, tLyP-1 composition, co-composition, or cargo composition can comprise a surface molecule, wherein the surface molecule is multivalent for conjugates, wherein each of the conjugates comprises a plurality of homing molecules and a plurality cargo molecules. In some forms, the composition, tLyP-1 composition, co-composition, or cargo composition can comprise a surface molecule, wherein the surface molecule is multivalent for conjugates, wherein each of the conjugates comprises a homing molecule and a cargo molecule. As used herein, a component that is stated to be "multivalent for" one or more other components refers to a component that has a plurality of the other components associated with, conjugated to and/or covalent coupled to the first component.

In some forms, the composition, tLyP-1 composition, co-composition, or cargo composition can comprise a surface molecule, wherein the surface molecule comprises one or more conjugates, wherein one or more of the conjugates comprise one or more homing molecules and one or more cargo molecules. In some forms, the composition, tLyP-1 composition, co-composition, or cargo composition can comprise a surface molecule, wherein the surface molecule comprises one or more conjugates, wherein one or more of the conjugates comprise a plurality of homing molecules and a plurality cargo molecules. In some forms, the composition, tLyP-1 composition, co-composition, or cargo composition can comprise a surface molecule, wherein the surface molecule comprises one or more conjugates, wherein one or more of the conjugates comprise a homing molecule and a cargo molecule. In some forms, the composition, tLyP-1 composition, co-composition, or cargo composition can comprise a surface molecule, wherein the surface molecule comprises one or more conjugates, wherein each of the conjugates comprises a plurality of homing molecules and a plurality cargo molecules. In some forms, the composition, tLyP-1 composition, co-composition, or cargo composition can comprise a surface molecule, wherein the surface molecule comprises one or more conjugates, wherein each of the conjugates comprises a homing molecule and a cargo molecule.

In some forms, one or more of the membrane perturbing molecules can be conjugated to one or more of the homing molecules. In some forms, one or more of the conjugated membrane perturbing molecules and homing molecules can be covalently coupled. In some forms, one or more of the covalently coupled membrane perturbing molecules and homing molecules can comprise fusion peptides. In some forms, the homing molecules can be conjugated with the surface molecule. In some forms, one or more of the conjugated homing molecules can be directly conjugated to the surface molecule. In some forms, one or more of the conjugated homing molecules can be indirectly conjugated to the surface molecule. In some forms, one or more of the homing molecules can be covalently coupled to the surface molecule. In some forms, one or more of the covalently coupled homing molecules can be directly covalently coupled to the surface molecule. In some forms, one or more of the covalently coupled homing molecules can be indirectly covalently coupled to the surface molecule. In some forms, the membrane perturbing molecules can be conjugated with the surface molecule. In some forms, one or more of the conjugated membrane perturbing molecules are directly conjugated to the surface molecule. In some forms, one or more of the conjugated membrane perturbing molecules can be indirectly conjugated to the surface molecule. In some forms, one or more of the membrane perturbing molecules can be covalently coupled to the surface molecule. In some forms, one or more of the covalently coupled membrane perturbing molecules can be directly covalently coupled to the surface molecule. In some forms, one or more of the covalently coupled membrane perturbing molecules can be indirectly covalently coupled to the surface molecule.

In some forms, the surface molecule can comprise a nanoparticle. In some forms, the surface molecule can comprise a nanoworm. In some forms, the surface molecule can comprise an iron oxide nanoworm. In some forms, the surface molecule can comprise an iron oxide nanoparticle. In some forms, the surface molecule can comprise an albumin nanoparticle. In some forms, the surface molecule can comprise a liposome. In some forms, the surface molecule can comprise a micelle. In some forms, the surface molecule comprises a phospholipid. In some forms, the surface molecule comprises a polymer. In some forms, the surface molecule can comprise a microparticle. In some forms, the surface molecule can comprise a fluorocarbon microbubble.

In some forms, the composition, tLyP-1 composition, co-composition, or cargo composition can comprise at least 100 homing molecules. In some forms, the composition, tLyP-1 composition, co-composition, or cargo composition can comprise at least 1000 homing molecules. In some forms, the composition, tLyP-1 composition, co-composition, or cargo composition can comprise at least 10,000 homing molecules. In some forms, the composition, tLyP-1 composition, co-composition, or cargo composition can comprise at least 100 membrane perturbing molecules. In some forms, the composition, tLyP-1 composition, co-composition, or cargo composition can comprise at least 1000 membrane perturbing molecules. In some forms, the composition, tLyP-1 composition, co-composition, or cargo composition can comprise at least 10,000 membrane perturbing molecules. In some forms, the composition, tLyP-1 composition, co-composition, or cargo composition can comprise at least 100 tLyP-1 peptides. In some forms, the composition, tLyP-1 composition, co-composition, or cargo composition can comprise at least 1000 tLyP-1 peptides. In some forms, the composition, tLyP-1 composition, co-composition, or cargo composition can comprise at least 10,000 tLyP-1 peptides.

In some forms, one or more of the homing molecules can be modified homing molecules. In some forms, one or more of the homing molecules can comprise a methylated homing molecule. In some forms, one or more of the methylated homing molecules can comprise a methylated amino acid segment. In some forms, one or more of the membrane perturbing molecules can be modified membrane perturbing molecules. In some forms, one or more of the membrane perturbing molecules can comprise a methylated membrane perturbing molecule. In some forms, one or more of the methylated membrane perturbing molecules can comprise a methylated amino acid segment. In some forms, the amino acid segment can be N- or C-methylated in at least one position.

In some forms, the composition can further comprise one or more moieties. In some forms, the moieties can be independently selected from the group consisting of, for example, an anti-angiogenic agent, a pro-angiogenic agent, a cancer chemotherapeutic agent, a cytotoxic agent, a polypeptide, a nucleic acid molecule, a small molecule, an image contrast agent, a fluorophore, fluorescein, rhodamine, a radionuclide, indium-111, technetium-99, carbon-11, and carbon-13. In some forms, at least one of the moieties can be a therapeutic agent. In some forms, the therapeutic agent can be Abraxane. In some forms, the therapeutic agent can be paclitaxel. In some forms, the therapeutic agent can be taxol. In some forms, at least one of the moieties can be a detectable agent. In some forms, the detectable agent can be FAM.

In some forms, one or more of the homing molecules can comprise the amino acid sequence CGKRK (SEQ ID NO:1), where one or more of the membrane perturbing molecules can comprise the amino acid sequence $_D$(KLAKLAK)$_2$ (SEQ ID NO:3), where one or more of the homing molecules can be indirectly conjugated to the surface molecule via a linker, and where one or more of the membrane perturbing molecules can be indirectly conjugated to the surface molecule via a linker. In some forms, at least one of the linkers can comprise polyethylene glycol.

Also disclosed are methods of enhancing internalization, penetration, or both of a co-composition into or through a cell, tissue, or both. In some forms, the method can comprising exposing the cell, tissue, or both to the co-composition and a tLyP-1 composition, thereby enhancing internalization, penetration, or both of the co-composition into or through the cell, tissue, or both. The tLyP-1 composition can comprise any of the disclosed tLyP-1 peptides or any of the disclosed compositions that comprise a tLyP-1 peptide. In some forms, the tLyP-1 composition and the co-composition are not covalently coupled or non-covalently associated with each other prior to exposing the cell, tissue, or both.

Also disclosed are methods of enhancing internalization, penetration, or both of a cargo composition into or through a cell, tissue, or both. In some forms, the method can comprise exposing the cell, tissue, or both to the cargo composition and a tLyP-1 composition, thereby enhancing internalization, penetration, or both of the cargo composition into or through the cell, tissue, or both. The tLyP-1 composition can comprise any of the disclosed tLyP-1 peptides or any of the disclosed compositions that comprise a tLyP-1 peptide. In some forms, the tLyP-1 composition and the cargo composition can be covalently coupled or non-covalently associated with each other.

Also disclosed are methods of enhancing internalization, penetration, or both into or through a cell, tissue, or both. In some forms, the method can comprise exposing the cell, tissue, or both to a tLyP-1 composition, thereby enhancing internalization, penetration, or both into or through the cell, tissue, or both. The tLyP-1 composition can comprise any of the disclosed tLyP-1 peptides or any of the disclosed compositions that comprise a tLyP-1 peptide.

In some forms, the cell, tissue, or both can be in a subject. In some forms, the cell, tissue, or both can be exposed to the tLyP-1 composition and the co-composition by administering the tLyP-1 composition and the co-composition to the subject. In some forms, the cell, tissue, or both can be exposed to the tLyP-1 composition and the cargo composition by administering the tLyP-1 composition and the cargo composition to the subject. In some forms, the cell, tissue, or both can be exposed to the tLyP-1 composition by administering the tLyP-1 composition to the subject.

In some forms, the tLyP-1 composition can selectively home to a tumor. In some forms, the tLyP-1 composition can selectively home to tumor vasculature. In some forms, the tLyP-1 composition and the co-composition can be administered to the subject simultaneously. In some forms, the tLyP-1 composition and the co-composition can be administered to the subject in a single composition comprising the tLyP-1 composition and the co-composition. In some forms, the tLyP-1 composition and the co-composition can be administered to the subject in separate compositions. In some forms, the tLyP-1 composition and the co-composition can be administered to the subject at different times. In some forms, the tLyP-1 composition and the co-composition can be administered to the subject in separate compositions. In some forms, the tLyP-1 composition and the co-composition can be administered to the subject by separate routes.

In some forms, the tLyP-1 composition and the co-composition are not bound to each other. In some forms, the tLyP-1 composition, co-composition, and/or cargo composition can comprise a therapeutic agent. In some forms, the tLyP-1 composition, co-composition, and/or cargo composition can comprise a detection agent. In some forms, the tLyP-1 composition, co-composition, and/or cargo composition can comprise a carrier, vehicle, or both. In some forms, the tLyP-1 composition, co-composition, and/or cargo composition can comprise a therapeutic protein, a therapeutic compound, a therapeutic composition, an anti-angiogenic agent, a pro-angiogenic agent, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination.

In some forms, the tLyP-1 composition can comprise one or more accessory molecules. In some forms, the cell, tissue, or both can be exposed to a plurality of homing molecules. In some forms, the cell, tissue, or both can be exposed to a plurality of cargo compositions. In some forms, the cell, tissue, or both can be exposed to a plurality of tLyP-1 compositions. In some forms, the cell, tissue, or both can be exposed to a plurality of co-compositions.

In some forms, the tLyP-1 composition, co-composition, and/or cargo composition can have a therapeutic effect. In some forms, the therapeutic effect can be a slowing in the increase of or a reduction of tumor burden. In some forms, the therapeutic effect can be a slowing of the increase of or reduction of tumor size. In some forms, the subject can have one or more sites to be targeted, where the tLyP-1 composition, co-composition, and/or cargo composition homes to one or more of the sites to be targeted. In some forms, the subject can have a tumor, where the tLyP-1 composition, co-composition, and/or cargo composition has a therapeutic effect on the tumor. In some forms, the tLyP-1 composition, co-composition, and/or cargo composition can penetrate tissue. In some forms, the tLyP-1 composition, co-composition, and/or cargo composition can penetrate tumor tissue.

Multiple different tLyP-1 peptides, tLyP-1 compounds, tLyP-1 conjugates, tLyP-1 compositions, or a combination can be used together. Similarly, multiple different co-compositions, multiple different cargo compositions, or a combination can be used together. Where such multiple different tLyP-1 peptides, tLyP-1 compounds, tLyP-1 conjugates, tLyP-1 compositions, or a combination are used together, they can be used with a single type of co-composition, a single type of cargo composition, multiple different co-compositions, multiple different cargo compositions, or a combination. Similarly, when multiple different co-compositions, multiple different cargo compositions, or a combination can be used together, they can be used with a single type of tLyP-1 peptide, tLyP-1 compound, tLyP-1 conjugate, tLyP-1 composition, or with multiple different tLyP-1 peptides, tLyP-1 compounds, tLyP-1 conjugates, tLyP-1 compositions, or a combination.

For example, a CGNKRTR peptide (SEQ ID NO:4) can be used together with one or multiple different tLyP-1 peptides, tLyP-1 compounds, tLyP-1 conjugates, tLyP-1 compositions, or a combination, one or multiple different co-compositions, multiple different cargo compositions, or a combination, or any combination of these. In such combinations, the CGNKRTR peptide (SEQ ID NO:4) itself can be combined in the same conjugate or composition with one or more cargo compositions, one or more accessory molecules, one or more homing molecules, etc.

The cell, tissue, or both can be exposed to combinations of different tLyP-1 components and combinations of different co-compositions by administering the tLyP-1 components and the co-compositions to the subject. One or more of the tLyP-1 components and one or more of the co-compositions can be administered to the subject simultaneously. One or more of the tLyP-1 components and one or more of the co-compositions can be administered to the subject in one or more single compositions comprising the tLyP-1 component(s) and the co-composition(s). One or more of the tLyP-1 components and one or more of the co-compositions can be administered to the subject in one or more separate compositions. One or more of the tLyP-1 components and one or more of the co-compositions can be administered to the subject at different times. The tLyP-1 composition and the co-composition can be administered to the subject in one or more separate compositions. One or more of the tLyP-1 components and one or more of the co-compositions can be administered to the subject by one or more separate routes. In some forms, the tLyP-1 composition and the co-composition are not bound to each other.

The cell, tissue, or both can be exposed to combinations of different tLyP-1 components and combinations of different cargo compositions by administering the tLyP-1 components and the cargo compositions to the subject. One or more of the tLyP-1 components and one or more of the cargo compositions can be administered to the subject simultaneously. One or more of the tLyP-1 components and one or more of the cargo compositions can be administered to the subject in one or more single compositions comprising the tLyP-1 component(s) and the cargo composition(s). One or more of the tLyP-1 components and one or more of the cargo compositions can be administered to the subject in one or more separate compositions. One or more of the tLyP-1 components and one or more of the cargo compositions can be administered to the subject at different times. The tLyP-1 composition and the cargo composition can be administered to the subject in one or more separate compositions. One or more of the tLyP-1 components and one or more of the cargo compositions can be administered to the subject by one or more separate routes.

The tLyP-1 peptide can be comprised in an amino acid sequence in a protein or peptide. In some forms, the protein or peptide can be internalized into a cell, penetrate tissue, or both when the amino acid sequence is present in the protein or peptide but not when the amino acid sequence is not present in the protein or peptide. In some forms, the protein or peptide can penetrate tissue when the amino acid sequence is present in the protein or peptide but not when the amino acid sequence is not present in the protein or peptide. In some forms, the protein or peptide can be internalized into a cell and penetrate tissue when the amino acid sequence is present in the protein or peptide but not when the amino acid sequence is not present in the protein or peptide. In some forms, the amino acid sequence can be internalized into a cell, penetrate tissue, or both without being associated with the co-composition. In some forms, the amino acid sequence can penetrate tissue without being associated with the co-composition. In some forms, the amino acid sequence can be internalized into a cell and penetrate tissue without being associated with the co-composition. In some forms, the amino acid sequence is the only functional internalization element in the protein or peptide.

In some forms, the internalization, penetration, or both of the co-composition into or through a cell, tissue, or both is enhanced when the cell, tissue, or both is exposed to the tLyP-1 peptide but not when the cell, tissue, or both is not exposed to the tLyP-1 peptide. In some forms, the penetration of the co-composition into or through tissue is enhanced when the tissue is exposed to the tLyP-1 peptide but not when the tissue is not exposed to the tLyP-1 peptide. In some forms, the internalization and penetration of the co-composition into or through a cell and tissue is enhanced when the cell and tissue are exposed to the tLyP-1 peptide but not when the cell and tissue is not exposed to the tLyP-1 peptide. In some forms, the internalization, penetration, or both of the co-composition into or through a cell, tissue, or both is enhanced when the amino acid sequence is present in the protein or peptide but not when the amino acid sequence is not present in the protein or peptide. In some forms, the penetration of the co-composition into or through tissue is enhanced when the amino acid sequence is present in the protein or peptide but not when the amino acid sequence is not present in the protein or peptide. In some forms, the internalization and penetration of the co-composition into or through a cell and tissue is enhanced when the amino acid sequence is present in the protein or peptide but not when the amino acid sequence is not present in the protein or peptide. In some forms, the internalization, penetration, or both of the cargo composition into or through a cell, tissue, or both is enhanced when the cell, tissue, or both is exposed to the tLyP-1 peptide but not when the cell, tissue, or both is not exposed to the tLyP-1 peptide. In some forms, the penetration of the cargo composition into or through tissue is enhanced when the tissue is exposed to the tLyP-1 peptide but not when the tissue is not exposed to the tLyP-1 peptide. In some forms, the internalization and penetration of the cargo composition into or through a cell and tissue is enhanced when the cell and tissue are exposed to the tLyP-1 peptide but not when the cell and tissue is not exposed to the tLyP-1 peptide. In some forms, the internalization, penetration, or both of the cargo composition into or through a cell, tissue, or both is enhanced when the amino acid sequence is present in the protein or peptide but not when the amino acid sequence is not present in the protein or peptide. In some forms, the penetration of the cargo composition into or through tissue is enhanced when the amino acid sequence is present in the protein or peptide but not when the amino acid sequence is not present in the protein or peptide. In some forms, the internalization and penetration of the cargo composition into or through a cell and tissue is enhanced when the amino acid sequence is present in the protein or peptide but not when the amino acid sequence is not present in the protein or peptide.

The tLyP-1 peptide can be associated with one or more accessory molecules. For example, an accessory molecule can be a part of an amino acid sequence, a protein, or a peptide that comprises the tLyP-1 peptide. As another example, the accessory molecule can be covalently coupled or non-covalently associated with the tLyP-1 peptide or an amino acid sequence, a protein, or a peptide that comprises the tLyP-1 peptide. The accessory molecule can be separate from or overlapping with the tLyP-1 peptide. For example, some accessory molecules are amino acid sequences. This can allow the amino acid sequence consisting of the tLyP-1 peptide to overlap the amino acid sequence that consists of the accessory amino acid sequence. Alternatively the accessory peptide can be a separate entity that does not overlap with the tLyP-1 peptide. For example, a HER2 binding peptide, CREKA peptide, NGR peptide, or an RGD peptide that is not a tLyP-1 peptide can consist of amino acid sequence that does not overlap with a tLyP-1 peptide. In some forms, the accessory molecule can comprise a sequence in, for example, a tLyP-1 peptide that binds to a specific receptor distinct from the receptor for the tLyP-1 peptide.

The amino acid sequence can comprise one or more accessory peptides. The protein or peptide can comprise one or more accessory peptides. In some forms, the co-composition does not comprise an accessory molecule. The co-composition can comprise one or more accessory molecules. In some forms, the co-composition does not comprise an accessory peptide. The co-composition can comprise one or more accessory peptides. The co-composition can selectively home to a tumor. In some forms, the co-composition does not selectively home to tumor vasculature. The co-composition can selectively home to tumor vasculature. In some forms, the cargo composition does not comprise an accessory molecule. The cargo composition can comprise one or more accessory molecules. In some forms, the cargo composition does not comprise an accessory peptide. The cargo composition can comprise one or more accessory peptides. The cargo composition can selectively home to a tumor. In some forms, the cargo composition does not selectively home to tumor vasculature. The cargo composition can selectively home to tumor vasculature.

The peptide can be an activatable peptide. The activatable peptide can be a protease-activatable peptide. The tLyP-1 peptide can be an activatable tLyP-1 peptide. The activatable tLyP-1 peptide can be a protease-activatable tLyP-1 peptide. The tLyP-1 peptide can be at the C-terminal end of the protein or peptide. The tLyP-1 conjugate can be an activatable tLyP-1 conjugate. The activatable tLyP-1 conjugate can be a protease-activatable tLyP-1 conjugate. The tLyP-1 conjugate can be at the C-terminal end of the protein or peptide. The tLyP-1 composition can be an activatable tLyP-1 composition. The activatable tLyP-1 composition can be a protease-activatable tLyP-1 composition. The tLyP-1 composition can be at the C-terminal end of the protein or peptide.

The tLyP-1 peptide can be associated with one or more homing molecules. For example, a homing molecule can be a part of an amino acid sequence, a protein, or a peptide that comprises the tLyP-1 peptide. As another example, the homing molecule can be covalently coupled or non-covalently associated with the tLyP-1 peptide or an amino acid sequence, a protein, or a peptide that comprises the tLyP-1 peptide. The homing molecule can be separate from or overlapping with the tLyP-1 peptide. For example, some homing molecules are amino acid sequences. This can allow the amino acid sequence consisting of the tLyP-1 peptide to overlap the amino acid sequence that consists of the homing amino acid sequence. Alternatively the homing peptide can be a separate entity that does not overlap with the tLyP-1 peptide. For example, a HER2 binding peptide, CREKA peptide, NGR peptide, or an RGD peptide that is not a tLyP-1 peptide can consist of amino acid sequence that does not overlap with a tLyP-1 peptide. In some forms, the homing molecule can comprise a sequence in, for example, a peptide that binds to a specific receptor distinct from the receptor for the tLyP-1 peptide.

Many homing molecules and homing peptides home to the vasculature of the target tissue. However, for the sake of convenience homing is referred to in some places herein as homing to the tissue associated with the vasculature to which the homing molecule or homing peptide may actually home. Thus, for example, a homing peptide that homes to tumor vasculature can be referred to herein as homing to tumor tissue or to tumor cells. By including or associating a homing molecule or homing peptide with, for example, a protein, peptide, amino acid sequence, co-composition, or cargo composition, the protein, peptide, amino acid sequence, co-composition, or cargo composition can be targeted or can home to the target of the homing molecule or homing peptide. In this way, the protein, peptide, amino acid sequence, co-composition, or cargo composition, or can be said to home to the target of the homing molecule or homing peptide. For convenience and unless otherwise indicated, reference to homing of a protein, peptide, amino acid sequence, co-composition, cargo composition, etc. is intended to indicate that the protein, peptide, amino acid sequence, co-composition, cargo composition, etc. includes or is associated with an appropriate homing molecule or homing peptide.

The amino acid sequence can be selected for internalization into a cell. The amino acid sequence can be selected for tissue penetration. The amino acid sequence can be selected for internalization into a cell and tissue penetration. The amino acid sequence can comprise one or more homing peptides. The amino acid sequence can comprise a tLyP-1 peptide.

In some forms, the tLyP-1 peptide and the co-composition are not covalently coupled or non-covalently associated with each other. In some forms, the co-composition does not comprise a functional internalization element. The co-composition can comprise a functional internalization element. In some forms, the co-composition does not comprise a homing molecule. The co-composition can comprise one or more homing molecules. In some forms, the co-composition does not comprise a homing peptide. The co-composition can comprise one or more homing peptides. The co-composition can selectively home to a tumor. In some forms, the co-composition does not selectively home to tumor vasculature. The co-composition can selectively home to tumor vasculature.

In some forms, the tLyP-1 peptide and the cargo composition are not covalently coupled or non-covalently associated with each other. In some forms, the cargo composition does not comprise a functional internalization element. The cargo composition can comprise a functional internalization element. In some forms, the cargo composition does not comprise a homing molecule. The cargo composition can comprise one or more homing molecules. In some forms, the cargo composition does not comprise a homing peptide. The cargo composition can comprise one or more homing peptides. The cargo composition can selectively home to a tumor. In some forms, the cargo composition does not selectively home to tumor vasculature. The cargo composition can selectively home to tumor vasculature.

The tLyP-1 peptide can be the only functional internalization element in the tLyP-1 composition, conjugate, molecule, protein, peptide, etc., the tLyP-1 peptide can be the only functional tissue penetration element in the tLyP-1 composition, conjugate, molecule, protein, peptide, etc., or both. The selected amino acid sequence can be the only functional internalization element in the tLyP-1 composition, conjugate, molecule, protein, peptide, etc., the selected amino acid sequence can be the only functional tissue penetration element in the tLtP-1 composition, conjugate, molecule, protein, peptide, etc., or both.

Disclosed herein is a method of forming a tLyP-1 composition, the method comprising selecting an amino acid sequence for internalization into a cell, and causing a tLyP-1 peptide to be covalently coupled to or non-covalently associated with the selected amino acid sequence, wherein the tLyP-1 composition comprises the selected amino acid sequence and the coupled or associated tLyP-1 peptide.

Disclosed is a method of making a tLyP-1 composition comprising: (a) selecting an amino acid sequence for internalization into a cell, (b) causing a tLyP-1 peptide to be covalently coupled to or non-covalently associated with the selected amino acid sequence, wherein the tLyP-1 composition comprises the selected amino acid sequence and the coupled or associated tLyP-1 peptide.

Also disclosed is a method of delivering a co-composition into a cell, the method comprising: exposing the cell to a tLyP-1 composition and the co-composition, wherein the tLyP-1 composition can then enter the cell, thereby delivering the co-composition into the cell.

Also disclosed is a method of causing a co-composition to penetrate tissue, the method comprising: exposing the tissue to a tLyP-1 composition and the co-composition, wherein the tLyP-1 composition can then enter and exit cells in the tissue, thereby causing the co-composition to penetrate the tissue.

Also disclosed is a method of delivering a cargo composition into a cell, the method comprising: exposing the cell to a tLyP-1 composition and the cargo composition, wherein the tLyP-1 composition can then enter the cell, thereby delivering the cargo composition into the cell.

Also disclosed is a method of causing a cargo composition to penetrate tissue, the method comprising: exposing the tissue to a tLyP-1 composition and the cargo composition, wherein the tLyP-1 composition can then enter and exit cells in the tissue, thereby causing the cargo composition to penetrate the tissue.

Also disclosed is a method of delivering a cargo composition into a cell, the method comprising: exposing the cell to a tLyP-1 composition and the cargo composition, wherein the tLyP-1 composition comprises the cargo composition, wherein the tLyP-1 composition can then enter the cell, thereby delivering the cargo composition into the cell.

Also disclosed is a method of causing a cargo composition to penetrate tissue, the method comprising: exposing the tissue to a tLyP-1 composition and the cargo composition, wherein the tLyP-1 composition comprises the cargo composition, wherein the tLyP-1 composition can then enter and exit cells in the tissue, thereby causing the cargo composition to penetrate the tissue.

Further disclosed is a method of delivering a composition into a cell, the method comprising: exposing the cell to the composition and a tLyP-1 composition comprising an activatable tLyP-1 peptide, whereupon a cleaving agent activates the activatable tLyP-1 peptide of the tLyP-1 composition, wherein the tLyP-1 composition can then enter the cell, thereby delivering the composition into the cell.

Further disclosed is a method of causing a composition to penetrate tissue, the method comprising: exposing the tissue to the composition and a tLyP-1 composition comprising an activatable tLyP-1 peptide, whereupon a cleaving agent activates the activatable tLyP-1 peptide of the tLyP-1 composition, wherein the tLyP-1 composition can then enter and pass cells in the tissue, thereby causing the composition to penetrate the tissue.

Further disclosed is a method of delivering a co-composition into a cell, the method comprising: exposing the cell to the co-composition and a tLyP-1 composition comprising an activatable tLyP-1 peptide, whereupon a cleaving agent activates the activatable tLyP-1 peptide of the tLyP-1 composition, wherein the tLyP-1 composition can then enter the cell, thereby delivering the co-composition into the cell.

Further disclosed is a method of causing a co-composition to penetrate tissue, the method comprising: exposing the tissue to the co-composition and a tLyP-1 composition comprising an activatable tLyP-1 peptide, whereupon a cleaving agent activates the activatable tLyP-1 peptide of the tLyP-1 composition, wherein the tLyP-1 composition can then enter and pass cells in the tissue, thereby causing the co-composition to penetrate the tissue.

Further disclosed is a method of delivering a cargo composition into a cell, the method comprising: exposing the cell to the cargo composition and a tLyP-1 composition comprising an activatable tLyP-1 peptide, wherein the tLyP-1 composition comprises the cargo composition, whereupon a cleaving agent activates the activatable tLyP-1 peptide of the tLyP-1 composition, wherein the tLyP-1 composition can then enter the cell, thereby delivering the cargo composition into the cell.

Further disclosed is a method of causing a cargo composition to penetrate tissue, the method comprising: exposing the tissue to the cargo composition and a tLyP-1 composition comprising an activatable tLyP-1 peptide, wherein the tLyP-1 composition comprises the cargo composition, whereupon a cleaving agent activates the activatable tLyP-1 peptide of the tLyP-1 composition, wherein the tLyP-1 composition can then enter and pass cells in the tissue, thereby causing the cargo composition to penetrate the tissue.

Cells that can internalize a tLyP-1 peptide can be identified by (a) exposing a cell to a tLyP-1 peptide; and (b) determining if the tLyP-1 peptide was internalized. The cell can be in an assay, for example. Alternatively, cells that can internalize a tLyP-1 peptide can be identified by detecting or measuring NRP1, NRP2, or both, on the cells. Cells that can internalize an activatable peptide can be identified by (a) exposing a cell to an activatable peptide; (b) determining if the activatable peptide was internalized. The activatable peptide can be unblocked before exposure to the cell, but does not need to be. This can be used to test the blocking ability of the blocker, for example.

Cancer cells, or subjects harboring cancer cells, can be identified as candidates for tLyP-1-based therapy by (a) exposing the cancer cell to a tLyP-1 peptide; and (b) determining if the tLyP-1 peptide was internalized by the cancer cell, wherein an internalized tLyP-1 peptide identifies the cancer cell or the subject as being a candidate for tLyP-1-based therapy. The cell can be in an assay, or can be in a subject, for example. Alternatively, cancer cells that can internalize a tLyP-1 peptide can be identified by detecting or measuring NRP1, NRP2, or both, on the cells. Cancer cells overexpressing NRP1, NRP2, or both are particularly identified as candidates for tLyP-1-based therapy.

Tumors, or subjects harboring a tumor, can be identified as a candidate for tLyP-1-based therapy by (a) exposing tissue from the tumor to a tLyP-1 peptide; and (b) determining if the tLyP-1 peptide passed through the tissue or was internalized by cells in the tissue, wherein a passed-through or internalized tLyP-1 peptide identifies the tumor or the subject as being a candidate for tLyP-1-based therapy. Alternatively, tumors that can internalize a tLyP-1 peptide can be identified by detecting or measuring NRP1, NRP2, or both, on the tumors or cells form the tumors. Tumors overexpressing NRP1, NRP2, or both are particularly identified as candidates for tLyP-1-based therapy.

In some forms, the tLyP-1 peptide and the co-composition are not covalently coupled or non-covalently associated with each other. In some forms, the tLyP-1 conjugate and the co-composition are not covalently coupled or non-covalently associated with each other. In some forms, the tLyP-1 composition and the co-composition are not covalently coupled or non-covalently associated with each other. In some forms, the tLyP-1 peptide and the cargo composition are covalently coupled or non-covalently associated with each other. In some forms, the tLyP-1 conjugate and the cargo composition are covalently coupled or non-covalently associated with each other. In some forms, the tLyP-1 composition and the cargo composition are covalently coupled or non-covalently associated with each other.

Disclosed are compositions comprising a tLyP-1 peptide and a co-composition. Also disclosed are compositions comprising a tLyP-1 conjugate and a co-composition. Also disclosed are compositions comprising a tLyP-1 composition and a co-composition. Disclosed are compositions comprising a tLyP-1 peptide and a co-composition, wherein the tLyP-1 peptide and the co-composition are not covalently coupled or non-covalently associated with each other. Also disclosed are compositions comprising a tLyP-1 conjugate and a co-composition, wherein the tLyP-1 conjugate and the co-composition are not covalently coupled or non-covalently associated with each other. Also disclosed are compositions comprising a tLyP-1 composition and a co-composition, wherein the tLyP-1 composition and the co-composition are not covalently coupled or non-covalently associated with each other.

Disclosed are compositions comprising a tLyP-1 peptide and one or more co-compositions. Also disclosed are compositions comprising a tLyP-1 conjugate and one or more co-composition. Also disclosed are compositions comprising a tLyP-1 composition and one or more co-compositions. Disclosed are compositions comprising a tLyP-1 peptide and one or more co-compositions, wherein the tLyP-1 peptide and at least one of the co-compositions are not covalently coupled or non-covalently associated with each other. Also disclosed are compositions comprising a tLyP-1 conjugate and one or more co-compositions, wherein the tLyP-1 conjugate and at least one of the co-compositions are not covalently coupled or non-covalently associated with each other. Also disclosed are compositions comprising a tLyP-1 composition and one or more co-compositions, wherein the tLyP-1 composition and at least one of the co-compositions are not covalently coupled or non-covalently associated with each other.

Disclosed are compositions comprising a tLyP-1 peptide and a cargo composition. Also disclosed are compositions comprising a tLyP-1 conjugate and a cargo composition. Also disclosed are compositions comprising a tLyP-1 composition and a cargo composition. Disclosed are compositions comprising a tLyP-1 peptide and a cargo composition, wherein the tLyP-1 peptide and the cargo composition are covalently coupled or non-covalently associated with each other. Also disclosed are compositions comprising a tLyP-1 conjugate and a cargo composition, wherein the tLyP-1 conjugate and the cargo composition are covalently coupled or non-covalently associated with each other. Also disclosed are compositions comprising a tLyP-1 composition and a cargo composition, wherein the tLyP-1 composition and the cargo composition are covalently coupled or non-covalently associated with each other.

Disclosed are compositions comprising a tLyP-1 peptide and one or more cargo compositions. Also disclosed are compositions comprising a tLyP-1 conjugate and one or more cargo composition. Also disclosed are compositions comprising a tLyP-1 composition and one or more cargo compositions. Disclosed are compositions comprising a tLyP-1 peptide and one or more cargo compositions, wherein the tLyP-1 peptide and at least one of the cargo compositions are covalently coupled or non-covalently associated with each other. Also disclosed are compositions comprising a tLyP-1 conjugate and one or more cargo compositions, wherein the tLyP-1 conjugate and at least one of the cargo compositions are covalently coupled or non-covalently associated with each other. Also disclosed are compositions comprising a tLyP-1 composition and one or more cargo compositions, wherein the tLyP-1 composition and at least one of the cargo compositions are covalently coupled or non-covalently associated with each other.

Also disclosed are compositions comprising a tLyP-1 peptide, an accessory molecule, and a co-composition, wherein the tLyP-1 peptide and the co-composition are not covalently coupled or non-covalently associated with each other, wherein the tLyP-1 peptide and the accessory molecule are covalently coupled or non-covalently associate with each other. Also disclosed are compositions comprising a tLyP-1 conjugate, an accessory molecule, and a co-composition, wherein the tLyP-1 conjugate and the co-composition are not covalently coupled or non-covalently associated with each other, wherein the tLyP-1 conjugate and the accessory molecule are covalently coupled or non-covalently associate with each other. Also disclosed are compositions comprising a tLyP-1 composition, an accessory molecule, and a co-composition, wherein the tLyP-1 composition and the co-composition are not covalently coupled or non-covalently associated with each other, wherein the tLyP-1 composition and the accessory molecule are covalently coupled or non-covalently associate with each other. Also disclosed are compositions comprising a tLyP-1 peptide, an accessory molecule, and a co-composition, wherein the tLyP-1 peptide and the co-composition are not covalently coupled or non-covalently associated with each other, wherein the tLyP-1 peptide comprises the accessory molecule. Also disclosed are compositions comprising a tLyP-1 conjugate, an accessory molecule, and a co-composition, wherein the tLyP-1 conjugate and the co-composition are not covalently coupled or non-covalently associated with each other, wherein the tLyP-1 conjugate comprises the accessory molecule. Also disclosed are compositions comprising a tLyP-1 composition, an accessory molecule, and a co-composition, wherein the tLyP-1 composition and the co-composition are not covalently coupled or non-covalently associated with each other, wherein the tLyP-1 composition comprises the accessory molecule. In these compositions, the accessory molecule can be or can comprise an accessory peptide. In these compositions, the composition can comprise one or more co-compositions and/or one or more accessory molecules, wherein the tLyP-1 peptide, tLyP-1 conjugate, or tLyP-1 composition and at least one of the co-compositions are not covalently coupled or non-covalently associated with each other, wherein the tLyP-1 peptide, tLyP-1 conjugate, or tLyP-1 composition and at least one of the accessory molecules are covalently coupled or non-covalently associated with each other.

Also disclosed are compositions comprising a tLyP-1 peptide, a homing molecule, and a co-composition, wherein the tLyP-1 peptide and the co-composition are not covalently coupled or non-covalently associated with each other, wherein the tLyP-1 peptide and the homing molecule are covalently coupled or non-covalently associate with each other. Also disclosed are compositions comprising a tLyP-1 conjugate, a homing molecule, and a co-composition, wherein the tLyP-1 conjugate and the co-composition are not covalently coupled or non-covalently associated with each other, wherein the tLyP-1 conjugate and the homing molecule are covalently coupled or non-covalently associate with each other. Also disclosed are compositions comprising a tLyP-1 composition, a homing molecule, and a co-composition, wherein the tLyP-1 composition and the co-composition are not covalently coupled or non-covalently associated with each other, wherein the tLyP-1 composition and the homing molecule are covalently coupled or non-covalently associate with each other. Also disclosed are compositions comprising a tLyP-1 peptide, a homing molecule, and a co-composition, wherein the tLyP-1 peptide and the co-composition are not covalently coupled or non-covalently associated with each other, wherein the tLyP-1 peptide comprises the homing molecule. Also disclosed are compositions comprising a tLyP-1 conjugate, a homing molecule, and a co-composition, wherein the tLyP-1 conjugate and the co-composition are not covalently coupled or non-covalently associated with each other, wherein the tLyP-1 conjugate comprises the homing molecule. Also disclosed are compositions comprising a tLyP-1 composition, a homing molecule, and a co-composition, wherein the tLyP-1 composition and the co-composition are not covalently coupled or non-covalently associated with each other, wherein the tLyP-1 composition comprises the homing molecule. In these compositions, the homing molecule can be or can comprise a homing peptide. In these compositions, the composition can comprise one or more co-compositions and/or one or more homing molecules, wherein the tLyP-1 peptide, tLyP-1 conjugate, or tLyP-1 composition and at least one of the co-compositions are not covalently coupled or non-covalently associated with each other, wherein the tLyP-1 peptide, tLyP-1 conjugate, or tLyP-1 composition and at least one of the homing molecules are covalently coupled or non-covalently associated with each other.

Also disclosed are compositions comprising a tLyP-1 peptide, an accessory molecule, and a cargo composition, wherein the tLyP-1 peptide and the cargo composition are covalently coupled or non-covalently associated with each other, wherein the tLyP-1 peptide and the accessory molecule are covalently coupled or non-covalently associate with each other. Also disclosed are compositions comprising a tLyP-1 conjugate, an accessory molecule, and a cargo composition, wherein the tLyP-1 conjugate and the cargo composition are covalently coupled or non-covalently associated with each other, wherein the tLyP-1 conjugate and the accessory molecule are covalently coupled or non-covalently associate with each other. Also disclosed are compositions comprising a tLyP-1 composition, an accessory molecule, and a cargo composition, wherein the tLyP-1 composition and the cargo composition are covalently coupled or non-covalently associated with each other, wherein the tLyP-1 composition and the accessory molecule are covalently coupled or non-covalently associate with each other. Also disclosed are compositions comprising a tLyP-1 peptide, an accessory molecule, and a cargo composition, wherein the tLyP-1 peptide and the cargo composition are covalently coupled or non-covalently associated with each other, wherein the tLyP-1 peptide comprises the accessory molecule. Also disclosed are compositions comprising a tLyP-1 conjugate, an accessory molecule, and a cargo composition, wherein the tLyP-1 conjugate and the cargo composition are covalently coupled or non-covalently associated with each other, wherein the tLyP-1 conjugate comprises the accessory molecule. Also disclosed are compositions comprising a tLyP-1 composition, an accessory molecule, and a cargo composition, wherein the tLyP-1 composition and the cargo composition are covalently coupled or non-covalently associated with each other, wherein the tLyP-1 composition comprises the accessory molecule. In these compositions, the accessory molecule can be or can comprise an accessory peptide. In these compositions, the composition can comprise one or more cargo compositions and/or one or more accessory molecules, wherein the tLyP-1 peptide, tLyP-1 conjugate, or tLyP-1 composition and at least one of the cargo compositions are covalently coupled or non-covalently associated with each other, wherein the tLyP-1 peptide, tLyP-1 conjugate, or tLyP-1 composition and at least one of the accessory molecules are covalently coupled or non-covalently associated with each other.

Also disclosed are compositions comprising a tLyP-1 peptide, a homing molecule, and a cargo composition, wherein the tLyP-1 peptide and the cargo composition are covalently coupled or non-covalently associated with each other, wherein the tLyP-1 peptide and the homing molecule are covalently coupled or non-covalently associate with each other. Also disclosed are compositions comprising a tLyP-1 conjugate, a homing molecule, and a cargo composition, wherein the tLyP-1 conjugate and the cargo composition are covalently coupled or non-covalently associated with each other, wherein the tLyP-1 conjugate and the homing molecule are covalently coupled or non-covalently associate with each other. Also disclosed are compositions comprising a tLyP-1 composition, a homing molecule, and a cargo composition, wherein the tLyP-1 composition and the cargo composition are covalently coupled or non-covalently associated with each other, wherein the tLyP-1 composition and the homing molecule are covalently coupled or non-covalently associate with each other. Also disclosed are compositions comprising a tLyP-1 peptide, a homing molecule, and a cargo composition, wherein the tLyP-1 peptide and the cargo composition are covalently coupled or non-covalently associated with each other, wherein the tLyP-1 peptide comprises the homing molecule. Also disclosed are compositions comprising a tLyP-1 conjugate, a homing molecule, and a cargo composition, wherein the tLyP-1 conjugate and the cargo composition are covalently coupled or non-covalently associated with each other, wherein the tLyP-1 conjugate comprises the homing molecule. Also disclosed are compositions comprising a tLyP-1 composition, a homing molecule, and a cargo composition, wherein the tLyP-1 composition and the cargo composition are covalently coupled or non-covalently associated with each other, wherein the tLyP-1 composition comprises the homing molecule. In these compositions, the homing molecule can be or can comprise a homing peptide. In these compositions, the composition can comprise one or more cargo compositions and/or one or more homing molecules, wherein the tLyP-1 peptide, tLyP-1 conjugate, or tLyP-1 composition and at least one of the cargo compositions are not covalently coupled or non-covalently associated with each other, wherein the tLyP-1 peptide, tLyP-1 conjugate, or tLyP-1 composition and at least one of the homing molecules are covalently coupled or non-covalently associated with each other.

Also disclosed are compositions comprising a protein or peptide and a co-composition, wherein the protein or peptide comprises a tLyP-1 peptide and an accessory peptide, wherein the tLyP-1 peptide and the co-composition are not covalently coupled or non-covalently associated with each other. Also disclosed are compositions comprising a protein or peptide and a co-composition, wherein the protein or peptide comprises an amino acid sequence, wherein the amino acid sequence comprises a tLyP-1 peptide and an accessory peptide, wherein the tLyP-1 peptide and the co-composition are not covalently coupled or non-covalently associated with each other. In these compositions, the composition can comprise one or more co-compositions and/or one or more accessory peptides, wherein the protein or peptide and at least one of the co-compositions are not covalently coupled or non-covalently associated with each other, wherein the protein or peptide and at least one of the accessory peptides are covalently coupled or non-covalently associated with each other.

Also disclosed are compositions comprising a protein or peptide and a co-composition, wherein the protein or peptide comprises a tLyP-1 peptide and a homing peptide, wherein the tLyP-1 peptide and the co-composition are not covalently coupled or non-covalently associated with each other. Also disclosed are compositions comprising a protein or peptide and a co-composition, wherein the protein or peptide comprises an amino acid sequence, wherein the amino acid sequence comprises a tLyP-1 peptide and a homing peptide, wherein the tLyP-1 peptide and the co-composition are not covalently coupled or non-covalently associated with each other. In these compositions, the composition can comprise one or more co-compositions and/or one or more homing peptides, wherein the protein or peptide and at least one of the co-compositions are not covalently coupled or non-covalently associated with each other, wherein the protein or peptide and at least one of the homing peptides are covalently coupled or non-covalently associated with each other.

Also disclosed are compositions comprising a protein or peptide and a cargo composition, wherein the protein or peptide comprises a tLyP-1 peptide and an accessory peptide, wherein the tLyP-1 peptide and the cargo composition are covalently coupled or non-covalently associated with each other. Also disclosed are compositions comprising a protein or peptide and a cargo composition, wherein the protein or peptide comprises an amino acid sequence, wherein the amino acid sequence comprises a tLyP-1 peptide and an accessory peptide, wherein the tLyP-1 peptide and the cargo composition are covalently coupled or non-covalently associated with each other. In these compositions, the composition can comprise one or more cargo compositions and/or one or more accessory peptides, wherein the protein or peptide and at least one of the cargo compositions are covalently coupled or non-covalently associated with each other, wherein the protein or peptide and at least one of the accessory peptides are covalently coupled or non-covalently associated with each other.

Also disclosed are compositions comprising a protein or peptide and a cargo composition, wherein the protein or peptide comprises a tLyP-1 peptide and a homing peptide, wherein the tLyP-1 peptide and the cargo composition are covalently coupled or non-covalently associated with each other. Also disclosed are compositions comprising a protein or peptide and a cargo composition, wherein the protein or peptide comprises an amino acid sequence, wherein the amino acid sequence comprises a tLyP-1 peptide and a homing peptide, wherein the tLyP-1 peptide and the cargo composition are covalently coupled or non-covalently associated with each other. In these compositions, the composition can comprise one or more cargo compositions and/or one or more homing peptides, wherein the protein or peptide and at least one of the cargo compositions are not covalently coupled or non-covalently associated with each other, wherein the protein or peptide and at least one of the homing peptides are covalently coupled or non-covalently associated with each other.

As used herein, reference to components (such as a tLyP-1 peptide and a co-composition) as being "not covalently coupled" means that the components are not connected via covalent bonds (for example, that the tLyP-1 peptide and the co-composition are not connected via covalent bonds). That is, there is no continuous chain of covalent bonds between, for example, the tLyP-1 peptide and the co-composition. Conversely, reference to components (such as a tLyP-1 peptide and a cargo composition) as being "covalently coupled" means that the components are connected via covalent bonds (for example, that the tLyP-1 peptide and the cargo composition are connected via covalent bonds). That is, there is a continuous chain of covalent bonds between, for example, the tLyP-1 peptide and the cargo composition. Components can be covalently coupled either directly or indirectly. Direct covalent coupling refers to the presence of a covalent bond between atoms of each of the components. Indirect covalent coupling refers to the absence of a covalent bond between atoms of each of the components. That is, some other atom or atoms not belonging to either of the coupled components intervenes between atoms of the components. Both direct and indirect covalent coupling involve a continuous chain of covalent bonds.

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

Reference to components (such as a tLyP-1 peptide and a co-composition) as not being "non-covalently associated" means that there is no direct or indirect non-covalent association between the components. That is, for example, no atom covalently coupled to a tLyP-1 peptide is involved in a non-covalent bond with an atom covalently coupled to a co-composition. Within this meaning, a tLyP-1 peptide and a co-composition can be together in a composition where they are indirectly associated via multiple intervening non-covalent bonds while not being non-covalently associated as that term is defined herein. For example, a tLyP-1 peptide and a co-composition can be mixed together in a carrier where they are not directly non-covalently associated. A tLyP-1 peptide and a co-composition that are referred to as not indirectly non-covalently associated cannot be mixed together in a continuous composition. Reference to components (such as a tLyP-1 peptide and a co-composition) as not being "directly non-covalently associated" means that there is no direct non-covalent association between the components (an indirect non-covalent association may be present). Reference to components (such as a tLyP-1 peptide and a co-composition) as not being "indirectly non-covalently associated" means that there is no direct or indirect non-covalent association between the components.

It is understood that components can be non-covalently associated via multiple chains and paths including both direct and indirect non-covalent associations. For the purposes of these definitions, the presence a single direct non-covalent association makes the association a direct non-covalent association even if there are also indirect non-covalent associations present. Similarly, the presence of a covalent connection between components means the components are covalently coupled even if there are also non-covalent associations present. It is also understood that covalently coupled components that happened to lack any non-covalent association with each other are not considered to fall under the definition of components that are not non-covalently associated.

In some forms, the co-composition does not comprise a functional internalization element. The co-composition can comprise a functional internalization element. In some forms, the co-composition does not comprise a homing molecule. The co-composition can comprise a homing molecule. In some forms, the co-composition does not comprise a homing peptide. The co-composition can comprise a homing peptide. The co-composition can selectively home to a tumor. In some forms, the co-composition does not selectively home to tumor vasculature. The co-composition can selectively home to tumor vasculature. In some forms, the co-composition does not comprise an accessory molecule. The co-composition can comprise an accessory molecule. In some forms, the co-composition does not comprise a accessory peptide. The co-composition can comprise an accessory peptide. The co-composition can selectively home to a tumor.

The tLyP-1 peptide can be associated with one or more accessory molecules. For example, an accessory molecule can be a part of an amino acid sequence, protein, peptide, conjugate, or composition that comprises the tLyP-1 peptide. As another example, the accessory molecule can be covalently coupled or non-covalently associated with the tLyP-1 peptide or an amino acid sequence, protein, peptide, conjugate, or composition that comprises the tLyP-1 peptide. Accessory molecules can be any molecule, compound, component, etc. that has a useful function and that can be used in combination with a tLyP-1 composition, tLyP-1 conjugate, tLyP-1 molecule, tLyP-1 protein, and/or tLyP-1 peptide. Examples of useful accessory molecules include homing molecules, targeting molecules, affinity ligands, cell penetrating molecules, endosomal escape molecules, subcellular targeting molecules, nuclear targeting molecules. Different accessory molecules can have similar or different functions from each other. Accessory molecules having similar functions, different functions, or both, can be associated a tLyP-1 composition, tLyP-1 conjugate, tLyP-1 molecule, tLyP-1 protein, and/or tLyP-1 peptide.

The accessory molecule can be separate from or overlapping with the tLyP-1 peptide. For example, some accessory molecules are amino acid sequences. This can allow the amino acid sequence consisting of the tLyP-1 peptide to overlap the amino acid sequence that consists of the accessory amino acid sequence. For example, iRGD, LyP-1, iNGR, and RGR peptides each contain both an accessory sequence and tLyP-1 sequence overlapping with one another in the peptide. Alternatively the accessory molecule can be a separate entity that does not overlap with the tLyP-1 peptide. For example, a HER2 binding peptide, CREKA peptide, NGR peptide, iNGR, or an RGD peptide that is not a tLyP-1 peptide can consist of amino acid sequence that does not overlap with a tLyP-1 peptide. In some forms, the accessory molecule can comprise a sequence in, for example, a peptide that binds to a specific receptor distinct from the receptor for the tLyP-1 peptide.

The tLyP-1 peptide can be associated with one or more accessory molecules. For example, an accessory molecule can be a part of an amino acid sequence, protein, peptide, conjugate, or composition that comprises the tLyP-1 peptide. As another example, the accessory molecule can be covalently coupled or non-covalently associated with the tLyP-1 peptide or an amino acid sequence, protein, peptide, conjugate, or composition that comprises the tLyP-1 peptide. The tLyP-1 conjugate can be associated with one or more accessory molecules. For example, an accessory molecule can be a part of a conjugate or composition that comprises the tLyP-1 conjugate. As another example, the accessory molecule can be covalently coupled or non-covalently associated with the tLyP-1 conjugate or a conjugate or composition that comprises the tLyP-1 conjugate. The tLyP-1 composition can be associated with one or more accessory molecules. For example, an accessory molecule can be a part of a composition that comprises the tLyP-1 composition. As another example, the accessory molecule can be covalently coupled or non-covalently associated with the tLyP-1 composition or a composition that comprises the tLyP-1 composition.

The amino acid sequence can be associated with one or more accessory molecules. For example, an accessory molecule can be a part of an amino acid sequence, protein, peptide, conjugate, or composition that comprises the amino acid sequence. As another example, the accessory molecule can be covalently coupled or non-covalently associated with the amino acid sequence or an amino acid sequence, protein, peptide, conjugate, or composition that comprises the amino acid sequence. For example, the amino acid sequences can comprise a iRGD peptide, a LyP-1 peptide, a RGR peptide, a HER2 binding peptide, a CREKA peptide, a NGR peptide, iNGR, a RGD peptide that is not a tLyP-1 peptide, or a combination. The amino acid sequence can comprise a CREKA peptide. The protein or peptide can be associated with one or more accessory molecules. For example, an accessory molecule can be a part of a protein, peptide, conjugate, or composition that comprises the peptide. As another example, the accessory molecule can be covalently coupled or non-covalently associated with the peptide or a protein, peptide, conjugate, or composition that comprises the peptide. For example, an accessory molecule can be a part of a protein, conjugate, or composition that comprises the protein. As another example, the accessory molecule can be covalently coupled or non-covalently associated with the protein or a protein, conjugate, or composition that comprises the protein. For example, the protein or peptide can comprise a iRGD peptide, a LyP-1 peptide, a RGR peptide, a HER2 binding peptide, a CREKA peptide, a NGR peptide, iNGR, a RGD peptide that is not a tLyP-1 peptide, or a combination. The conjugate can be associated with one or more accessory molecules. For example, an accessory molecule can be a part of a conjugate or composition that comprises the conjugate. As another example, the accessory molecule can be covalently coupled or non-covalently associated with the conjugate or a conjugate or composition that comprises the conjugate. For example, the conjugate can comprise a iRGD peptide, a LyP-1 peptide, a RGR peptide, a HER2 binding peptide, a CREKA peptide, a NGR peptide, iNGR, a RGD peptide that is not a tLyP-1 peptide, or a combination. The composition can be associated with one or more accessory molecules. For example, an accessory molecule can be a part of a composition that comprises the composition. As another example, the accessory molecule can be covalently coupled or non-covalently associated with the composition or a composition that comprises the composition. For example, the composition can comprise a iRGD peptide, a LyP-1 peptide, a RGR peptide, a HER2 binding peptide, a CREKA peptide, a NGR peptide, iNGR, a RGD peptide that is not a tLyP-1 peptide, or a combination.

The tLyP-1 peptide can be associated with one or more homing molecules. For example, a homing molecule can be a part of an amino acid sequence, protein, peptide, conjugate, or composition that comprises the tLyP-1 peptide. As another example, the homing molecule can be covalently coupled or non-covalently associated with the tLyP-1 peptide or an amino acid sequence, protein, peptide, conjugate, or composition that comprises the tLyP-1 peptide. The homing molecule can be separate from or overlapping with the tLyP-1 peptide. For example, some homing molecules are amino acid sequences. This can allow the amino acid sequence consisting of the tLyP-1 peptide to overlap the amino acid sequence that consists of the homing amino acid sequence. For example, iRGD, LyP-1, iNGR, and RGR peptides each contain both a homing sequence and tLyP-1 sequence overlapping with one another in the peptide. Alternatively the homing molecule can be a separate entity that does not overlap with the tLyP-1 peptide. For example, a HER2 binding peptide, CREKA peptide, NGR peptide, iNGR, or an RGD peptide that is not a tLyP-1 peptide can consist of amino acid sequence that does not overlap with a tLyP-1 peptide. In some forms, the homing molecule can comprise a sequence in, for example, a tLyP-1 peptide that binds to a specific receptor distinct from the receptor for the tLyP-1 peptide.

The tLyP-1 peptide can be associated with one or more homing molecules. For example, a homing molecule can be a part of an amino acid sequence, protein, peptide, conjugate, or composition that comprises the tLyP-1 peptide. As another example, the homing molecule can be covalently coupled or non-covalently associated with the tLyP-1 peptide or an amino acid sequence, protein, peptide, conjugate, or composition that comprises the tLyP-1 peptide. The tLyP-1 conjugate can be associated with one or more homing molecules. For example, a homing molecule can be a part of a conjugate or composition that comprises the tLyP-1 conjugate. As another example, the homing molecule can be covalently coupled or non-covalently associated with the tLyP-1 conjugate or a conjugate or composition that comprises the tLyP-1 conjugate. The tLyP-1 composition can be associated with one or more homing molecules. For example, a homing molecule can be a part of a composition that comprises the tLyP-1 composition. As another example, the homing molecule can be covalently coupled or non-covalently associated with the tLyP-1 composition or a composition that comprises the tLyP-1 composition.

The amino acid sequence can be associated with one or more homing molecules. For example, a homing molecule can be a part of an amino acid sequence, protein, peptide, conjugate, or composition that comprises the amino acid sequence. As another example, the homing molecule can be covalently coupled or non-covalently associated with the amino acid sequence or an amino acid sequence, protein, peptide, conjugate, or composition that comprises the amino acid sequence. For example, the amino acid sequences can comprise a iRGD peptide, a LyP-1 peptide, a RGR peptide, a HER2 binding peptide, a CREKA peptide, a NGR peptide, iNGR, a RGD peptide that is not a tLyP-1 peptide, or a combination. The amino acid sequence can comprise a CREKA peptide. The protein or peptide can be associated with one or more homing molecules. For example, a homing molecule can be a part of a protein, peptide, conjugate, or composition that comprises the peptide. As another example, the homing molecule can be covalently coupled or non-covalently associated with the peptide or a protein, peptide, conjugate, or composition that comprises the peptide. For example, a homing molecule can be a part of a protein, conjugate, or composition that comprises the protein. As another example, the homing molecule can be covalently coupled or non-covalently associated with the protein or a protein, conjugate, or composition that comprises the protein. For example, the protein or peptide can comprise a iRGD peptide, a LyP-1 peptide, a RGR peptide, a HER2 binding peptide, a CREKA peptide, a NGR peptide, iNGR, a RGD peptide that is not a tLyP-1 peptide, or a combination. The protein or peptide can comprise iRGD. The protein or peptide can comprise a LyP-1 peptide. The protein or peptide can comprise iNGR. The protein or peptide can comprise RGR peptide. The protein or peptide can comprise a CREKA peptide. The conjugate can be associated with one or more homing molecules. For example, a homing molecule can be a part of a conjugate or composition that comprises the conjugate. As another example, the homing molecule can be covalently coupled or non-covalently associated with the conjugate or a conjugate or composition that comprises the conjugate. For example, the conjugate can comprise a iRGD peptide, a LyP-1 peptide, a RGR peptide, a HER2 binding peptide, a CREKA peptide, a NGR peptide, iNGR, a RGD peptide that is not a tLyP-1 peptide, or a combination. The conjugate can comprise iRGD. The conjugate can comprise a LyP-1 peptide. The conjugate can comprise iNGR. The conjugate can comprise RGR peptide. The conjugate can comprise a CREKA peptide. The composition can be associated with one or more homing molecules. For example, a homing molecule can be a part of a composition that comprises the composition. As another example, the homing molecule can be covalently coupled or non-covalently associated with the composition or a composition that comprises the composition. For example, the composition can comprise a iRGD peptide, a LyP-1 peptide, a RGR peptide, a HER2 binding peptide, a CREKA peptide, a NGR peptide, iNGR, a RGD peptide that is not a tLyP-1 peptide, or a combination. The composition can comprise iRGD. The composition can comprise a LyP-1 peptide. The composition can comprise iNGR. The composition can comprise RGR peptide. The composition can comprise a CREKA peptide.

The amino acid sequence can be selected for internalization into a cell. The amino acid sequence can be selected for tissue penetration. The amino acid sequence can be selected for internalization into a cell and tissue penetration. The protein or peptide can be selected for internalization into a cell. The protein or peptide can be selected for tissue penetration. The protein or peptide can be selected for internalization into a cell and tissue penetration. The conjugate can be selected for internalization into a cell. The conjugate can be selected for tissue penetration. The conjugate can be selected for internalization into a cell and tissue penetration. The composition can be selected for internalization into a cell. The composition can be selected for tissue penetration. The composition can be selected for internalization into a cell and tissue penetration.

The tLyP-1 peptide, tLyP-1 conjugate, tLyP-1 composition, amino acid sequence, protein or peptide, conjugate, composition, co-composition, cargo composition, or a combination can selectively home to a tumor. The tLyP-1 peptide, tLyP-1 conjugate, tLyP-1 composition, amino acid sequence, protein or peptide, conjugate, composition, co-composition, cargo composition, or a combination can selectively home to tumor vasculature. The tLyP-1 peptide, tLyP-1 conjugate, tLyP-1 composition, amino acid sequence, protein or peptide, conjugate, composition, co-composition, cargo composition, or a combination can selectively home to one or more particular types of tumor. The tLyP-1 peptide, tLyP-1 conjugate, tLyP-1 composition, amino acid sequence, protein or peptide, conjugate, composition, co-composition, cargo composition, or a combination can selectively home to the vasculature of one or more particular types of tumor. The tLyP-1 peptide, tLyP-1 conjugate, tLyP-1 composition, amino acid sequence, protein or peptide, conjugate, composition, co-composition, cargo composition, or a combination can selectively home to one or more particular stages of a tumor or cancer. The tLyP-1 peptide, tLyP-1 conjugate, tLyP-1 composition, amino acid sequence, protein or peptide, conjugate, composition, co-composition, cargo composition, or a combination can selectively home to the vasculature of one or more particular stages of a tumor or cancer. The tLyP-1 peptide, tLyP-1 conjugate, tLyP-1 composition, amino acid sequence, protein or peptide, conjugate, composition, co-composition, cargo composition, or a combination can selectively home to one or more particular stages of one or more particular types of tumor. The tLyP-1 peptide, tLyP-1 conjugate, tLyP-1 composition, amino acid sequence, protein or peptide, conjugate, composition, co-composition, cargo composition, or a combination can selectively home to the vasculature of one or more different stages of one or more particular types of tumor.

The tLyP-1 peptide, tLyP-1 conjugate, tLyP-1 composition, amino acid sequence, protein or peptide, conjugate, composition, co-composition, cargo composition, or a combination can selectively home to lung tissue. The tLyP-1 peptide, tLyP-1 conjugate, tLyP-1 composition, amino acid sequence, protein or peptide, conjugate, composition, co-composition, cargo composition, or a combination can selectively home to lung vasculature. The tLyP-1 peptide, tLyP-1 conjugate, tLyP-1 composition, amino acid sequence, protein or peptide, conjugate, composition, co-composition, cargo composition, or a combination can selectively home to heart tissue. The tLyP-1 peptide, tLyP-1 conjugate, tLyP-1 composition, amino acid sequence, protein or peptide, conjugate, composition, co-composition, cargo composition, or a combination can selectively home to heart vasculature. The tLyP-1 peptide, tLyP-1 conjugate, tLyP-1 composition, amino acid sequence, protein or peptide, conjugate, composition, co-composition, cargo composition, or a combination can selectively home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

tLyP-1 compositions, tLyP-1 conjugates, tLyP-1 molecules, tLyP-1 proteins, and tLyP-1 peptides can be designed and produced in any suitable manner. For example, the tLyP-1 peptide in the disclosed tLyP-1 compositions, tLyP-1 conjugates, tLyP-1 molecules, and tLyP-1 proteins can be designed or produced by selecting an amino acid sequence for internalization into a cell and/or penetration of tissue, wherein the amino acid sequence comprises a C-terminal element, wherein a protein or peptide comprises the selected amino acid sequence, wherein the selected amino acid sequence is at the C-terminal end of the protein or peptide.

The peptide can be an activatable peptide. The activatable peptide can be a protease-activatable peptide. The protease-activatable peptide can be activatable by a serine protease, plasmin, a plasminogen activator, urokinase, a proprotein convertase, a furin, a carboxypeptidase, carboxypeptidase A, a glutamate-specific carboxypeptidase, a proline-specific carboxypeptidase, PSMA, or a combination.

The tLyP-1 peptide can be comprised in an amino acid sequence. The amino acid sequence can be comprised in a protein or peptide. The tLyP-1 peptide can be comprised in a protein or peptide. In some forms, the protein or peptide can be internalized into a cell, penetrate tissue, or both when the amino acid sequence is present in the protein or peptide but not when the amino acid sequence is not present in the protein or peptide. In some forms, the protein or peptide can penetrate tissue when the amino acid sequence is present in the protein or peptide but not when the amino acid sequence is not present in the protein or peptide. In some forms, the protein or peptide can be internalized into a cell and penetrate tissue when the amino acid sequence is present in the protein or peptide but not when the amino acid sequence is not present in the protein or peptide.

In some forms, the amino acid sequence can be internalized into a cell, penetrate tissue, or both without being associated with the co-composition. In some forms, the amino acid sequence can be internalized into a cell, penetrate tissue, or both without being associated with the cargo composition. In some forms, the amino acid sequence can penetrate tissue without being associated with the co-composition. In some forms, the amino acid sequence can penetrate tissue without being associated with the cargo composition. In some forms, the amino acid sequence can be internalized into a cell and penetrate tissue without being associated with the co-composition. In some forms, the amino acid sequence can be internalized into a cell and penetrate tissue without being associated with the cargo composition. In some forms, the amino acid sequence can be the only functional internalization element in the protein or peptide.

In some forms, the internalization, penetration, or both of the co-composition or cargo composition into or through a cell, tissue, or both can be enhanced when the amino acid sequence is present in the protein or peptide but not when the amino acid sequence is not present in the protein or peptide. In some forms, the penetration of the co-composition or cargo composition into or through tissue can be enhanced when the amino acid sequence is present in the protein or peptide but not when the amino acid sequence is not present in the protein or peptide. In some forms, the internalization and penetration of the co-composition or cargo composition into or through a cell and tissue can be enhanced when the amino acid sequence is present in the protein or peptide but not when the amino acid sequence is not present in the protein or peptide. In some forms, the internalization, penetration, or both of the co-composition or cargo composition into or through a cell, tissue, or both can be enhanced when the tLyP-1 peptide is present in the protein or peptide but not when the amino acid sequence is not present in the protein or peptide. In some forms, the penetration of the co-composition or cargo composition into or through tissue can be enhanced when the tLyP-1 peptide is present in the protein or peptide but not when the amino acid sequence is not present in the protein or peptide. In some forms, the internalization and penetration of the co-composition or cargo composition into or through a cell and tissue can be enhanced when the tLyP-1 peptide is present in the protein or peptide but not when the amino acid sequence is not present in the protein or peptide.

The amino acid sequence can be associated with one or more accessory molecules. The protein or peptide can be associated with one or more accessory molecules. One or more of the accessory molecules can be independently a homing molecule, a targeting molecule, an affinity ligand, a cell penetrating peptide, an endosomal escape molecule, a subcellular targeting molecule, a nuclear targeting molecule, or a combination. One or more of the accessory molecules can be homing molecules. One or more of the homing molecules can be independently an RGD peptide, iRGD, LyP-1 peptide, NGR peptide, iNGR, RGR peptide, HER2 binding peptide, or a combination.

The amino acid sequence can be selected for internalization into a cell. The amino acid sequence can be selected for tissue penetration. The amino acid sequence can be selected for internalization into a cell and tissue penetration.

In some forms, the internalization, penetration, or both of the co-composition into or through a cell, tissue, or both can be enhanced when the cell, tissue, or both is exposed to the tLyP-1 peptide but not when the cell, tissue, or both is not exposed to the tLyP-1 peptide. In some forms, the penetration of the co-composition into or through tissue can be enhanced when the tissue is exposed to the tLyP-1 peptide but not when the tissue is not exposed to the tLyP-1 peptide. In some forms, the internalization and penetration of the co-composition into or through a cell and tissue can be enhanced when the cell and tissue are exposed to the tLyP-1 peptide but not when the cell and tissue is not exposed to the tLyP-1 peptide.

The tLyP-1 peptide can be comprised in a tLyP-1 composition. The tLyP-1 composition can comprise one or more accessory molecules. The tLyP-1 composition can comprise one or more cargo compositions. The tLyP-1 composition can comprise one or more homing molecules. The tLyP-1 peptide can be comprised in a tLyP-1 conjugate. The tLyP-1 conjugate can comprise one or more accessory molecules. The tLyP-1 conjugate can comprise one or more cargo compositions. The tLyP-1 conjugate can comprise one or more homing molecules.

The cell, tissue, or both can be exposed to a plurality of accessory molecules. The cell, tissue, or both can be exposed to a plurality of homing molecules. The cell, tissue, or both can be exposed to a plurality of cargo compositions. The cell, tissue, or both can be exposed to a plurality of tLyP-1 peptides. The cell, tissue, or both can be exposed to a plurality of co-compositions.

As used herein, "selecting an amino acid sequence for internalization into a cell" refers to selecting, identifying designing or otherwise categorizing an amino acid sequence with the specific intention of obtaining entry into a cell of a protein or peptide that is comprised of the amino acid sequence. Thus, for example, selecting an amino acid sequence for some purpose or capability other than obtaining entry into a cell of a protein or peptide that is comprised of the amino acid sequence and in the absence of an intention of obtaining entry into a cell of a protein or peptide that is comprised of the amino acid sequence does not constitute "selecting an amino acid sequence for internalization into a cell." Selecting an amino acid sequence for some purpose or capability as well as for obtaining entry into a cell of a protein or peptide that is comprised of the amino acid sequence does constitute "selecting an amino acid sequence for internalization into a cell." Thus, the presence of additional goals or purposes does not alter that selection of an amino acid sequence at least with the specific intention of obtaining entry into a cell of a protein or peptide that is comprised of the amino acid sequence constitutes "selecting an amino acid sequence for internalization into a cell."

As used herein, "selecting an amino acid sequence for penetration of tissue" refers to selecting, identifying designing or otherwise categorizing an amino acid sequence with the specific intention of obtaining entry into tissue (that is, tissue penetration) of a protein or peptide that is comprised of the amino acid sequence. Thus, for example, selecting an amino acid sequence for some purpose or capability other than obtaining entry into tissue of a protein or peptide that is comprised of the amino acid sequence and in the absence of an intention of obtaining entry into tissue of a protein or peptide that is comprised of the amino acid sequence does not constitute "selecting an amino acid sequence for penetration of tissue." Selecting an amino acid sequence for some purpose or capability as well as for obtaining entry into tissue of a protein or peptide that is comprised of the amino acid sequence does constitute "selecting an amino acid sequence for penetration of tissue." Thus, the presence of additional goals or purposes does not alter that selection of an amino acid sequence at least with the specific intention of obtaining entry into tissue of a protein or peptide that is comprised of the amino acid sequence constitutes "selecting an amino acid sequence for penetration of tissue."

As used herein, "selecting an amino acid sequence for internalization into a cell and/or penetration of tissue" refers to selecting, identifying designing or otherwise categorizing an amino acid sequence with the specific intention of obtaining entry into either or both a cell and tissue of a protein or peptide that is comprised of the amino acid sequence. Thus, for example, selecting an amino acid sequence for some purpose or capability other than obtaining entry into a cell, tissue, or both of a protein or peptide that is comprised of the amino acid sequence and in the absence of an intention of obtaining entry into a cell, tissue, or both of a protein or peptide that is comprised of the amino acid sequence does not constitute "selecting an amino acid sequence for internalization into a cell and/or penetration of tissue." Selecting an amino acid sequence for some purpose or capability as well as for obtaining entry into either or both a cell and tissue of a protein or peptide that is comprised of the amino acid sequence does constitute "selecting an amino acid sequence for internalization into a cell and/or penetration of tissue." Thus, the presence of additional goals or purposes does not alter that selection of an amino acid sequence at least with the specific intention of obtaining entry into a cell, tissue, or both of a protein or peptide that is comprised of the amino acid sequence constitutes "selecting an amino acid sequence for internalization into a cell and/or penetration of tissue."

As used herein, unless the context indicates otherwise, "selecting a co-composition for internalization into a cell" refers to selecting, identifying designing or otherwise categorizing a co-composition and a tLyP-1 composition, tLyP-1 conjugate, tLyP-1 molecule, tLyP-1 protein, or tLyP-1 peptide with the specific intention of obtaining entry into a cell of both the co-composition and the tLyP-1 composition, tLyP-1 conjugate, tLyP-1 molecule, tLyP-1 protein, or tLyP-1 peptide. Thus, for example, selecting a co-composition for some purpose or capability other than obtaining entry into a cell in combination with entry of a selected tLyP-1 composition, tLyP-1 conjugate, tLyP-1 molecule, tLyP-1 protein, or tLyP-1 peptide and in the absence of an intention of obtaining entry into a cell of both the co-composition and the tLyP-1 composition, tLyP-1 conjugate, tLyP-1 molecule, tLyP-1 protein, or tLyP-1 peptide does not constitute "selecting co-composition for internalization into a cell." Selecting a co-composition for some purpose or capability as well as for obtaining entry into a cell of the co-composition does constitute "selecting co-composition for internalization into a cell." Thus, the presence of additional goals or purposes does not alter that selection of a co-composition at least with the specific intention of obtaining entry into a cell of a co-composition constitutes "selecting a co-composition for internalization into a cell."

As used herein, unless the context indicates otherwise, "selecting a co-composition for penetration of tissue" refers to selecting, identifying designing or otherwise categorizing a co-composition and a tLyP-1 composition, tLyP-1 conjugate, tLyP-1 molecule, tLyP-1 protein, or tLyP-1 peptide with the specific intention of obtaining entry into tissue (that is, tissue penetration) of both the co-composition and the tLyP-1 composition, tLyP-1 conjugate, tLyP-1 molecule, tLyP-1 protein, or tLyP-1 peptide. Thus, for example, selecting a co-composition for some purpose or capability other than obtaining entry into tissue in combination with entry of a selected tLyP-1 composition, tLyP-1 conjugate, tLyP-1 molecule, tLyP-1 protein, or tLyP-1 peptide and in the absence of an intention of obtaining entry into tissue of both the co-composition and the tLyP-1 composition, tLyP-1 conjugate, tLyP-1 molecule, tLyP-1 protein, or tLyP-1 peptide does not constitute "selecting co-composition for penetration of tissue." Selecting a co-composition for some purpose or capability as well as for obtaining entry into tissue of the co-composition does constitute "selecting co-composition for penetration of tissue." Thus, the presence of additional goals or purposes does not alter that selection of a co-composition at least with the specific intention of obtaining entry into tissue of a co-composition constitutes "selecting a co-composition for penetration of tissue."

As used herein, unless the context indicates otherwise, "selecting a co-composition for internalization into a cell and/or penetration of tissue" refers to selecting, identifying designing or otherwise categorizing a co-composition and a tLyP-1 composition, tLyP-1 conjugate, tLyP-1 molecule, tLyP-1 protein, or tLyP-1 peptide with the specific intention of obtaining entry into either or both a cell and tissue of both the co-composition and the tLyP-1 composition, tLyP-1 conjugate, tLyP-1 molecule, tLyP-1 protein, or tLyP-1 peptide. Thus, for example, selecting a co-composition for some purpose or capability other than obtaining entry into either or both a cell and tissue in combination with entry of a selected tLyP-1 composition, tLyP-1 conjugate, tLyP-1 molecule, tLyP-1 protein, or tLyP-1 peptide and in the absence of an intention of obtaining entry into either or both a cell and tissue of both the co-composition and the tLyP-1 composition, tLyP-1 conjugate, tLyP-1 molecule, tLyP-1 protein, or tLyP-1 peptide does not constitute "selecting co-composition for internalization into a cell and/or penetration of tissue." Selecting a co-composition for some purpose or capability as well as for obtaining entry into either or both a cell and tissue of the co-composition does constitute "selecting co-composition for internalization into a cell and/or penetration of tissue." Thus, the presence of additional goals or purposes does not alter that selection of a co-composition at least with the specific intention of obtaining entry into either or both a cell and tissue of a co-composition constitutes "selecting a co-composition for internalization into a cell and/or penetration of tissue."

As used herein, unless the context indicates otherwise, "selecting a cargo composition for internalization into a cell" refers to selecting, identifying designing or otherwise categorizing a cargo composition and a tLyP-1 composition, tLyP-1 conjugate, tLyP-1 molecule, tLyP-1 protein, or tLyP-1 peptide with the specific intention of obtaining entry into a cell of both the cargo composition and the tLyP-1 composition, tLyP-1 conjugate, tLyP-1 molecule, tLyP-1 protein, or tLyP-1 peptide. Thus, for example, selecting a cargo composition for some purpose or capability other than obtaining entry into a cell in combination with entry of a selected tLyP-1 composition, tLyP-1 conjugate, tLyP-1 molecule, tLyP-1 protein, or tLyP-1 peptide and in the absence of an intention of obtaining entry into a cell of both the cargo composition and the tLyP-1 composition, tLyP-1 conjugate, tLyP-1 molecule, tLyP-1 protein, or tLyP-1 peptide does not constitute "selecting cargo composition for internalization into a cell." Selecting a cargo composition for some purpose or capability as well as for obtaining entry into a cell of the cargo composition does constitute "selecting cargo composition for internalization into a cell." Thus, the presence of additional goals or purposes does not alter that selection of a cargo composition at least with the specific intention of obtaining entry into a cell of a cargo composition constitutes "selecting a cargo composition for internalization into a cell."

As used herein, unless the context indicates otherwise, "selecting a cargo composition for penetration of tissue" refers to selecting, identifying designing or otherwise categorizing a cargo composition and a tLyP-1 composition, tLyP-1 conjugate, tLyP-1 molecule, tLyP-1 protein, or tLyP-1 peptide with the specific intention of obtaining entry into tissue (that is, tissue penetration) of both the cargo composition and the tLyP-1 composition, tLyP-1 conjugate, tLyP-1 molecule, tLyP-1 protein, or tLyP-1 peptide. Thus, for example, selecting a cargo composition for some purpose or capability other than obtaining entry into tissue in combination with entry of a selected tLyP-1 composition, tLyP-1 conjugate, tLyP-1 molecule, tLyP-1 protein, or tLyP-1 peptide and in the absence of an intention of obtaining entry into tissue of both the cargo composition and the tLyP-1 composition, tLyP-1 conjugate, tLyP-1 molecule, tLyP-1 protein, or tLyP-1 peptide does not constitute "selecting cargo composition for penetration of tissue." Selecting a cargo composition for some purpose or capability as well as for obtaining entry into tissue of the cargo composition does constitute "selecting cargo composition for penetration of tissue." Thus, the presence of additional goals or purposes does not alter that selection of a cargo composition at least with the specific intention of obtaining entry into tissue of a cargo composition constitutes "selecting a cargo composition for penetration of tissue."

As used herein, unless the context indicates otherwise, "selecting a cargo composition for internalization into a cell and/or penetration of tissue" refers to selecting, identifying designing or otherwise categorizing a cargo composition and a tLyP-1 composition, tLyP-1 conjugate, tLyP-1 molecule, tLyP-1 protein, or tLyP-1 peptide with the specific intention of obtaining entry into either or both a cell and tissue of both the cargo composition and the tLyP-1 composition, tLyP-1 conjugate, tLyP-1 molecule, tLyP-1 protein, or tLyP-1 peptide. Thus, for example, selecting a cargo composition for some purpose or capability other than obtaining entry into either or both a cell and tissue in combination with entry of a selected tLyP-1 composition, tLyP-1 conjugate, tLyP-1 molecule, tLyP-1 protein, or tLyP-1 peptide and in the absence of an intention of obtaining entry into either or both a cell and tissue of both the cargo composition and the tLyP-1 composition, tLyP-1 conjugate, tLyP-1 molecule, tLyP-1 protein, or tLyP-1 peptide does not constitute "selecting cargo composition for internalization into a cell and/or penetration of tissue." Selecting a cargo composition for some purpose or capability as well as for obtaining entry into either or both a cell and tissue of the cargo composition does constitute "selecting cargo composition for internalization into a cell and/or penetration of tissue." Thus, the presence of additional goals or purposes does not alter that selection of a cargo composition at least with the specific intention of obtaining entry into either or both a cell and tissue of a cargo composition constitutes "selecting a cargo composition for internalization into a cell and/or penetration of tissue."

As used herein, "causing a compound or composition to be covalently coupled or non-covalently associated" with something else refers to any action that results in a compound or composition that is not covalently coupled or non-covalently associated with the something else becoming or coming into the state of being covalently coupled or non-covalently associated with the something else. As an example, covalently coupling a homing molecule to a tLyP-1 peptide constitutes "causing a homing molecule to be covalently coupled or non-covalently associated" with the tLyP-1 peptide. As another example, a tLyP-1 peptide that starts as a nonexistent concept and then is synthesized as part of a composition that includes the thing to which the tLyP-1 peptide is to be coupled or associated constitutes "causing a tLyP-1 peptide to be covalently coupled or non-covalently associated" with the thing. For example, synthesis of a peptide that includes both an amino acid sequence of interest and an amino acid sequence comprising a C-terminal element constitutes causing the amino acid sequence of interest to be covalently coupled or non-covalently associated with the amino acid sequence comprising a C-terminal element. However, and in general, synthesis of a protein or peptide that naturally includes both the amino acid sequence of interest and an amino acid sequence comprising a C-terminal element can be excluded as a process of "causing the amino acid sequence of interest to be covalently coupled or non-covalently associated" with the amino acid sequence comprising a C-terminal element.

As used herein, "causing a co-composition to be covalently coupled or non-covalently associated" with something else refers to any action that results in a co-composition that is not and the something else becoming or coming into the state of being and the something else. More clearly, "causing a co-composition to be covalently coupled or non-covalently associated" with something else refers to any action that results in a co-composition and the something else becoming or coming into the state of being covalently coupled or non-covalently associated. As an example, covalently coupling a co-composition to another co-composition constitutes "causing a co-composition to be covalently coupled or non-covalently associated" with the other co-composition. As another example, a co-composition that starts as a nonexistent concept and then is synthesized as part of a composition that includes the thing to which the co-composition is to be coupled or associated constitutes "causing a co-composition to be covalently coupled or non-covalently associated" with the thing.

As used herein, "causing a cargo composition to be covalently coupled or non-covalently associated" with something else refers to any action that results in a cargo composition that is not and the something else becoming or coming into the state of being and the something else. More clearly, "causing a cargo composition to be covalently coupled or non-covalently associated" with something else refers to any action that results in a cargo composition and the something else becoming or coming into the state of being covalently coupled or non-covalently associated. As an example, covalently coupling a cargo composition to another cargo composition constitutes "causing a cargo composition to be covalently coupled or non-covalently associated" with the other cargo composition. As another example, a cargo composition that starts as a nonexistent concept and then is synthesized as part of a composition that includes the thing to which the cargo composition is to be coupled or associated constitutes "causing a cargo composition to be covalently coupled or non-covalently associated" with the thing.

tLyP-1 peptides can be composed of, for example, amino acids, amino acid analogs, peptide analogs, amino acid mimetics, peptide mimetics, etc. Although structures, design, etc. of tLyP-1 peptides is described herein in terms of amino acids and peptides composed of amino acids for convenience, it is understood that analogous analogs, mimetics, modified forms, etc. of amino acids and peptides can also be used as tLyP-1 peptides and designed using similar principles.

Any component, such as the components disclosed herein, can overlap, be adjacent to, and/or be upstream, downstream, or both of a peptide, such as a tLyP-1 peptide. Examples of such components include accessory molecules, homing molecules, protease cleavage sites, etc. It is useful to have some components coupled to or associated with a peptide, such as a tLyP-1 peptide to be downstream (C-terminal) of the peptide. For example, activatable peptide having an accessory protein or a homing peptide downstream of the peptide (and thus downstream from the cleavage site for activation) will be separated from the peptide when it is activated. As another example, activatable peptides having an accessory molecule or a homing molecule downstream of the peptide (and thus downstream from the cleavage site for activation) will be separated from the peptide when it is activated. This can have some advantages such as making the peptide function more efficient or reducing the chance for extraneous effects of the eliminated component.

As used herein, "activatable peptide" refers to a peptide, such as a tLyP-1 peptide, having a molecule, moiety, nanoparticle, compound or other composition covalently coupled to the peptide, such as to the terminal carboxyl group of the peptide, where the molecule, moiety, nanoparticle, compound or other composition can block internalization and/or tissue penetration of the tLyP-1 composition, conjugate, molecule, protein, peptide, etc. and where the molecule, moiety, nanoparticle, compound or other composition can be removed (to expose the terminal carboxy group of the peptide, for example). For example, the activatable peptide can be on the C-terminal end of the protein or peptide, and can prevent the peptide from being internalized and/or from penetrating tissue. The molecule, nanoparticle, moiety, compound or other composition covalently coupled to the peptide can be referred to as the "blocking group." For example, the blocking group can be coupled to the terminal carboxyl group of the C-terminal arginine of the tLyP-1 peptide, to the C-terminal amino acid of the tLyP-1 peptide, or to an amino acid of the tLyP-1 peptide other than the C-terminal amino acid. The blocking group can also be coupled, or associated with a part of a tLyP-1 composition, conjugate, molecule, protein, peptide, etc. other than the tLyP-1 peptide so long as it can prevent the tLyP-1 peptide from being internalized and/or from penetrating tissue. A tLyP-1 composition comprising an activatable peptide, such as an activatable tLyP-1 peptide, can be referred to as an activatable tLyP-1 composition. A tLyP-1 molecule comprising an activatable peptide, such as an activatable tLyP-1 peptide, can be referred to as an activatable tLyP-1 molecule. A tLyP-1 conjugate comprising an activatable peptide, such as an activatable tLyP-1 peptide, can be referred to as an activatable tLyP-1 conjugate. A tLyP-1 protein comprising an activatable peptide, such as an activatable tLyP-1 peptide, can be referred to as an activatable tLyP-1 protein. A tLyP-1 peptide comprising an activatable peptide can be referred to as an activatable tLyP-1 peptide. The blocking group can comprise or consist of an amino acid or an amino acid sequence.

An activatable peptide, such as an activatable tLyP-1 peptide, can be blocked from internalization into a cell, from tissue penetration, or both. Generally, an activatable peptide, such as an activatable tLyP-1 peptide, will be blocked from both internalization into a cell and penetration of tissue. Such activatable peptides can be referred to as activatable internalization and penetrating peptides. However, some activatable peptides could be blocked only from tissue penetration or only from internalization into a cell. Such activatable pwprides can be referred to as activatable internalization peptides (for peptides that are blocked only from internalization into a cell) or as activatable penetrating peptides (for peptides that are blocked only from penetration of tissue). Generally, internalization peptides that are activatable will be activatable internalization peptides. Similarly, penetrating peptides that are activatable generally will be activatable penetrating peptides. Internalization and penetrating peptides that are activatable will be activatable internalization and penetrating peptides. Removal of the blocking group will allow the peptide to be internalized into a cell, penetrate tissue, or both.

The cleavable bond of an activatable peptide, such as an activatable tLyP-1 peptide, can be cleaved in any suitable way. For example, the cleavable bond can be cleaved enzymatically or non-enzymatically. For enzymatic cleavage, the cleaving enzyme can be supplied or can be present at a site where the peptide is delivered, homes, travels or accumulates. For example, the enzyme can be present in proximity to a cell to which the peptide is delivered, homes, travels, or accumulates. For non-enzymatic cleavage, the peptide can be brought into contact with a cleaving agent, can be placed in cleaving conditions, or both. A cleaving agent is any substance that can mediate or stimulate cleavage of the cleavable bond. A non-enzymatic cleaving agent is any cleaving agent except enzymes. Cleaving conditions can be any solution or environmental conditions that can mediate or stimulate cleavage of the cleavable bond. For example, some labile bonds can be cleaved in acid conditions, alkaline conditions, in the presence of a reactive group, etc. Non-enzymatic cleaving conditions are any cleaving conditions except the presence of enzymes. Non-agent cleaving conditions are any cleaving conditions except the presence of cleaving agents.

Activatable peptides, such as an activatable tLyP-1 peptides can be activatable in broad or narrow circumstances. Generally, activatable peptides are activatable relative to a specific agent or group of agents that can activate the peptides. Thus, for example, a particular activatable peptide may only be activatable by certain proteases. Such a peptide can be referred to as an activatable peptide but can also be referred to as being activatable by the particular proteases.

A "protease-activatable peptide" (or "protease-activated peptide") refers to an activatable peptide where the blocking group is coupled to the peptide via a peptide bond and where the peptide bond can be cleaved by a protease. Cleavage of this peptide bond in a protease-activatable peptide makes the peptide capable of internalization into a cell and/or of tissue penetration. In one example, the blocking group can be coupled to the CendR element via a cleavable or labile bond. The cleavable bond can be cleaved by, for example, an enzyme or a chemical compound. Cleavage or 'labilization' of the bond in an activatable peptide makes the peptide capable of internalization into a cell and/or of tissue penetration. Such cleavage or 'labilization' can be referred to as activation of the peptide. A protease-activatable peptide is a form of activatable peptide. The amino acids of an activatable tLyP-1 peptide, can be selected for specific purposes. For example, the amino acids following the end of tLyP-1 sequence can be chosen to form all or a portion of a protease recognition sequence. This would be useful, for example, to specify or enable cleavage of a peptide having the tLyP-1 peptide that is activated by cleavage following the end of the tLyP-1 sequence. Examples of such amino acid choices are shown in Tables 1 and 2 of U.S. Patent Application Publication No. 2010-0322862. Protease cleavage sites can be predicted based on knowledge developed and known to those of skill in the art. For example, prediction of cleavage can be assessed at the website cbs.dtu.dk/services/ProP/. A useful class of peptides can consist of unblocked peptides and activatable peptides, which class excludes blocked peptides that are not activatable.

Useful proteases include enzymes that cleave on the C terminal side of basic residues (the C terminal residue of tLyP-1 peptides is a basic residue) and enzymes that recognize sequence on the C terminal side of their cleavage site (thus allowing free choice of the C terminal sequence of the cleavage product). Examples of useful proteases include, for example, serine proteases (including, for example, plasmin and plasminogen activators), urokinase, proprotein convertases (see, for example, Duckert et al., Prediction of proprotein convertase cleavage sites Protein engineering Design and Selection 17(1):107-112 (2004)), furins, and carboxypeptidases, such as carboxypeptidase A (amino acids with aromatic or branched hydrocarbon side chains), glutamate-specific carboxypeptidase, proline-specific carboxypeptidase, and PSMA. Serine proteases are particularly useful for CendR elements and CendR compositions targeted to cancer cells and tumors. Examples of enzymes that cleave on the C terminal side of basic residues include Arg-C protease (which cleaves on the C terminal side of arginine residues; Keil, Specificity of Proteolysis (Springer-Verlag, Berlin-Heidelberg-New York (1992)), clostripain (which cleaves on the C terminal side of arginine residues; Keil, 1992), enterokinase (which cleaves after the sequence -Asp-Asp-Asp-Asp-Lys-; SEQ ID NO:22), Factor Xa (which cleaves after the sequence -Gly-Arg-; Fujikawa et al., Activation of bovine factor X (Stuart factor): conversion of factor Xa alpha to factor Xa beta, Proc. Natl. Acad. Sci. 72: 3359-3363 (1975)), Lys-C (which cleaves on the C terminal side of lysine residues; Keil, 1992), thrombin (which cleaves on the C terminal side of arginine residues; Keil, 1992), trypsin (which cleaves on the C terminal side of arginine and lysine residues; Keil, 1992), serine proteases, proprotein convertases (such as PC1, PC2, PC3, PC4, PC5, PC6, PC7, PC8, furin, Pace, PACE4, Site 1 protease, SIP, SKI, NARC-1, PCSK1, PCSK2, PCSK3, PCSK4, PCSK5, PCSK6, PCSK7, PCSK8, and PCSK9), plasmin, and plasminogen activators. Examples of enzymes that recognize sequence on the C terminal side of their cleavage site include Asp-N endopeptidase (which cleaves on the N terminal side of aspartic acid; Keil, 1992) and carboxypeptidases such as carboxypeptidase A (which cleaves C-terminal residues except proline, lysine and arginine).

Examples of proteases are also described in Hook, Proteolytic and cellular mechanisms in prohormone and proprotein processing, RG Landes Company, Austin, Tex., USA (1998); Hooper et al., Biochem. J. 321: 265-279 (1997); Werb, Cell 91: 439-442 (1997); Wolfsberg et al., J. Cell Biol. 131: 275-278 (1995); Murakami and Etlinger, Biochem. Biophys. Res. Comm. 146: 1249-1259 (1987); Berg et al., Biochem. J. 307: 313-326 (1995); Smyth and Trapani, Immunology Today 16: 202-206 (1995); Talanian et al., J. Biol. Chem. 272: 9677-9682 (1997); and Thornberry et al., J. Biol. Chem. 272: 17907-17911 (1997).

As used herein, "activatable CendR element" refers to a CendR element having a molecule, moiety, nanoparticle, compound or other composition covalently coupled to the CendR element, such as to the terminal carboxyl group of the C-terminal element, where the molecule, moiety, nanoparticle, compound or other composition can block internalization and/or tissue penetration of the CendR composition, conjugate, molecule, protein, peptide, etc. and where the molecule, moiety, nanoparticle, compound or other composition can be removed (to expose the terminal carboxy group, for example). Activatable CendR elements are described in U.S. Patent Application Publication No. 2010-0322862, which is hereby incorporated by reference in its entirety and, in particular, for its description of CendR elements and activatable CendR elements.

Exopeptidases, such as carboxypeptidases, can be used to activate peptides. For example, carboxypeptidases are useful proteases for activating peptides. Carboxypeptidases remove the C-terminal amino acid from proteins and peptides. Carboxypeptidases can, within the limits of their substrate preferences, remove amino acids sequentially from a protein or peptide. Thus, for example, a carboxypeptidase could completely or nearly completely hydrolyze a protein of peptide. Because various carboxypeptidases have certain substrate preferences or limitations, and because carboxypeptidases generally only cleave peptide bonds, the presence of certain amino acids, modifications, and/or non-peptide bonds can control carboxypeptidase cleavage of a protein or peptide.

In the context of tLyP-1 peptides, the structure of and/or modifications to a protein, peptide or amino acid sequence comprising a tLyP-1 peptide can be chosen to result in cleavage by a carboxypeptidase ending at the C-terminal amino acid of the tLyP-1 peptide. This can be accomplished by, for example, using a bond between the C-terminal amino acid and the penultimate amino acid in the tLyP-1 peptide that can be protected from protease cleavage. For example, the bond can be a non-peptide bond or can include a modification, such as methylation. As another example, a D-amino acid can be used as the C-terminal amino acid, the penultimate amino acid, or both, in a tLyP-1 peptide. As another example, a D-amino acid can be used as the C-terminal amino acid in a tLyP-1 peptide. tLyP-1 peptides with limited use of D amino acids retain internalization and penetration activity. As another example, an amino acid that serves as a substrate for a carboxypeptidase can be located C-terminal to the C-terminal amino acid in the tLyP-1 peptide. For example, for a glutamate-specific carboxypeptidase such as PSMA, a glutamic acid amino acid can be placed adjacent to and C-terminal of the C-terminal amino acid in the tLyP-1 peptide and at the C-terminal end of the protein or peptide containing the tLyP-1 peptide. Other amino acid-specific (or preferring) carboxypeptidases can be used in similar ways. In these cases, the C-terminal amino acid in the tLyP-1 petide should not be a substrate (or should be a disfavored substrate) for the carboxypeptidase.

Bonds and modifications to amino acids that can reduce or eliminate protease cleavage at a bond are known and can be used in the disclosed tLyP-1 peptides. For example, a variety of chemical modification techniques and moieties are described in, for example, U.S. Pat. Nos. 5,554,728, 6,869, 932, 6,828,401, 6,673,580, 6,552,170, 6,420,339, U.S. Pat. Pub. 2006/0210526 and Intl. Pat. App. WO 2006/136586. Some examples of such modifications include peptide bond surrogates such as those described in Cudic and Stawikowski, Peptidomimetics: Fmoc Solid-Phase Pseudopeptide Synthesis, in Methods in Molecular Biology, vol. 294, 223-246 (2008), and chemical modifications, such as maleimide capping, polyethylene glycol (PEG) attachment, maleidification, acylation, alkylation, esterification, and amidification, to produce structural analogs of the peptide. These and other modifications are further described elsewhere herein.

The tLyP-1 peptide in a disclosed protein, peptide, amino acid sequence or tLyP-1 composition generally should be at a free C-terminal end or on the N-terminal side of the cleavage site in an activatable tLyP-1 peptide.

Also disclosed are methods of forming an activatable peptide, the method comprising causing a blocking group to be covalently coupled to a peptide, wherein a bond coupling the blocking group and the peptide is cleavable. Also disclosed are methods of forming an activatable peptide, the method comprising causing a blocking group to be covalently coupled to an amino acid sequence, wherein the amino acid sequence comprises the peptide, wherein a bond coupling the blocking group and the peptide is cleavable. Also disclosed are methods of forming an activatable peptide, the method comprising (a) selecting an amino acid sequence for internalization into a cell and/or penetration of tissue, wherein the amino acid sequence comprises a peptide, and (b) causing a blocking group to be covalently coupled to the peptide, wherein a bond coupling the blocking group and the peptide is cleavable. The blocking group covalently coupled to the peptide reduces or prevents internalization into a cell and/or penetration of tissue. The blocking group covalently coupled to the peptide can reduce or prevent internalization into a cell and/or penetration of tissue compared to the same peptide with no blocking group. For example, an amino acid sequence comprising tLyP-1 sequence-cleavage site-homing module can be made and then tested for activatability (via cleavage of the cleavage site, for example). For example, a pool of peptides having the amino acid sequence CGNK-RTR-XXXXXXXXXXXXXXXXX (SEQ ID NO:8) can be tested for homing and activatability. That is, such peptides can be identified by screens using libraries. The activatable peptide can comprise the selected amino acid sequence and the blocking group. The cell can be in a subject. The enzyme, cleaving agent, and/or cleaving conditions present in proximity to the cell of interest can be identified. The enzyme, cleaving agent, and/or cleaving conditions present in proximity to the cell of interest can be identified prior to forming the activatable peptide. The cleavable bond can be selected based on the enzyme that is present in proximity to the cell of interest. The cleavable bond can be selected based on the cleaving agent present at site where the peptide is delivered, homes, travels or accumulates, such as the cell of interest. The cleavable bond can be selected based on the cleaving conditions present at site where the peptide is delivered, homes, travels or accumulates, such as the cell of interest. The cleavable bond can be selected prior to forming the activatable peptide. The peptide can comprise a terminal carboxyl group, wherein the blocking group is coupled to the terminal carboxyl group.

"Internalization" refers to passage through a plasma membrane or other biological barrier. "Penetration" refers to passage into and through a cell, tissue, or other biological barrier. Penetration generally involves and includes internalization. The disclosed tLyP-1 peptides generally promote and allow both internalization (such as internalization into a cell) and penetration (such as tissue penetration). Reference to internalization or to penetration should be understood to refer to both internalization and penetration unless the context indicates otherwise (such as separate or distinct discussion and description of internalization into a cell and tissue penetration separately—the present paragraph is an example of such).

By "internalization into a cell" is meant that that tLyP-1 peptide is capable of penetrating the plasma membrane, thereby being internalized into the cell. This internalization can occur with, for example, 10, 20, 30, 40, 50, 60, 70, 80, 90, or 100% efficiency for a given tLyP-1 peptide and a given cell. tLyP-1 peptides generally an promote, mediate, cause, enhance, etc. internalization; penetration; internalization into and/or through cells, tissue, or both; penetration into and/or through cells, tissue, or both; permeabilization of cells and/or tissues; or a combination. By "permeabilization" is meant promoting, mediating, causing, enhancing, etc. the ability and/or condition of cells and/or tissues to allow compositions, conjugates, molecules, etc. in proximity to the cells and/or tissues to enter and or pass through the cells and/or tissues. Thus, the disclosed tLyP-1 proteins, peptides, conjugates, compositions, etc. can be said to permeabilize the cells and/or tissues. By "permeable" is meant the ability and/or condition of cells and/or tissues to allow compositions, conjugates, molecules, etc. in proximity to the cells and/or tissues to enter and or pass through the cells and/or tissues.

As used herein, "tissue penetration" and "penetration of tissue" refer to passage into or through a tissue beyond or through the outer or a first layer of cells or through a tissue membrane. Such passage or penetration through tissue (which can also be referred to as extravasation and tissue penetration) can be a function of, for example, cell internalization and passage between cells in the tissue. Throughout this application, when the term "tissue penetration" is used, it is understood that such penetration can also extend to other barriers and CendR-capable membranes found throughout the body, such as the blood brain barrier.

Cells that can internalize a tLyP-1 peptide can be identified by, for example, (a) exposing a cell to a tLyP-1 peptide; and (b) determining if the tLyP-1 peptide was internalized. The cell can be in an assay, for example. Any form or type of tLyP-1 peptide, tLyP-1 peptide, tLyP-1 protein, tLyP-1 conjugate, or tLyP-1 composition can be used in these methods. Alternatively, cells that can internalize a tLyP-1 peptide can be identified by detecting or measuring NRP1, NRP2, or both, on the cells.

Cancer cells, or subjects harboring cancer cells, can be identified as candidates for tLyP-1-based therapy by, for example, (a) exposing the cancer cell to a tLyP-1 peptide; and (b) determining if the tLyP-1 peptide was internalized by the cancer cell, wherein an internalized tLyP-1 peptide identifies the cancer cell or the subject as being a candidate for tLyP-1-based therapy. The cell can be in an assay, or can be in a subject, for example. Any form or type of tLyP-1 peptide, tLyP-1 peptide, tLyP-1 protein, tLyP-1 conjugate, or tLyP-1 composition can be used in these methods. Alternatively, cancer cells that can internalize a tLyP-1 peptide can be identified by detecting or measuring NRP1, NRP2, or both, on the cells.

Tumors, or subjects harboring a tumor, can be identified as a candidate for tLyP-1-based therapy by, for example, (a) exposing tissue from the tumor to a tLyP-1 peptide; and (b) determining if the tLyP-1 peptide passed through the tissue or was internalized by cells in the tissue, wherein a passed-through or internalized tLyP-1 peptide identifies the tumor or the subject as being a candidate for tLyP-1-based therapy. Any form or type of tLyP-1 peptide, tLyP-1 peptide, tLyP-1 protein, tLyP-1 conjugate, or tLyP-1 composition can be used in these methods. Alternatively, tumors that can internalize or be penetrated by a tLyP-1 peptide can be identified by detecting or measuring NRP1, NRP2, or both, in the tumors.

The co-composition can be, for example, a nanoparticle, or a molecule, or complex of molecules with therapeutic or diagnostic applications. Therapeutic co-compositions that can be targeted with tLyP-1 peptides include but are not limited to a nanoparticle, a molecule, a complex of molecules, an anti-angiogenic agent, a pro-angiogenic agent, a cancer chemotherapeutic agent, a cytotoxic agent, a pro-cell survival agent, a cell differentiating agent, a neuroprotective agent, an immunomodulatory agent, an anti-inflammatory agent, an anti-arthritic agent, an anti-viral agent, or a combination of these. Therapeutic co-compositions that can be targeted with tLyP-1 peptides include but are not limited to a therapeutic protein, a therapeutic compound, a therapeutic composition, an anti-angiogenic agent, a pro-angiogenic agent, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination. Diagnostic co-compositions that can be targeted with tLyP-1 peptides include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these.

The cargo composition can be, for example, a nanoparticle, or a molecule, or complex of molecules with therapeutic or diagnostic applications. Therapeutic cargo compositions that can be targeted with tLyP-1 peptides include but are not limited to a nanoparticle, a molecule, a complex of molecules, an anti-angiogenic agent, a pro-angiogenic agent, a cancer chemotherapeutic agent, a cytotoxic agent, a pro-cell survival agent, a cell differentiating agent, a neuroprotective agent, an immunomodulatory agent, an anti-inflammatory agent, an anti-arthritic agent, an anti-viral agent, or a combination of these. Therapeutic cargo compositions that can be targeted with tLyP-1 peptides include but are not limited to a therapeutic protein, a therapeutic compound, a therapeutic composition, an anti-angiogenic agent, a pro-angiogenic agent, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination. Diagnostic cargo compositions that can be targeted with tLyP-1 peptides include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these.

A cell that can internalize a tLyP-1 peptide can be identified by, for example, (a) exposing a cell to a tLyP-1 peptide, and (b) determining if the tLyP-1 peptide was internalized. Also disclosed are methods of identifying a cancer cell as a candidate for tLyP-1-based therapy, the method comprising (a) exposing the cancer cell to a tLyP-1 peptide, and (b) determining if the tLyP-1 peptide was internalized by the cancer cell, wherein an internalized tLyP-1 peptide identifies the cancer cell as being a candidate for tLyP-1-based therapy. The cell can be in an assay. The tLyP-1 peptide can be coupled to a protein or peptide. The tLyP-1 peptide can be an activatable tLyP-1 peptide. The activatable tLyP-1 peptide can be activated before exposure to the cell. The activatable tLyP-1 peptide can be a protease-activatable tLyP-1 peptide. The protein or peptide can be circular. The protein or peptide can be linear. The tLyP-1 peptide can be at the C-terminal end of the protein or peptide. Any form or type of tLyP-1 peptide, tLyP-1 peptide, tLyP-1 protein, tLyP-1 conjugate, or tLyP-1 composition can be used in these methods. Alternatively, cells and cancer cells that can internalize a tLyP-1 peptide can be identified by detecting or measuring NRP1, NRP2, or both, on the cells.

A tissue that can be penetrated by a tLyP-1 peptide can be identified by, for example, (a) exposing a tissue to a tLyP-1 peptide, and (b) determining if the tLyP-1 peptide penetrated the tissue. Also disclosed are methods of identifying a tumor as a candidate for tLyP-1-based therapy, the method comprising (a) exposing a cell from the tumor to a tLyP-1 peptide, and (b) determining if the tLyP-1 peptide was internalized by the cell, wherein an internalized tLyP-1 peptide identifies the tumor as being a candidate for tLyP-1-based therapy. A tumor can be identified as a candidate for tLyP-1-based therapy by, for example, (a) exposing the tumor to a tLyP-1 peptide, and (b) determining if the tLyP-1 peptide penetrated the tumor, wherein a tLyP-1 peptide that penetrated identifies the tumor as being a candidate for tLyP-1-based therapy. The tumor can be in an assay. The tLyP-1 peptide can be coupled to a protein or peptide. The tLyP-1 peptide can be an activatable tLyP-1 peptide. The activatable tLyP-1 peptide can be activated before exposure to the tumor. The activatable tLyP-1 peptide can be a protease-activatable tLyP-1 peptide. The protein or peptide can be circular. The protein or peptide can be linear. The tLyP-1 peptide can be at the C-terminal end of the protein or peptide. Any form or type of tLyP-1 peptide, tLyP-1 peptide, tLyP-1 protein, tLyP-1 conjugate, or tLyP-1 composition can be used in these methods. Alternatively, tissue and tumors that can internalize or be penetrated by a tLyP-1 peptide can be identified by detecting or measuring NRP1, NRP2, or both, on the tissue and tumors.

The tLyP-1 peptide can have a length of up to 10, 20, 30, 40, 50, 100, 150, 200, 250, 300, 400, 500, 1000 or 2000 residues. In particular embodiments, a tLyP-1 peptide can have a length of at least 7, 8, 9, 10, 15, 20, 25, 30, 40, 50, 60, 70, 80, 90, 100 or 200 residues. In further embodiments, a tLyP-1 peptide can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

A protein or peptide containing a tLyP-1 peptide can have a length of up to 50, 100, 150, 200, 250, 300, 400, 500, 1000 or 2000 residues. In particular embodiments, the protein or peptide portion of a tLyP-1 composition can have a length of at least 10, 20, 30, 40, 50, 60, 70, 80, 90, 100 or 200 residues. In further embodiments, the protein or peptide containing a tLyP-1 peptide can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The tLyP-1 conjugate can have a length of up to 50, 100, 150, 200, 250, 300, 400, 500, 1000 or 2000 residues. In particular embodiments, a tLyP-1 conjugate can have a length of at least 10, 20, 30, 40, 50, 60, 70, 80, 90, 100 or 200 residues. In further embodiments, a tLyP-1 conjugate can have a length of 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The protein or peptide portion of a tLyP-1 composition can have a length of up to 50, 100, 150, 200, 250, 300, 400, 500, 1000 or 2000 residues. In particular embodiments, the protein or peptide portion of a tLyP-1 composition can have a length of at least 10, 20, 30, 40, 50, 60, 70, 80, 90, 100 or 200 residues. In further embodiments, the protein or peptide portion of a tLyP-1 composition can have a length of 7 to 200 residues, 7 to 100 residues, 7 to 90 residues, 7 to 80 residues, 7 to 70 residues, 7 to 60 residues, 7 to 50 residues, 7 to 40 residues, 7 to 30 residues, 7 to 20 residues, 7 to 15 residues, 7 to 10 residues, 8 to 200 residues, 8 to 100 residues, 8 to 90 residues, 8 to 80 residues, 8 to 70 residues, 8 to 60 residues, 8 to 50 residues, 8 to 40 residues, 8 to 30 residues, 8 to 20 residues, 8 to 15 residues, 8 to 10 residues, 9 to 200 residues, 9 to 100 residues, 9 to 90 residues, 9 to 80 residues, 9 to 70 residues, 9 to 60 residues, 9 to 50 residues, 9 to 40 residues, 9 to 30 residues, 9 to 20 residues, 9 to 15 residues, 9 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The tLyP-1 composition can have a length of up to 50, 100, 150, 200, 250, 300, 400, 500, 1000 or 2000 residues. In particular embodiments, a tLyP-1 composition can have a length of at least 10, 20, 30, 40, 50, 60, 70, 80, 90, 100 or 200 residues. In further embodiments, a tLyP-1 composition can have a length of 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 10 to 15 residues, 15 to 200 residues, 15 to 100 residues, 15 to 90 residues, 15 to 80 residues, 15 to 70 residues, 15 to 60 residues, 15 to 50 residues, 15 to 40 residues, 15 to 30 residues, 15 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

tLyP-1 (and other) peptides can be stabilized against proteolysis. For example, the stability and activity of peptides, such as tumor-homing peptides CREKA (Simberg et al., 2007), by protecting some of the peptide bonds with N-methylation or C-methylation. The most important bond to protect in order to enhance activity is the R-G bond because it would prevent a cleavage that would inactivate both the integrin-binding and tLyP-1 activities. Accessory peptides and homing peptides can also or similarly be stabilized against proteolysis.

The disclosed tLyP-1 peptides (and other tLyP-1 forms) and co-compositions can be administered together or separately; in the same form and manner or in different forms and/or manners; at the same time or at different times; with the tLyP-1 peptide (or other tLyP-1 form) administered first or second. Administration can be, for example, co-administration (at the same time and by the same or different route/means/form), separate administration (parallel administration by the same or different route/means/form), sequential administration (at different times by the same or different route/means/form), etc. When the co-composition and tLyP-1 peptide (or other tLyP-1 form) are administered at different times, a variety of different delays can be used between the administrations. For example, the tLyP-1 peptide (or other tLyP-1 form) can be administered 1, 2, 3, 4, 5, 6, 7, 8, 9, 10, 11, 12, 13, 15, 20, 30, 40, 45, 50, 60, 70, 80, 90, 100, 110, or 120 minutes or more before administering a co-composition. The tLyP-1 peptide (or other tLyP-1 form) can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours or more before administering a co-composition. The tLyP-1 peptide (or other tLyP-1 form) can be administered 1, 2, 3, 4, 5, 6, or 7 days or more before administering a co-composition. The tLyP-1 peptide (or other tLyP-1 form) can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours or more after administering a co-composition. The tLyP-1 peptide (or other tLyP-1 form) can be administered 1, 2, 3, 4, 5, 6, or 7 days or more after administering a co-composition. The tLyP-1 peptide (or other tLyP-1 form) can be administered within 1, 2, 3, 4, 5, 6, 7, 8, 9, 10, 11, 12, 13, 15, 20, 30, 40, 45, 50, 60, 70, 80, 90, 100, 110, or 120 minutes before administering a co-composition. The tLyP-1 peptide (or other tLyP-1 form) can be administered within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours before administering a co-composition. The tLyP-1 peptide (or other tLyP-1 form) can be administered within 1, 2, 3, 4, 5, 6, or 7 days before administering a co-composition. The tLyP-1 peptide (or other tLyP-1 form) can be administered within 1, 2, 3, 4, 5, 6, 7, 8, 9, 10, 11, 12, 13, 15, 20, 30, 40, 45, 50, 60, 70, 80, 90, 100, 110, or 120 minutes after administering a co-composition. The tLyP-1 peptide (or other tLyP-1 form) can be administered within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours after administering a co-composition. The tLyP-1 peptide (or other tLyP-1 form) can be administered within 1, 2, 3, 4, 5, 6, or 7 days after administering a co-composition. Administration within the same day or hour is particularly useful.

The tLyP-1 composition, tLyP-1 conjugate, tLyP-1 molecule, tLyP-1 protein, or tLyP-1 peptide and the co-composition can be administered to the subject simultaneously. By simultaneously is meant during overlapping or contiguous time periods. The tLyP-1 composition, tLyP-1 conjugate, tLyP-1 molecule, tLyP-1 protein, or tLyP-1 peptide and the co-composition can be administered to the subject in a single composition comprising the tLyP-1 composition, tLyP-1 conjugate, tLyP-1 molecule, tLyP-1 protein, or tLyP-1 peptide and the co-composition. The tLyP-1 composition, tLyP-1 conjugate, tLyP-1 molecule, tLyP-1 protein, or tLyP-1 peptide and the co-composition can be administered to the subject in separate compositions. The tLyP-1 peptide and the co-composition can be administered to the subject at different times. The tLyP-1 peptide and the co-composition can be administered to the subject in separate compositions. By separate compositions is meant compositions that are not mixed or in contact with each other (except as may occur following administration). The tLyP-1 peptide and the co-composition can be administered to the subject by separate routes. By separate routes is meant in separate locations, by different means or mode, or both.

tLyP-1 peptides can be made in the form of stabilized peptides and/or formulated as long-circulating forms. For example, a polyethylene glycol conjugate can be used. tLyP-1 peptides and/or co-compositions can also be administered over a period of time. For example, tLyP-1 peptides and/or co-compositions can be delivered with an osmotic pump. This can extend the permeability of the target cells and tissues. Modified forms of tLyP-1 peptides can be used. For example, tLyP-1 peptides can be methylated (which can stabilize the peptides against proteolysis). Stability against cleavage is desirable, except for bonds to be cleaved to activate tLyP-1 peptides. Modifications to tLyP-1 peptides generally should leave them functional or capable of function after activation.

It is understood that there are numerous amino acid and peptide analogs which can be incorporated into the disclosed tLyP-1 compositions, conjugates, molecules, proteins, peptides, and elements. For example, there are numerous D amino acids or other non-natural amino acids which can be used. The opposite stereoisomers of naturally occurring peptides are disclosed, as well as the stereo isomers of peptide analogs. These amino acids can readily be incorporated into polypeptide chains by chemical synthesis or by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —CH=CH— (cis and trans), —$COCH_2$—, —$CH(OH)$ $CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—$CH(OH)$ $CH_2$—); Holladay et al. Tetrahedron. Lett 24:4401-4404 (1983) (—$C(OH)CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides as long as activity is preserved. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Disclosed are polyfunctional tLyP-1 compositions which, in addition to the tLyP-1 peptide, contain, for example, an accessory peptide, an accessory peptide fused to the tLyP-1 peptide, an accessory molecule covalently coupled to or non-covalently associated with the tLyP-1 peptide, a homing peptide fused to the tLyP-1 peptide, a homing molecule covalently coupled to or non-covalently associated with the tLyP-1 peptide, a cargo composition fused to the tLyP-1 peptide, and/or a cargo composition covalently coupled to or non-covalently associated with the tLyP-1 peptide. Additional compounds having separate functions can be added to the composition. Such polyfunctional conjugates have at least two functions conferred by different portions of the composition and can, for example, display anti-angiogenic activity or pro-apoptotic activity in addition to selective homing activity.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as that from which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

tLyP-1 peptides and CendR elements bind to neuropilin-1 (NRP-1) present on the cell surface. tLyP-1 peptides also binds to neuropilin-2 (NRP-2) present on the cell surface. Binding of tLyP-1 peptides to NRP-1 or NRP-2 mediates internalization of the tLyP-1 peptide, anything attached to the tLyP-1 peptide, and co-compositions.

A design principle for homing peptides has been developed that combines three functions: tissue-specific homing, spreading within the target tissue, and internalization into cells in that tissue. These peptides contain both a tissue-specific homing sequence and a tissue-penetrating and internalizing motif embodied in a tLyP-1 peptide.

The disclosed compounds are useful tools for introducing materials into the target tissues. They can allow disease-specific or cell type and tissue-specific targeting of diagnostic and therapeutic compounds to increase efficacy and decrease side effects. The principles disclosed herein are applicable to any cells or tissues for which specific homing peptides can be obtained and that express a CendR receptor (which most cells do).

Studies have revealed extensive molecular heterogeneity in the vasculature of different normal tissues. In addition, pathological lesions, such as tumors, impose their own changes on the vasculature. This system of molecular markers can be referred to as 'vascular zip codes' (Ruoslahti, 2004). The zip codes enable docking-based ('synaphic') targeting to selectively deliver diagnostics and therapeutics into a specific tissue. This approach can produce greater efficacy and diminished side effects. The targeted delivery principle has been established, particularly in cancer: targeting of radioisotopes to leukemic cells with antibodies is an established therapy, and several products aimed at diagnosis and treatment of solid tumors are in clinical trials; many of them use early generation tumor-homing peptides or their derivatives. However, one issue in making the synaphic delivery more generally useful is that efficacy has tended to be low. It has been realized that it may be more effective to target the delivery to blood vessels because their inner endothelial lining is readily available to circulating probes, whereas penetration into tumor parenchyma has been a problem in the past (Jain, 1990). Thus, while it has been easy to demonstrate binding of the targeted material to the target vessels, a substantially higher concentration of the material in the target tissue has not necessarily been achieved (e.g. Liu et al., 2007).

The disclosed peptides can be validated by, for example, testing in vitro cell binding and internalization, and in vivo homing. Synthetic peptides can be used to show that the activities associated with the selected phage are reproduced by the peptide the phage displays. Techniques for this are well known (e.g. Zhang et al., 2005; Simberg et al., 2007; Karmali et al., 2008). The peptides generally can be labeled with a fluorophore to allow detection in tissues, and both the free peptide and a multimeric conjugate on nanoparticles (which more closely resembles the multivalent presentation on phage) can be tested.

A variety of homing molecules can be used in the disclosed compositions, conjugates and methods. Such homing molecules include, without limitation, peptides as disclosed herein. The disclosed compounds, compositions, conjugates and methods can include or use the disclosed homing molecules in various forms, including peptides and peptidomimetics as disclosed. For convenience of expression, in many places herein the use or inclusion of peptides will be recited. It is understood that, in such cases, it is considered that homing molecules in various forms can also be used or included in the same or similar ways as is described in terms of peptides, and such use and inclusion is specifically contemplated and disclosed thereby.

The term "homing molecule" as used herein, means any molecule that selectively homes in vivo to specific cells or specific tissue in preference to normal tissue. Similarly, the term "homing peptide" or "homing peptidomimetic" means a peptide that selectively homes in vivo to specific cells or specific tissue in preference to normal tissue. It is understood that a homing molecule that selectively homes in vivo to specific cells or specific tissue or can exhibit preferential homing to r specific cells or specific tissue.

By "selectively homes" is meant that, in vivo, the homing molecule binds preferentially to the target as compared to non-target. For example, the homing molecule can bind preferentially to tumors, as compared to non-tumors. Selective homing to, for example, tumor cells generally is characterized by at least a two-fold greater localization within tumor cells, as compared to several tissue types of non-tumor cells. A homing molecule can be characterized by, for example, 5-fold, 10-fold, 20-fold or more preferential localization to the target as compared to one or more non-targets. For example, a homing molecule can be characterized by, for example, 5-fold, 10-fold, 20-fold or more preferential localization to tumor vasculature as compared to vasculature of several or many tissue types of non-tumoral tissue, or as compared to vasculature of most or all non-tumoral tissue. As another example, a homing molecule can be characterized by, for example, 5-fold, 10-fold, 20-fold or more preferential localization to tumors as compared to several or many tissue types of non-tumoral tissue, or as compared to-most or all non-tumoral tissue. Thus, it is understood that, in some cases, a homing molecule homes, in part, to one or more normal organs in addition to homing to the target tissue. Selective homing can also be referred to as targeting. The molecules, proteins, cells, tissues, etc. that are targeted by homing molecules can be referred to as targeted molecules, proteins, cells, tissues, etc.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces. This binding can occur in addition to that binding which occurs with the tLyP-1 peptide.

Surface molecules can be associated with and arranged in the compositions in a variety of configurations. In some forms, surface molecules can be associated with, conjugated to, and/or covalently coupled to a plurality of homing molecules, a plurality of cargo molecules, or both. In some forms, surface molecules can be associated with, conjugated to, and/or covalently coupled to a plurality of homing molecules, wherein the homing molecules can be associated with, conjugated to, and/or covalently coupled to a plurality of cargo molecules. In some forms, surface molecules can be associated with, conjugated to, and/or covalently coupled to a plurality of cargo molecules, wherein the cargo molecules can be associated with, conjugated to, and/or covalently coupled to a plurality of homing molecules. Combinations of these combinations can also be used.

The surface molecules, alternatively referred to as a surface particles, disclosed herein can be conjugated with homing molecules and cargo molecules in such a way that the composition is delivered to a target. The surface molecule can be any substance that can be used with the homing molecules and cargo molecules, and is not restricted by size or substance. Examples include, but are not limited to, nanoparticles (such as iron oxide nanoparticles or albumin nanoparticles), liposomes, small organic molecules, microparticles, or microbubbles, such as fluorocarbon microbubbles. The term surface molecule is used to identify a component of the disclosed composition but is not intended to be limiting. In particular, the disclosed surface molecules are not limited to substances, compounds, compositions, particles or other materials composed of a single molecule. Rather, the disclosed surface molecules are any substance(s), compound(s), composition(s), particle(s) and/or other material(s) that can be conjugated with a plurality of homing molecules and cargo molecules such that at least some of the homing molecules and/or cargo molecules are presented and/or accessible on the surface of the surface molecule. A variety of examples of suitable surface molecules are described and disclosed herein.

The surface molecule can be detectable, or can be a therapeutic agent such as iRGD, RGD, or Abraxane™. The section herein which discusses cargo molecules and moieties that can be detectable or therapeutic also applies to the surface molecule.

The term "nanoparticle" refers to a nanoscale particle with a size that is measured in nanometers, for example, a nanoscopic particle that has at least one dimension of less than about 100 nm. Examples of nanoparticles include paramagnetic nanoparticles, superparamagnetic nanoparticles, metal nanoparticles, nanoworms, fullerene-like materials, inorganic nanotubes, dendrimers (such as with covalently attached metal chelates), nanofibers, nanohorns, nano-onions, nanorods, nanoropes and quantum dots. A nanoparticle can produce a detectable signal, for example, through absorption and/or emission of photons (including radio frequency and visible photons) and plasmon resonance.

Microspheres (or microbubbles) can also be used with the methods disclosed herein. Microspheres containing chromophores have been utilized in an extensive variety of applications, including photonic crystals, biological labeling, and flow visualization in microfluidic channels. See, for example, Y. Lin, et al., Appl. Phys Lett. 2002, 81, 3134; D. Wang, et al., Chem. Mater. 2003, 15, 2724; X. Gao, et al., J. Biomed. Opt. 2002, 7, 532; M. Han, et al., Nature Biotechnology. 2001, 19, 631; V. M. Pai, et al., Mag. & Magnetic Mater. 1999, 194, 262, each of which is incorporated by reference in its entirety. Both the photostability of the chromophores and the monodispersity of the microspheres can be important.

Nanoparticles, such as, for example, metal nanoparticles, metal oxide nanoparticles, or semiconductor nanocrystals can be incorporated into microspheres. The optical, magnetic, and electronic properties of the nanoparticles can allow them to be observed while associated with the microspheres and can allow the microspheres to be identified and spatially monitored. For example, the high photostability, good fluorescence efficiency and wide emission tunability of colloidally synthesized semiconductor nanocrystals can make them an excellent choice of chromophore. Unlike organic dyes, nanocrystals that emit different colors (i.e. different wavelengths) can be excited simultaneously with a single light source. Colloidally synthesized semiconductor nanocrystals (such as, for example, core-shell CdSe/ZnS and CdS/ZnS nanocrystals) can be incorporated into microspheres. The microspheres can be monodisperse silica microspheres.

The nanoparticle can be a metal nanoparticle, a metal oxide nanoparticle, or a semiconductor nanocrystal. The metal of the metal nanoparticle or the metal oxide nanoparticle can include titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, zinc, cadmium, scandium, yttrium, lanthanum, a lanthanide series or actinide series element (e.g., cerium, praseodymium, neodymium, promethium, samarium, europium, gadolinium, terbium, dysprosium, holmium, erbium, thulium, ytterbium, lutetium, thorium, protactinium, and uranium), boron, aluminum, gallium, indium, thallium, silicon, germanium, tin, lead, antimony, bismuth, polonium, magnesium, calcium, strontium, and barium. In certain embodiments, the metal can be iron, ruthenium, cobalt, rhodium, nickel, palladium, platinum, silver, gold, cerium or samarium. The metal oxide can be an oxide of any of these materials or combination of materials. For example, the metal can be gold, or the metal oxide can be an iron oxide, a cobalt oxide, a zinc oxide, a cerium oxide, or a titanium oxide. Preparation of metal and metal oxide nanoparticles is described, for example, in U.S. Pat. Nos. 5,897, 945 and 6,759,199, each of which is incorporated by reference in its entirety.

The nanoparticles can be comprised of cargo molecules and a carrier protein (such as albumin). Such nanoparticles are useful, for example, to deliver hydrophobic or poorly soluble compounds. Nanoparticles of poorly water soluble drugs (such as taxane) have been disclosed in, for example, U.S. Pat. Nos. 5,916,596; 6,506,405; and 6,537,579 and also in U.S. Pat. Pub. No. 2005/0004002A1.

In forms, the nanoparticles can have an average or mean diameter of no greater than about 1000 nanometers (nm), such as no greater than about any of 900, 800, 700, 600, 500, 400, 300, 200, and 100 nm. In some forms, the average or mean diameters of the nanoparticles can be no greater than about 200 nm. In some forms, the average or mean diameters of the nanoparticles can be no greater than about 150 nm. In some forms, the average or mean diameters of the nanoparticles can be no greater than about 100 nm. In some forms, the average or mean diameter of the nanoparticles can be about 20 to about 400 nm. In some forms, the average or mean diameter of the nanoparticles can be about 40 to about 200 nm. In some embodiments, the nanoparticles are sterile-filterable.

The nanoparticles can be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

Examples of suitable carrier proteins include proteins normally found in blood or plasma, which include, but are not limited to, albumin, immunoglobulin including IgA, lipoproteins, apolipoprotein B, alpha-acid glycoprotein, beta-2-macroglobulin, thyroglobulin, transferin, fibronectin, factor VII, factor VIII, factor IX, factor X, and the like. In some embodiments, the carrier protein is non-blood protein, such as casein, .alpha.-lactalbumin, and beta.-lactoglobulin. The carrier proteins may either be natural in origin or synthetically prepared. In some embodiments, the pharmaceutically acceptable carrier comprises albumin, such as human serum albumin. Human serum albumin (HSA) is a highly soluble globular protein of $M_r$ 65 K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, JAMA 237:355-360, 460-463 (1977)) and Houser et al., Surgery, Gynecology and Obstetrics, 150:811-816 (1980)) and in conjunction with exchange transfusion in the treatment of neonatal hyperbilirubinemia (see, e.g., Finlayson, Seminars in Thrombosis and Hemostasis, 6:85-120 (1980)). Other albumins are contemplated, such as bovine serum albumin. Use of such non-human albumins could be appropriate, for example, in the context of use of these compositions in non-human mammals, such as the veterinary (including domestic pets and agricultural context).

Carrier proteins (such as albumin) in the composition generally serve as a carrier for the hydrophobic cargo molecules, i.e., the carrier protein in the composition makes the cargo molecules more readily suspendable in an aqueous medium or helps maintain the suspension as compared to compositions not comprising a carrier protein. This can avoid the use of toxic solvents (or surfactants) for solubilizing the cargo molecules, and thereby can reduce one or more side effects of administration of the cargo molecules into an individual (such as a human). Thus, in some embodiments, the composition described herein can be substantially free (such as free) of surfactants, such as Cremophor (including Cremophor EL® (BASF)). In some embodiments, the composition can be substantially free (such as free) of surfactants. A composition is "substantially free of Cremophor" or "substantially free of surfactant" if the amount of Cremophor or surfactant in the composition is not sufficient to cause one or more side effect(s) in an individual when the composition is administered to the individual.

The amount of carrier protein in the composition described herein will vary depending on other components in the composition. In some embodiments, the composition, co-composition, cargo composition, and/or tLyP-1 composition can comprise a carrier protein in an amount that is sufficient to stabilize the cargo molecules in an aqueous suspension, for example, in the form of a stable colloidal suspension (such as a stable suspension of nanoparticles). In some embodiments, the carrier protein is in an amount that reduces the sedimentation rate of the cargo molecules in an aqueous medium. For particle-containing compositions, the amount of the carrier protein also depends on the size and density of nanoparticles of the cargo molecules.

Methods of making nanoparticle compositions are known in the art. For example, nanoparticles containing cargo molecules and carrier protein (such as albumin) can be prepared under conditions of high shear forces (e.g., sonication, high pressure homogenization, or the like). These methods are disclosed in, for example, U.S. Pat. Nos. 5,916,596; 6,506,405; and 6,537,579 and also in U.S. Pat. Pub. No. 2005/0004002A1.

Briefly, the hydrophobic carrier molecules can be dissolved in an organic solvent, and the solution can be added to a human serum albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride and chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

The nanoparticle can also be, for example, a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Targeting molecules can be attached to the disclosed compositions and/or carriers. For example, the targeting molecules can be antibodies or fragments thereof, ligands for specific receptors, or other proteins specifically binding to the surface of the cells to be targeted.

"Liposome" as the term is used herein refers to a structure comprising an outer lipid bi- or multi-layer membrane surrounding an internal aqueous space. Liposomes can be used to package any biologically active agent for delivery to cells.

Materials and procedures for forming liposomes are well-known to those skilled in the art. Upon dispersion in an appropriate medium, a wide variety of phospholipids swell, hydrate and form multilamellar concentric bilayer vesicles with layers of aqueous media separating the lipid bilayers. These systems are referred to as multilamellar liposomes or multilamellar lipid vesicles ("MLVs") and have diameters within the range of 10 nm to 100 μm. These MLVs were first described by Bangham, et al., J Mol. Biol. 13:238-252 (1965). In general, lipids or lipophilic substances are dissolved in an organic solvent. When the solvent is removed, such as under vacuum by rotary evaporation, the lipid residue forms a film on the wall of the container. An aqueous solution that typically contains electrolytes or hydrophilic biologically active materials is then added to the film. Large MLVs are produced upon agitation. When smaller MLVs are desired, the larger vesicles are subjected to sonication, sequential filtration through filters with decreasing pore size or reduced by other forms of mechanical shearing. There are also techniques by which MLVs can be reduced both in size and in number of lamellae, for example, by pressurized extrusion (Barenholz, et al., FEBS Lett. 99:210-214 (1979)).

Liposomes can also take the form of unilamnellar vesicles, which are prepared by more extensive sonication of MLVs, and consist of a single spherical lipid bilayer surrounding an aqueous solution. Unilamellar vesicles ("ULVs") can be small, having diameters within the range of 20 to 200 nm, while larger ULVs can have diameters within the range of 200 nm to 2 μm. There are several well-known techniques for making unilamellar vesicles. In Papahadjopoulos, et al., Biochim et Biophys Acta 135:624-238 (1968), sonication of an aqueous dispersion of phospholipids produces small ULVs having a lipid bilayer surrounding an aqueous solution. Schneider, U.S. Pat. No. 4,089,801 describes the formation of liposome precursors by ultrasonication, followed by the addition of an aqueous medium containing amphiphilic compounds and centrifugation to form a biomolecular lipid layer system.

Small ULVs can also be prepared by the ethanol injection technique described by Batzri, et al., Biochim et Biophys Acta 298:1015-1019 (1973) and the ether injection technique of Deamer, et al., Biochim et Biophys Acta 443:629-634 (1976). These methods involve the rapid injection of an organic solution of lipids into a buffer solution, which results in the rapid formation of unilamellar liposomes. Another technique for making ULVs is taught by Weder, et al. in "Liposome Technology", ed. G. Gregoriadis, CRC Press Inc., Boca Raton, Fla., Vol. I, Chapter 7, pg. 79-107 (1984). This detergent removal method involves solubilizing the lipids and additives with detergents by agitation or sonication to produce the desired vesicles.

Papahadjopoulos, et al., U.S. Pat. No. 4,235,871, describes the preparation of large ULVs by a reverse phase evaporation technique that involves the formation of a water-in-oil emulsion of lipids in an organic solvent and the drug to be encapsulated in an aqueous buffer solution. The organic solvent is removed under pressure to yield a mixture which, upon agitation or dispersion in an aqueous media, is converted to large ULVs. Suzuki et al., U.S. Pat. No. 4,016,100, describes another method of encapsulating agents in unilamellar vesicles by freezing/thawing an aqueous phospholipid dispersion of the agent and lipids.

In addition to the MLVs and ULVs, liposomes can also be multivesicular. Described in Kim, et al., Biochim et Biophys Acta 728:339-348 (1983), these multivesicular liposomes are spherical and contain internal granular structures. The outer membrane is a lipid bilayer and the internal region contains small compartments separated by bilayer septum. Still yet another type of liposomes are oligolamellar vesicles ("OLVs"), which have a large center compartment surrounded by several peripheral lipid layers. These vesicles, having a diameter of 2-15 μm, are described in Callo, et al., Cryobiology 22(3):251-267 (1985).

Mezei, et al., U.S. Pat. Nos. 4,485,054 and 4,761,288 also describe methods of preparing lipid vesicles. More recently, Hsu, U.S. Pat. No. 5,653,996 describes a method of preparing liposomes utilizing aerosolization and Yiournas, et al., U.S. Pat. No. 5,013,497 describes a method for preparing liposomes utilizing a high velocity-shear mixing chamber. Methods are also described that use specific starting materials to produce ULVs (Wallach, et al., U.S. Pat. No. 4,853,228) or OLVs (Wallach, U.S. Pat. Nos. 5,474,848 and 5,628,936).

A comprehensive review of all the aforementioned lipid vesicles and methods for their preparation are described in "Liposome Technology", ed. G. Gregoriadis, CRC Press Inc., Boca Raton, Fla., Vol. I, II & III (1984). This and the aforementioned references describing various lipid vesicles suitable for use in the invention are incorporated herein by reference.

"Micelle" as used herein refers to a structure comprising an outer lipid monolayer. Micelles can be formed in an aqueous medium when the Critical Micelle Concentration (CMC) is exceeded. Small micelles in dilute solution at approximately the critical micelle concentration (CMC) are generally believed to be spherical. However, under other conditions, they may be in the shape of distorted spheres, disks, rods, lamellae, and the like. Micelles formed from relatively low molecular weight amphiphile molecules can have a high CMC so that the formed micelles dissociate rather rapidly upon dilution. If this is undesired, amphiphile molecules with large hydrophobic regions can be used. For example, lipids with a long fatty acid chain or two fatty acid chains, such as phospholipids and sphingolipids, or polymers, specifically block copolymers, can be used.

Polymeric micelles have been prepared that exhibit CMCs as low as $10^{-6}$ M (molar). Thus, they tend to be very stable while at the same time showing the same beneficial characteristics as amphiphile micelles. Any micelle-forming polymer presently known in the art or as such may become known in the future may be used in the disclosed compositions and methods. Examples of micelle-forming polymers include, without limitation, methoxy poly(ethylene glycol)-b-poly(ε-caprolactone), conjugates of poly(ethylene glycol) with phosphatidyl-ethanolamine, poly(ethylene glycol)-b-polyesters, poly(ethylene glycol)-b-poly(L-aminoacids), poly(N-vinylpyrrolidone)-b-poly(orthoesters), poly(N-vinylpyrrolidone)-b-polyanhydrides and poly(N-vinylpyrrolidone)-b-poly(alkyl acrylates).

Micelles can be produced by processes conventional in the art. Examples of such are described in, for example, Liggins (Liggins, R. T. and Burt, H. M., "Polyether-polyester diblock copolymers for the preparation of paclitaxel loaded polymeric micelle formulations." Adv. Drug Del. Rev. 54: 191-202, (2002)); Zhang, et al. (Zhang, X. et al., "Development of amphiphilic diblock copolymers as micellar carriers of taxol." Int. J. Pharm. 132: 195-206, (1996)); and Churchill (Churchill, J. R., and Hutchinson, F. G., "Biodegradable amphipathic copolymers." U.S. Pat. No. 4,745,160, (1988)). In one such method, polyether-polyester block copolymers, which are amphipathic polymers having hydrophilic (polyether) and hydrophobic (polyester) segments, are used as micelle forming carriers.

Another type of micelle can be formed using, for example, AB-type block copolymers having both hydrophilic and hydrophobic segments, as described in, for example, Tuzar (Tuzar, Z. and Kratochvil, P., "Block and graft copolymer micelles in solution.", Adv. Colloid Interface Sci. 6:201-232, (1976)); and Wilhelm, et al. (Wilhelm, M. et al., "Poly(styrene-ethylene oxide) block copolymer micelle formation in water: a fluorescence probe study.", Macromolecules 24: 1033-1040 (1991)). These polymeric micelles are able to maintain satisfactory aqueous stability. These micelles, in the range of approximately <200 nm in size, are effective in reducing non-selective RES scavenging and show enhanced permeability and retention.

Further, U.S. Pat. No. 5,929,177 to Kataoka, et al. describes a polymeric molecule which is usable as, inter alia, a drug delivery carrier. The micelle is formed from a block copolymer having functional groups on both of its ends and which comprises hydrophilic/hydrophobic segments. The polymer functional groups on the ends of the block copolymer include amino, carboxyl and mercapto groups on the .alpha.-terminal and hydroxyl, carboxyl group, aldehyde group and vinyl group on the .omega.-terminal. The hydrophilic segment comprises polyethylene oxide, while the hydrophobic segment is derived from lactide, lactone or (meth)acrylic acid ester.

Further, for example, poly(D,L-lactide)-b-methoxypolyethylene glycol (MePEG:PDLLA) diblock copolymers can be made using MePEG 1900 and 5000. The reaction can be allowed to proceed for 3 hr at 160° C., using stannous octoate (0.25%) as a catalyst. However, a temperature as low as 130° C. can be used if the reaction is allowed to proceed for about 6 hr, or a temperature as high as 190° C. can be used if the reaction is carried out for only about 2 hr.

As another example, N-isopropylacrylamide ("IPAAm") (Kohjin, Tokyo, Japan) and dimethylacrylamide ("DMAAm") (Wako Pure Chemicals, Tokyo, Japan) can be used to make hydroxyl-terminated poly(IPAAm-co-DMAAm) in a radical polymerization process, using the method of Kohori, F. et al. (1998). (Kohori, F. et al., "Preparation and characterization of thermally Responsive block copolymer micelles comprising poly(N-isopropylacrylamide-b-D,L-lactide)." J. Control. Rel. 55: 87-98, (1998)). The obtained copolymer can be dissolved in cold water and filtered through two ultrafiltration membranes with a 10,000 and 20,000 molecular weight cut-off. The polymer solution is first filtered through a 20,000 molecular weight cut-off membrane. Then the filtrate was filtered again through a 10,000 molecular weight cut-off membrane. Three molecular weight fractions can be obtained as a result, a low molecular weight, a middle molecular weight, and a high molecular weight fraction. A block copolymer can then be synthesized by a ring opening polymerization of D,L-lactide from the terminal hydroxyl group of the poly(IPAAm-co-DMAAm) of the middle molecular weight fraction. The resulting poly(IPAAm-co-DMAAm)-b-poly(D,L-lactide) copolymer can be purified as described in Kohori, F. et al. (1999). (Kohori, F. et al., "Control of adriamycin cytotoxic activity using thermally responsive polymeric micelles composed of poly(N-isopropylacrylamide-co-N,N-dimethylacrylamide)-b-poly(D,L-lacide).-", Colloids Surfaces B: Biointerfaces 16: 195-205, (1999)).

Examples of block copolymers from which micelles can be prepared which can be used to coat a support surface are found in U.S. Pat. No. 5,925,720, to Kataoka, et al., U.S. Pat. No. 5,412,072 to Sakarai, et al., U.S. Pat. No. 5,410,016 to Kataoka, et al., U.S. Pat. No. 5,929,177 to Kataoka, et al., U.S. Pat. No. 5,693,751 to Sakurai, et al., U.S. Pat. No. 5,449,513 to Yokoyama, et al., WO 96/32434, WO 96/33233 and WO 97/0623, the contents of all of which are incorporated by reference. Modifications thereof which are prepared by introducing thereon a suitable functional group (including an ethyleneically unsaturated polymerizable group) are also examples of block copolymers from which micelles of the present invention are preferably prepared. Preferable block copolymers are those disclosed in the above-mentioned patents and or international patent publications. If the block copolymer has a sugar residue on one end of the hydrophilic polymer segment, as in the block copolymer of WO 96/32434, the sugar residue should preferably be subjected to Malaprade oxidation so that a corresponding aldehyde group may be formed.

Lipids are synthetically or naturally-occurring molecules which includes fats, waxes, sterols, prenol lipids, fat-soluble vitamins (such as vitamins A, D, E and K), glycerolipids, monoglycerides, diglycerides, triglycerides, glycerophospholipids, sphingolipids, phospholipids, fatty acids monoglycerides, saccharolipids and others. Lipids can be hydrophobic or amphiphilic small molecules; the amphiphilic nature of some lipids allows them to form structures such as monolayers, vesicles, micelles, liposomes, bi-layers or membranes in an appropriate environment i.e. aqueous environment. Any of a number of lipids can be used as amphiphile molecules, including amphipathic, neutral, cationic, and anionic lipids. Such lipids can be used alone or in combination, and can also include bilayer stabilizing components such as polyamide oligomers (see, e.g., U.S. Pat. No. 6,320,017, "Polyamide Oligomers", by Ansell), peptides, proteins, detergents, lipid-derivatives, such as PEG coupled to phosphatidylethanolamine and PEG conjugated to ceramides (see, U.S. Pat. No. 5,885,613). In a preferred embodiment, cloaking agents, which reduce elimination of liposomes by the host immune system, can also be included, such as polyamide-oligomer conjugates, e.g., ATTA-lipids, (see, U.S. patent application Ser. No. 08/996,783, filed Feb. 2, 1998) and PEG-lipid conjugates (see, U.S. Pat. Nos. 5,820,873, 5,534,499 and 5,885,613).

Any of a number of neutral lipids can be included, referring to any of a number of lipid species which exist either in an uncharged or neutral zwitterionic form at physiological pH, including diacylphosphatidylcholine, diacylphosphatidylethanolamine, ceramide, sphingomyelin, cephalin, cholesterol, cerebrosides, and diacylglycerols.

Cationic lipids, carry a net positive charge at physiological pH, can readily be used as amphiphile molecules. Such lipids include, but are not limited to, N,N-dioleyl-N,N-dimethylammonium chloride ("DODAC"); N-(2,3-dioleyloxy) propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3.beta.-(N—(N',N'-dimethylaminoethane)-carbamoyl)cholesterol ("DC-Chol"), N-(1-(2,3-dioleyloxyl)propyl)-N-2-(sperminecarboxamido) ethyl)-N,N-dimethyl-ammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as LIPOFECTIN (including DOTMA and DOPE, available from GIBCO/BRL), LIPOFECTAMINE (comprising DOSPA and DOPE, available from GIBCO/BRL), and TRANSFECTAM (comprising DOGS, in ethanol, from Promega Corp.).

Anionic lipids can be used as amphiphile molecules and include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

Amphiphatic lipids can also be suitable amphiphile molecules. "Amphipathic lipids" refer to any suitable material, wherein the hydrophobic portion of the lipid material orients into a hydrophobic phase, while the hydrophilic portion orients toward the aqueous phase. Such compounds include, but are not limited to, fatty acids, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols. Zwitterionic lipids are a form of amphiphatic lipid.

Sphingolipids are fatty acids conjugated to the aliphatic amino alcohol sphingosine. The fatty acid can be covalently bond to sphingosine via an amide bond. Any amino acid as described above can be covalently bond to sphingosine to form a sphingolipid. A sphingolipid can be further modified by covalent bonding through the α-hydroxyl group. The modification can include alkyl groups, alkenyl groups, alkynyl groups, aromatic groups, heteroaromatic groups, cyclyl groups, heterocyclyl groups, phosphonic acid groups. Non-limiting examples of shingolipids are N-acylsphingosine, N-Acylsphingomyelin, Forssman antigen.

Saccharolipids are compounds that contain both fatty acids and sugars. The fatty acids are covalently bonded to a sugar backbone. The sugar backbone can contain one or more sugars. The fatty acids can bond to the sugars via either amide or ester bonds. The sugar can be any sugar base. The fatty acid can be any fatty acid as described elsewhere herein. The provided compositions can comprise either natural or synthetic saccharolipids. Non-limiting saccharolipids are UDP-3-O-(β-hydroxymyristoyl)-GlcNAc, lipid IV A, Kdo2-lipid A.

The disclosed compositions, co-compositions, cargo compositions, and tLyP-1 compositions can include one or more cargo molecules. Generally, the disclosed compositions can include a plurality of cargo molecules. The disclosed compositions can include a single type of cargo molecule or a plurality of different types of cargo molecules. Thus, for example, the disclosed compositions can include a plurality of different types of cargo molecules where a plurality of one or more of the different types of cargo molecules can be present.

Cargo molecules can be any compound, molecule, conjugate, composition, etc. that is desired to be delivered using the disclosed compositions. For example, the cargo molecules can be therapeutic agents, detectable agents, or a combination. For example, the cargo molecules can be membrane perturbing molecules, pro-apoptotic molecules, pore-generating molecules, antimicrobial molecules, mitochondria-affecting molecules, mitochondria-targeted molecules, or a combination. Examples of some useful cargo molecules are described below and elsewhere herein.

Cargo molecules can be associated with and arranged in the compositions in a variety of configurations. In some forms, cargo molecules can be associated with, conjugated to, and/or covalently coupled to a plurality of surface molecules. In some forms, cargo molecules can be associated with, conjugated to, and/or covalently coupled to a plurality of homing molecules. In some forms, cargo molecules can be associated with, conjugated to, and/or covalently coupled to a plurality of homing molecules, wherein the homing molecules can be associated with, conjugated to, and/or covalently coupled to a plurality of surface molecules. Combinations of these combinations can also be used.

Membrane perturbing molecules include molecules that can disrupt membranes, that can form pores in membranes, that can make membranes leaky, that can be targeted to or affect intracellular membranes or organelles, such mitochondria or lysosomes. Some forms of membrane perturbing molecules can be pro-apoptotic while others can be non-apoptotic. Some forms of membrane perturbing molecules can be pro-apoptotic for only some types of cells.

In some forms, one or more of the homing molecules can comprise the amino acid sequence CGKRK (SEQ ID NO:1). In some forms, one or more of the membrane perturbing molecules can comprise the amino acid sequence $_D$(KLAKLAK)$_2$ (SEQ ID NO:3) or a conservative variant thereof, (KLAKLAK)$_2$ (SEQ ID NO:3) or a conservative variant thereof, (KLAKKLA)$_2$ (SEQ ID NO:5) or a conservative variant thereof, (KAAKKAA)$_2$ (SEQ ID NO:6) or a conservative variant thereof, (KLGKKLG)$_3$ (SEQ ID NO:7) or a conservative variant thereof, or a combination. In some forms, one or more of the membrane perturbing molecules can comprise the amino acid sequence $_D$(KLAKLAK)$_2$ (SEQ ID NO:3), (KLAKLAK)$_2$ (SEQ ID NO:3), (KLAKKLA)$_2$ (SEQ ID NO:5), (KAAKKAA)$_2$ (SEQ ID NO:6), (KLGKKLG)$_3$ (SEQ ID NO:7), or a combination. In some forms, one or more of the membrane perturbing molecules can comprise the amino acid sequence $_D$(KLAKLAK)$_2$ (SEQ ID NO:3) or a conservative variant thereof. In some forms, one or more of the membrane perturbing molecules can comprise the amino acid sequence $_D$(KLAKLAK)$_2$ (SEQ ID NO:3). Membrane perturbing peptides of this type are described in Ellerby, Nature Medicine 5, 1032-1038 (1999), which is hereby incorporated by reference for its description of such peptides.

A plurality of modified and/or unmodified membrane perturbing molecules can each be independently selected from, for example, an amino acid segment comprising a modified or unmodified form of the amino acid sequence of a homing peptide, an amino acid segment comprising a modified or unmodified form of the amino acid sequence $_D$(KLAKLAK)$_2$ (SEQ ID NO:3), (KLAKLAK)$_2$ (SEQ ID NO:3), (KLAKKLA)$_2$ (SEQ ID NO:5), (KAAKKAA)$_2$ (SEQ ID NO:6), (KLGKKLG)$_3$ (SEQ ID NO:7), or a combination. A plurality of the membrane perturbing molecules can each independently comprise an amino acid segment comprising a modified or unmodified form of the amino acid sequence of a homing peptide.

The composition, co-composition, cargo composition, and/or tLyP-1 composition can comprise a sufficient number and composition of membrane perturbing molecules (modified or not) such that the composition has a membrane perturbing effect on the target. In one example, sufficiency of the number and composition of modified and/or unmodified membrane perturbing molecules can be determined by assessing membrane disruption, apoptosis, and/or therapeutic effect on the target.

The composition, co-composition, cargo composition, and/or tLyP-1 composition can comprise any number of modified and/or unmodified membrane perturbing molecules. By way of example, the composition, co-composition, cargo composition, and/or tLyP-1 composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more modified and/or unmodified membrane perturbing molecules. The composition can also comprise any number in between those numbers listed above.

Membrane perturbing molecules can be associated with and arranged in the compositions in a variety of configurations. In some forms, membrane perturbing molecules can be associated with, conjugated to, and/or covalently coupled to a plurality of surface molecules. In some forms, membrane perturbing molecules can be associated with, conjugated to, and/or covalently coupled to a plurality of homing molecules. In some forms, membrane perturbing molecules can be associated with, conjugated to, and/or covalently coupled to a plurality of homing molecules, wherein the homing molecules can be associated with, conjugated to, and/or covalently coupled to a plurality of surface molecules. Combinations of these combinations can also be used.

The disclosed membrane perturbing molecules can include modified forms of membrane perturbing molecules. The membrane perturbing molecules can have any useful modification. For example, some modifications can stabilize the membrane perturbing molecule. For example, the disclosed membrane perturbing molecules include methylated membrane perturbing molecules. Methylated membrane perturbing molecules are particularly useful when the membrane perturbing molecule includes a protein, peptide or amino acid segment. For example, a membrane perturbing molecule can be a modified membrane perturbing molecule, where, for example, the modified membrane perturbing molecule includes a modified amino acid segment or amino acid sequence. For example, a modified membrane perturbing molecule can be a methylated membrane perturbing molecule, where, for example, the methylated membrane perturbing molecule includes a methylated amino acid segment or amino acid sequence. Other modifications can be used, either alone or in combination. Where the membrane perturbing molecule is, or includes, a protein, peptide, amino acid segment and/or amino acid sequences, the modification can be to the protein, peptide, amino acid segment, amino acid sequences and/or any amino acids in the protein, peptide, amino acid segment and/or amino acid sequences. Amino acid and peptide modifications are known to those of skill in the art, some of which are described below and elsewhere herein. Methylation is a particularly useful modification for the disclosed membrane perturbing molecules. Using modified forms of membrane perturbing molecules can increase their effectiveness.

The disclosed compositions, surface molecules, cargo molecules, peptides, proteins, amino acid sequences, etc. can comprise one or more internalization elements, tissue penetration elements, or both. Internalization elements and tissue penetration elements can be incorporated into or fused with other peptide components of the composition, such as peptide homing molecules and peptide cargo molecules. Internalization elements are molecules, often peptides or amino acid sequences, that allow the internalization element and components with which it is associated, to pass through biological membranes. Tissue penetration elements are molecules, often peptides or amino acid sequences, that allow the tissue penetration element and components with which it is associated to passage into and through tissue. Some molecules, such as tLyP-1 peptides and CendR elements, function as both internalization elements and tissue penetration elements.

Internalization elements include, for example, cell-penetrating peptides (CPPs) and tLyP-1 peptides. Peptides that are internalized into cells are commonly referred to as cell-penetrating peptides. There are two main classes of such peptides: hydrophobic and cationic (Zorko and Langel, 2005). The cationic peptides, which are commonly used to introduce nucleic acids, proteins into cells, include the prototypic cell-penetrating peptides (CPP), Tat, and penetratin (Derossi et al., 1998; Meade and Dowdy, 2007). A herpes virus protein, VP22, is capable of both entering and exiting cells and carrying a payload with it (Elliott and O'Hare, 1997; Brewis et al., 2003).

Association of the components of the disclosed compositions can be aided or accomplished via molecules, conjugates and/or compositions. Where such molecules, conjugates and/or compositions are other than tLyP-1 peptides, surface molecules, homing molecules, accessory molecules, co-compositions, cargo compositions, or cargo molecules (such as membrane perturbing molecules, internalization elements, tissue penetration elements, and moieties), they can be referred to herein as linkers. Such linkers can be any molecule, conjugate, composition, etc. that can be used to associate components of the disclosed compositions. Generally, linkers can be used to associate components other than surface molecules to surface molecules. Useful linkers include materials that are biocompatible, have low bioactivity, have low antigenicity, etc. That is, such useful linker materials can serve the linking/association function without adding unwanted bioreactivity to the disclosed compositions. Many such materials are known and used for similar linking and association functions. Polymer materials are a particularly useful form of linker material. For example, polyethylene glycols can be used.

Linkers are useful for achieving useful numbers and densities of the components (such as homing molecules and membrane perturbing molecules) on surface molecules. For example, linkers of fibrous form are useful for increasing the number of components per surface molecule or per a given area of the surface molecule. Similarly, linkers having a branching form are useful for increasing the number of components per surface molecule or per a given area of the surface molecule. Linkers can also have a branching fibrous form.

Sufficiency of the number and composition of homing molecules in the composition can be determined by assessing homing to the target and effectively delivery of the cargo molecules in a non-human animal. The composition, co-composition, cargo composition, and/or tLyP-1 composition can comprise a sufficient number and composition of homing molecules (modified or not) such that the composition homes to the target and effectively delivers the cargo molecules. In one example, sufficiency of the number and composition of modified and/or unmodified homing molecules can be determined by assessing cargo delivery and/or therapeutic effect on the target. Sufficiency of the number and composition of membrane perturbing molecules can be determined by assessing membrane perturbing effect of the composition in a non-human animal. The composition, co-composition, cargo composition, and/or tLyP-1 composition can comprise a sufficient number and composition of membrane perturbing molecules (modified or not) such that the composition has a membrane perturbing effect on the target. In one example, sufficiency of the number and composition of modified and/or unmodified membrane perturbing molecules can be determined by assessing membrane disruption, apoptosis, and/or therapeutic effect on the target.

The composition, co-composition, cargo composition, and/or tLyP-1 composition can comprise a sufficient density and composition of homing molecules such that the composition homes to the target and effectively delivers the cargo molecules. Sufficiency of the density and composition of homing molecules can be determined by assessing cargo delivery and/or therapeutic effect on the target in a non-human animal. The composition, co-composition, cargo composition, and/or tLyP-1 composition can comprise a sufficient density and composition of membrane perturbing molecules such that the composition has a membrane perturbing effect on the target. Sufficiency of the density and composition of membrane perturbing molecules can be determined by assessing membrane disruption, apoptosis, and/or therapeutic effect on the target in a non-human animal.

The density of homing molecules and/or membrane perturbing molecules on a surface molecule can be described in any suitable manner. For example, the density can be expressed as the number of homing molecules and/or membrane perturbing molecules per, for example, a given area, surface area, volume, unit, subunit, arm, etc. of the surface molecule. The density can also be relative to, for example, the area, surface area, volume, unit, subunit, arm, etc. of the entire surface molecule or to the area, surface area, volume, unit, subunit, arm, etc. of a portion of the surface molecule. For example, a sufficient density of homing molecule and/or membrane perturbing molecule can be present in a portion of the surface molecule. The presence of this dense portion can cause clotting and amplify the accumulation of the composition. Thus, a composition having a sufficient density of homing molecules and/or membrane perturbing molecules can have a threshold density (or above) for the entire surface molecule or for just one or more portions of the surface molecule. Unless otherwise stated, densities refer to average density over the designated portion of the surface molecule. For example, a density of 1 homing molecule per square nM of the surface molecule refers to an average density of the homing molecules over the entire surface molecule. As another example, a density of 1 homing molecule per square nM of a portion of the surface molecule refers to an average density of the homing molecules over just that portion of the surface molecule.

The density can be measured or calculated in any suitable manner. For example, the number or amount of homing molecules and/or membrane perturbing molecules present on a surface molecule or group of surface molecules can be measured by, for example, detecting the level or intensity of signal produced by labeled homing molecules and/or membrane perturbing molecules and calculating the density based on the structural characteristics of the surface molecule.

The density or threshold density of homing molecules and/or membrane perturbing molecules can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 homing molecules and/or membrane perturbing molecules per square nM of the entire or a portion of the surface molecule. The composition can also comprise any density in between those densities listed above.

The density or threshold density of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules per square µM of the entire or a portion of the surface molecule. The composition can also comprise any density in between those densities listed above.

The density or threshold density of homing molecules and/or membrane perturbing molecules can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 homing molecules and/or membrane perturbing molecules per cubic nM of the entire or a portion of the surface molecule. The composition can also comprise any density in between those densities listed above.

The density or threshold density of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules per cubic µM of the entire or a portion of the surface molecule. The composition can also comprise any density in between those densities listed above.

The number of homing molecules and/or membrane perturbing molecules on a surface molecule can be described in any suitable manner. For example, the number can be expressed as the number of homing molecules and/or membrane perturbing molecules per, for example, a given area, surface area, volume, unit, subunit, arm, etc. of the surface molecule. The number can also be relative to, for example, the area, surface area, volume, unit, subunit, arm, etc. of the entire surface molecule or to the area, surface area, volume, unit, subunit, arm, etc. of a portion of the surface molecule. For example, a sufficient number of homing molecule and/or membrane perturbing molecule can be present in a portion of the surface molecule. The presence of this dense portion can cause clotting and amplify the accumulation of the composition. Thus, a composition having a sufficient number of homing molecules and/or membrane perturbing molecules can have a threshold number (or above) for the entire surface molecule or for just one or more portions of the surface molecule.

The number can be measured or calculated in any suitable manner. For example, the number or amount of homing molecules and/or membrane perturbing molecules present on a surface molecule or group of surface molecules can be measured by, for example, detecting the level or intensity of signal produced by labeled homing molecules and/or membrane perturbing molecules and calculating the number based on the structural characteristics of the surface molecule.

The number or threshold number of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules on the surface molecule. The composition can also comprise any number in between those numbers listed above.

The number or threshold number of homing molecules and/or membrane perturbing molecules can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 homing molecules and/or membrane perturbing molecules per square nM of the entire or a portion of the surface molecule. The composition can also comprise any number in between those numbers listed above.

The number or threshold number of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules per square µM of the entire or a portion of the surface molecule. The composition can also comprise any number in between those numbers listed above.

The number or threshold number of homing molecules and/or membrane perturbing molecules can be, for example, at least 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, or 1000 homing molecules and/or membrane perturbing molecules per cubic nM of the entire or a portion of the surface molecule. The composition can also comprise any number in between those numbers listed above.

The number or threshold number of homing molecules and/or membrane perturbing molecules can be, for example, at least 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 900, 9500, 10,000 homing molecules and/or membrane perturbing molecules per cubic µM of the entire or a portion of the surface molecule. The composition can also comprise any number in between those numbers listed above.

In some forms, the compositions not only home to tumors, but also amplify their own homing. Homing molecules can be used that are clot-binding compounds that recognize clotted plasma proteins and selectively homes to tumors, where it binds to vessel walls and tumor stroma. Surface molecules coupled with the clot-binding compounds can accumulate in tumor vessels or at wound sites, where they induce additional local clotting, thereby producing new binding sites for more particles. The system mimics platelets, which also circulate freely but accumulate at a diseased site and amplify their own accumulation at that site. The clotting-based amplification greatly enhances cargo delivery and tumor imaging.

Disclosed are linkers for associating components of the disclosed compositions. Such linkers can be any molecule, conjugate, composition, etc. that can be used to associate components of the disclosed compositions. Generally, linkers can be used to associate components other than surface molecules to surface molecules. Useful linkers include materials that are biocompatible, have low bioactivity, have low antigenicity, etc. That is, such useful linker materials can serve the linking/association function without adding unwanted bioreactivity to the disclosed compositions. Many such materials are know and used for similar linking and association functions. Polymer materials are a particularly useful form of linker material. For example, polyethylene glycols can be used.

Linkers are useful for achieving useful numbers and densities of the components (such as homing molecules and membrane perturbing molecules) on surface molecules. For example, linkers of fibrous form are useful for increasing the number of components per surface molecule or per a given area of the surface molecule. Similarly, linkers having a branching form are useful for increasing the number of components per surface molecule or per a given area of the surface molecule. Linkers can also have a branching fibrous form.

Linkers of different lengths can be used to bind the disclosed components to surface molecules and to each other. A flexible linker can function well even if relatively short, while a stiffer linker may can be longer to allow effective exposure and density. The length of a linker can refer to the number of atoms in a continuous covalent chain between the attachment points on the components being linked or to the length (in nanometers, for example) of a continuous covalent chain between the attachment points on the components being linked. Unless the context clearly indicates otherwise, the length refers to the shortest continuous covalent chain between the attachment points on the components being linked not accounting for side chains, branches, or loops. Due to flexibility of the linker, all of the linkers may not have same distance from the surface molecule. Thus linkers with different chain lengths can make the resulting composition more effective (by increasing density, for example). Branched linkers bearing multiple components also allow attachment of more than one component at a given site of the surface molecule. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 atoms. Useful lengths for linkers include at least, up to, about, exactly, or between 10, 15, 20, 25, 30, 35, 40, 45, 50, 60, 70, 80, 90, 100, 120, 140, 150, 160, 180, 200, 250, 300, 350, 400, 450, 500, 550, 600, 650, 700, 750, 800, 850, 900, 950, 1,000, 2,000, 3,000, 4,000, 5,000, 6,000, 7,000, 8,000, 9,000, and 10,000 nanometers. Any range of these lengths and all lengths between the listed lengths are specifically contemplated.

Hydrophilic or water-solubility linkers can increase the mobility of the attached components. Examples of water-soluble, biocompatible polymers which can serve as linkers include, but are not limited to polymers such polyethylene glycol (PEG), polyethylene oxide (PEO), polyvinyl alcohol, polyhydroxyethyl methacrylate, polyacrylamide, and natural polymers such as hyaluronic acid, chondroitin sulfate, carboxymethylcellulose, and starch. Useful forms of branched tethers include star PEO and comb PEO. Star PEO can be formed of many PEO "arms" emanating from a common core.

Polyethylene glycols (PEGs) are simple, neutral polyethers which have been given much attention in biotechnical and biomedical applications (Milton Harris, J. (ed) "Poly(ethylene glycol) chemistry, biotechnical and biomedical applications" Plenum Press, New York, 1992). PEGs are soluble in most solvents, including water, and are highly hydrated in aqueous environments, with two or three water molecules bound to each ethylene glycol segment; this hydration phenomenon has the effect of preventing adsorption either of other polymers or of proteins onto PEG-modified surfaces. Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes. Appropriate molecular weights for PEG linkers used in the disclosed compositions can be from about 120 daltons to about 20 kilodaltons. For example, PEGs can be at least, up to, about, exactly, or between 100, 150, 200, 250, 300, 350, 400, 450, 500, 600, 700, 800, 900, 1000, 1200, 1400, 1500, 1600, 1800, 2000, 2500, 3000, 3500, 4000, 4500, 5000, 5500, 6000, 6500, 7000, 7500, 8000, 8500, 9000, 9500, 10,000, 20,000, 30,000, 40,000, and 50,000 daltons. Any range of these masses and all masses between the listed masses are specifically contemplated. PEGs are usually available as mixtures of somewhat heterogeneous masses with a stated average mass (PEG-5000, for example).

The disclosed compositions can be produced using any suitable techniques. Many techniques, reactive groups, chemistries, etc. for linking components of the types disclosed herein are known and can be used with the disclosed components and compositions.

Protein crosslinkers that can be used to crosslink other molecules, elements, moieties, etc. to the disclosed compositions, surface molecules, homing molecules, membrane perturbing molecules, internalization elements, tissue penetration elements, cargo compositions, tLyP-1 peptides, compositions, peptides, amino acid sequences, etc. are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy)ethyl]sulfone), BSO-COES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio)propionamido]hexanoate), SULFO NHS LC SPDP (Sulfosuccinimidyl-6-[3-(2-pyridyldithio)propionamido)hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-p-hydroxybenzimidate hydrochloride, 98%), DMA (Dimethyladipimidate hydrochloride).

Components of the disclosed compositions, such as surface molecules, homing molecules, membrane perturbing molecules, internalization elements, tissue penetration elements, etc., can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide] (Avanti Polar Lipids) by making use of a free cysteine sulfhydryl group on the component. The reaction can be performed, for example, in aqueous solution at room temperature for 4 hours. This coupling chemistry can be used to couple components of co-compositions and cargo compositions.

Components of the disclosed compositions, such as surface molecules, homing molecules, membrane perturbing molecules, internalization elements, tissue penetration elements, etc., can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., Pharm. Rev. 53, 283-318 (2001)). The particles can have surface modifications, for example, for reticuloendothelial system avoidance (PEG) and homing (homing molecules), endosome escape (pH-sensitive peptide; for example, Pirollo et al., Cancer Res. 67, 2938-43 (2007)), a detectable agent, a therapeutic compound, or a combination. To accommodate all these functions on one particle, optimization studies can be conducted to determine what proportion of the available linking sites at the surface of the particles any one of these elements should occupy to give the best combination of targeting and payload delivery. The cell internalization and/or tissue penetration of such compositions can be mediated by the disclosed tLyP-1 peptides, amino acid sequences, proteins, molecules, conjugates, and compositions.

The provided peptides and polypeptides can have additional N-terminal, C-terminal, or intermediate amino acid sequences, e.g., amino acid linkers or tags. The term "amino acid linker" refers to an amino acid sequences or insertions that can be used to connect or separate two distinct peptides, polypeptides, or polypeptide fragments, where the linker does not otherwise contribute to the essential function of the composition. The term "amino acid tag" refers to a distinct amino acid sequence that can be used to detect or purify the provided polypeptide, wherein the tag does not otherwise contribute to the essential function of the composition. The provided peptides and polypeptides can further have deleted N-terminal, C-terminal or intermediate amino acids that do not contribute to the essential activity of the peptides and polypeptides.

Components can be directly or indirectly covalently bound to surface molecules or each other by any functional group (e.g., amine, carbonyl, carboxyl, aldehyde, alcohol). For example, one or more amine, alcohol or thiol groups on the components can be reacted directly with isothiocyanate, acyl azide, N-hydroxysuccinimide ester, aldehyde, epoxide, anhydride, lactone, or other functional groups incorporated onto the surface molecules or other components. Schiff bases formed between the amine groups on the components and aldehyde groups on the surface molecule or other components can be reduced with agents such as sodium cyanoborohydride to form hydrolytically stable amine links (Ferreira et al., J. Molecular Catalysis B: Enzymatic 2003, 21, 189-199). Components can be coupled to surface molecules and other components by, for example, the use of a heterobifunctional silane linker reagent, or by other reactions that activate functional groups on either the surface molecule or the components.

Useful modes for linking components to surface molecules and to tother components include heterobifunctional linkers or spacers. Such linkers can have both terminal amine and thiol reactive functional groups for reacting amines on components with sulfhydryl groups, thereby coupling the components in an oriented way. These linkers can contain a variable number of atoms. Examples of such linkers include, but are not limited to, N-Succinimidyl 3-(2-pyridyldithio)propionate (SPDP, 3- and 7-atom spacer), long-chain—SPDP (12-atom spacer), (Succinimidyloxycarbonyl-a-methyl-2-(2-pyridyldithio) toluene) (SMPT, 8-atom spacer), Succinimidyl-4-(N-maleimidomethyl)cyclohexane-1-carboxylate) (SMCC, 11-atom spacer) and Sulfosuccinimidyl-4-(N-maleimidomethyl)cyclohexane-1-carboxylate, (sulfo-SMCC, 11-atom spacer), m-Maleimidobenzoyl-N hydroxysuccinimide ester (MBS, 9-atom spacer), N-(g-maleimidobutryloxy)succinimide ester (GMBS, 8-atom spacer), N-(g-maleimidobutyryloxy) sulfosuccinimide ester (sulfo-GMBS, 8-atom spacer), Succinimidyl 6-((iodoacetyl) amino) hexanoate (SIAX, 9-atom spacer), Succinimidyl 6-(6-(((4-iodoacetyl)amino)hexanoyl)amino)hexanoate (SIAXX, 16-atom spacer), and p-nitrophenyl iodoacetate (NPIA, 2-atom spacer). One ordinarily skilled in the art also will recognize that a number of other coupling agents or links, with different number of atoms, may be used.

Hydrophilic spacer atoms can be incorporated into linkers to increase the distance between the reactive functional groups. For example, polyethylene glycol (PEG) can be incorporated into sulfo-GMBS. Hydrophilic molecules such as PEG have also been shown to decrease non-specific binding (NSB) and increase hydrophilicity of surfaces when covalently coupled. PEG can also be used as the primary linker material.

Free amine groups of components can also be attached to surface molecules or other components containing reactive amine groups via homobifunctional linkers. Linkers such as dithiobis(succinimidylpropionate) (DSP, 8-atom spacer), disuccinimidyl suberate (DSS, 8-atom spacer), glutaraldehyde (4-atom spacer), Bis[2-(succinimidyloxycarbonyloxy)ethyl]sulfone (BSOCOES, 9-atom spacer), all requiring high pH, can be used for this purpose. Examples of homobifunctional sulfhydryl-reactive linkers include, but are not limited to, 1,4-Di-[3'-2'-pyridyldithio)propion-amido]butane (DP-DPB, 16-atom spacer) and Bismaleimidohexane (BMH, 14-atom spacer). For example, these homobifunctional linkers are first reacted with a thiolated surface in aqueous solution (for example PBS, pH 7.4), and then in a second step, the thiolated antibody or protein is joined by the link. Homo- and heteromultifunctional linkers can also be used.

Direct binding of components to thiol, amine, or carboxylic acid functional groups on surface molecules and other components be used to produce compositions which exhibit viral binding (due to increased density of components, for example), resulting in enhanced sensitivity.

As an example, when necessary to achieve high peptide coupling density, additional amino groups can be added to the surface molecules (such as commercially obtained SPIO) as follows: First, to crosslink the particles before the amination step, 3 ml of the colloid (~10 mgFe/ml in double-distilled water) was added to 5 ml of 5M NaOH and 2 ml of epichlorohydrin (Sigma, St. Louis, Mo.). The mixture was agitated for 24 hours at room temperature to promote interaction between the organic phase (epichlorohydrin) and aqueous phase (dextran-coated particle colloid). In order to remove excess epichlorohydrin, the reacted mixture was dialyzed against double-distilled water for 24 hours using a dialysis cassette (10,000 Da cutoff, Pierce, Rockford Ill.). Amino groups were added to the surface of the particles as follows: 0.02 ml of concentrated ammonium hydroxide (30%) was added to 1 ml of colloid (~10 mg Fe/ml). The mixture was agitated at room temperature for 24 hours. The reacted mixture was dialyzed against double-distilled water for 24 hours. To further rinse the particles, the colloid was trapped on a MACS® Midi magnetic separation column (Miltenyi Biotec, Auburn Calif.), rinsed with PBS three times, and eluted from the column with 1 ml PBS.

To conjugate CGKRK peptide (and other peptides) to SPIO, the particles were re-suspended at a concentration of 1 mg Fe/ml, and heterobifunctional linker N-[a-maleimidoacetoxy]succinimide ester (AMAS; Pierce) was added (2.5 mg linker per 2 mg Fe) under vortexing. After incubation at room temperature for 40 min, the particles were washed 3 times with 10 ml PBS on a MACS column. The peptide with free terminal cysteine was then added (100 μg peptide per 2 mg Fe). After incubation overnight at 4° C. the particles were washed again and re-suspended in PBS at a concentration of 0.35 mg/ml of Fe). To quantify the number of peptide molecules conjugated to the particles, a known amount of stock or AMAS-activated particles was incubated with varying amounts of the peptide. After completion of the incubation the particles were pelleted at 100.000G using Beckman TLA 100.3 ultracentrifuge rotor (30 min) and the amount of the unbound peptide was quantified by fluorescence. To cleave the conjugated peptide from the particles, the particles were incubated at 37° C. overnight at pH 10. The concentration of free peptide in the supernatant was determined by reading fluorescence and by using the calibration curve obtained for the same peptide. The fluorescence intensity of known amounts of particles was plotted as a function of peptide conjugation density, and the slope equation was used to determine conjugation density in different batches.

Many homing molecules and homing peptides home to the vasculature of the target tissue. However, for the sake of convenience homing is referred to in some places herein as homing to the tissue associated with the vasculature to which the homing molecule or homing peptide may actually home. Thus, for example, a homing peptide that homes to tumor vasculature can be referred to herein as homing to tumor tissue or to tumor cells. By including or associating a homing molecule or homing peptide with, for example, a protein, peptide, amino acid sequence, co-composition, cargo composition, or tLyP-1 peptide the protein, peptide, amino acid sequence, co-composition, cargo composition, or tLyP-1 peptide can be targeted or can home to the target of the homing molecule or homing peptide. In this way, the protein, peptide, amino acid sequence, co-composition, cargo composition, or tLyP-1 peptide can be said to home to the target of the homing molecule or homing peptide. For convenience and unless otherwise indicated, reference to homing of a protein, peptide, amino acid sequence, co-composition, cargo composition, tLyP-1 peptide, etc. is intended to indicate that the protein, peptide, amino acid sequence, co-composition, cargo composition, tLyP-1 peptide, etc. includes or is associated with an appropriate homing molecule or homing peptide.

The homing molecule can selectively home to a tumor. The homing molecule can selectively home to tumor vasculature. The homing molecule can selectively home to one or more particular types of tumor. The homing molecule can selectively home to the vasculature of one or more particular types of tumor. The homing molecule can selectively home to one or more particular stages of a tumor or cancer. The homing molecule can selectively home to the vasculature of one or more particular stages of a tumor or cancer. The homing molecule can selectively home to one or more particular stages of one or more particular types of tumor. The homing molecule can selectively home to the vasculature of one or more different stages of one or more particular types of tumor.

The composition can selectively home to a tumor. The composition can selectively home to tumor vasculature. The composition can selectively home to one or more particular types of tumor. The composition can selectively home to the vasculature of one or more particular types of tumor. The composition can selectively home to one or more particular stages of a tumor or cancer. The composition can selectively home to the vasculature of one or more particular stages of a tumor or cancer. The composition can selectively home to one or more particular stages of one or more particular types of tumor. The composition can selectively home to the vasculature of one or more different stages of one or more particular types of tumor.

The co-composition can selectively home to a tumor. The co-composition can selectively home to tumor vasculature. The co-composition can selectively home to one or more particular types of tumor. The co-composition can selectively home to the vasculature of one or more particular types of tumor. The co-composition can selectively home to one or more particular stages of a tumor or cancer. The co-composition can selectively home to the vasculature of one or more particular stages of a tumor or cancer. The co-composition can selectively home to one or more particular stages of one or more particular types of tumor. The co-composition can selectively home to the vasculature of one or more different stages of one or more particular types of tumor.

The tLyP-1 composition can selectively home to a tumor. The tLyP-1 composition can selectively home to tumor vasculature. The tLyP-1 composition can selectively home to one or more particular types of tumor. The tLyP-1 composition can selectively home to the vasculature of one or more particular types of tumor. The tLyP-1 composition can selectively home to one or more particular stages of a tumor or cancer. The tLyP-1 composition can selectively home to the vasculature of one or more particular stages of a tumor or cancer. The tLyP-1 composition can selectively home to one or more particular stages of one or more particular types of tumor. The tLyP-1 composition can selectively home to the vasculature of one or more different stages of one or more particular types of tumor.

The tLyP-1 peptide can selectively home to a tumor. The tLyP-1 peptide can selectively home to tumor vasculature. The tLyP-1 peptide can selectively home to one or more particular types of tumor. The tLyP-1 peptide can selectively home to the vasculature of one or more particular types of tumor. The tLyP-1 peptide can selectively home to one or more particular stages of a tumor or cancer. The tLyP-1 peptide can selectively home to the vasculature of one or more particular stages of a tumor or cancer. The tLyP-1 peptide can selectively home to one or more particular stages of one or more particular types of tumor. The tLyP-1 peptide can selectively home to the vasculature of one or more different stages of one or more particular types of tumor.

The cargo composition can selectively home to a tumor. The cargo composition can selectively home to tumor vasculature. The cargo composition can selectively home to one or more particular types of tumor. The cargo composition can selectively home to the vasculature of one or more particular types of tumor. The cargo composition can selectively home to one or more particular stages of a tumor or cancer. The cargo composition can selectively home to the vasculature of one or more particular stages of a tumor or cancer. The cargo composition can selectively home to one or more particular stages of one or more particular types of tumor. The cargo composition can selectively home to the vasculature of one or more different stages of one or more particular types of tumor.

The cargo molecule can selectively home to a tumor. The cargo molecule can selectively home to tumor vasculature. The cargo molecule can selectively home to one or more particular types of tumor. The cargo molecule can selectively home to the vasculature of one or more particular types of tumor. The cargo molecule can selectively home to one or more particular stages of a tumor or cancer. The cargo molecule can selectively home to the vasculature of one or more particular stages of a tumor or cancer. The cargo molecule can selectively home to one or more particular stages of one or more particular types of tumor. The cargo molecule can selectively home to the vasculature of one or more different stages of one or more particular types of tumor.

The surface molecule can selectively home to a tumor. The surface molecule can selectively home to tumor vasculature. The surface molecule can selectively home to one or more particular types of tumor. The surface molecule can selectively home to the vasculature of one or more particular types of tumor. The surface molecule can selectively home to one or more particular stages of a tumor or cancer. The surface molecule can selectively home to the vasculature of one or more particular stages of a tumor or cancer. The surface molecule can selectively home to one or more particular stages of one or more particular types of tumor. The surface molecule can selectively home to the vasculature of one or more different stages of one or more particular types of tumor.

The membrane perturbing molecule can selectively home to a tumor. The membrane perturbing molecule can selectively home to tumor vasculature. The membrane perturbing molecule can selectively home to one or more particular types of tumor. The membrane perturbing molecule can selectively home to the vasculature of one or more particular types of tumor. The membrane perturbing molecule can selectively home to one or more particular stages of a tumor or cancer. The membrane perturbing molecule can selectively home to the vasculature of one or more particular stages of a tumor or cancer. The membrane perturbing molecule can selectively home to one or more particular stages of one or more particular types of tumor. The membrane perturbing molecule can selectively home to the vasculature of one or more different stages of one or more particular types of tumor.

The disclosed amino acid sequences, co-compositions, cargo compositions, proteins or peptides can, for example, home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

Examples of homing molecules and homing peptides are known. Examples include: Brain homing peptides such as: CNSRLHLRC (SEQ ID NO:114), CENWWGDVC (SEQ ID NO:115), WRCVLREGPAGGCAWFNRHRL (SEQ ID NO:116), CLSSRLDAC (SEQ ID NO:117), CVLRGGRC (SEQ ID NO:118), CNSRLQLRC (SEQ ID NO:119), CGVRLGC (SEQ ID NO:120), CKDWGRIC (SEQ ID NO:121), CLDWGRIC (SEQ ID NO:122), CTRITESC (SEQ ID NO:123), CETLPAC (SEQ ID NO:124), CRTGTLFC (SEQ ID NO:125), CGRSLDAC (SEQ ID NO:126), CRHWFDVVC (SEQ ID NO:127), CANAQSHC (SEQ ID NO:128), CGNPSYRC (SEQ ID NO:129), YPCGGEAVAGVSSVRTMCSE (SEQ ID NO:130), LNCDYQGTNPATSVSVPCTV (SEQ ID NO:131); kidney homing peptides such as: CLPVASC (SEQ ID NO:132), CGAREMC (SEQ ID NO:133), CKGRSSAC (SEQ ID NO:134), CWARAQGC (SEQ ID NO:135), CLGRSSVC (SEQ ID NO:136), CTSPGGSC (SEQ ID NO:137), CMGRWRLC (SEQ ID NO:138), CVGECGGC (SEQ ID NO:139), CVAWLNC (SEQ ID NO:140), CRRFQDC (SEQ ID NO:141), CLMGVHC (SEQ ID NO:142), CKLLSGVC (SEQ ID NO:143), CFVGHDLC (SEQ ID NO:144), CRCLNVC (SEQ ID NO:145), CKLMGEC (SEQ ID NO:146); skin homing peptides such as: CARSKNKDC (SEQ ID NO:147), CRKDKC (SEQ ID NO:2), CVALCREACGEGC (SEQ ID NO:149), CSSGCSKNCLEMC (SEQ ID NO:150), CIGEVEVC (SEQ ID NO:151), CKWSRLHSC (SEQ ID NO:152), CWRGDRKIC (SEQ ID NO:153), CERVVGSSC (SEQ ID NO:154), CLAKENVVC (SEQ ID NO:155); lung homing peptides such as: CGFECVRQCPERC (SEQ ID NO:156), CGFELETC (SEQ ID NO:157), CTLRDRNC (SEQ ID NO:158), CIGEVEVC (SEQ ID NO:151), CGKRYRNC (SEQ ID NO:161), CLRPYLNC (SEQ ID NO:162), CTVNEAYKTRMC (SEQ ID NO:163), CRLRSYGTLSLC (SEQ ID NO:164), CRPWHNQAHTEC (SEQ ID NO:165); pancreas homing peptides such as: SWCEPGWCR (SEQ ID NO:166), CKAAKNK (SEQ ID NO:167), CKGAKAR (SEQ ID NO:168), VGVGEWSV (SEQ ID NO:169); intestine homing peptides such as: YSGKWGW (SEQ ID NO:170); uterus homing peptides such as: GLSGGRS (SEQ ID NO:171); adrenal gland homing peptides such as: LMLPRAD (SEQ ID NO:172), LPRYLLS (SEQ ID NO:173); retina homing peptides such as: CSCFRDVCC (SEQ ID NO:174), CRDVVSVIC (SEQ ID NO:175); gut homing peptides such as: YSGKWGK (SEQ ID NO:176), GISALVLS (SEQ ID NO:177), SRRQPLS (SEQ ID NO:178), MSPQLAT (SEQ ID NO:179), MRRDEQR (SEQ ID NO:180), QVRRVPE (SEQ ID NO:181), VRRGSPQ (SEQ ID NO:182), GGRGSWE (SEQ ID NO:183), FRVRGSP (SEQ ID NO:184), RVRGPER (SEQ ID NO:185); liver homing peptides such as: VKSVCRT (SEQ ID NO:186), WRQNMPL (SEQ ID NO:187), SRRFVGG (SEQ ID NO:188), ALERRSL (SEQ ID NO:189), ARRGWTL (SEQ ID NO:190); prostate homing peptides such as: SMSIARL (SEQ ID NO:191), VSFLEYR (SEQ ID NO:192), RGRWLAL (SEQ ID NO:193); ovary homing peptides such as: EVRSRLS (SEQ ID NO:194), VRARLMS (SEQ ID NO:195), RVGLVAR (SEQ ID NO:196), RVRLVNL (SEQ ID NO:197); Clot binding homing peptide such as: CREKA (SEQ ID NO:12), CLOT1, and CLOT2; heart homing peptides such as: CRPPR (SEQ ID NO:198), CGRKSKTVC (SEQ ID NO:199), CARPAR (SEQ ID NO:200), CPKRPR (SEQ ID NO:46), CKRAVR (SEQ ID NO:20), CRNSWKPNC (SEQ ID NO:21), RGSSS (SEQ ID NO:23), CRSTRANPC (SEQ ID NO:16), CPKTRRVPC (SEQ ID NO:17), CSGMARTKC (SEQ ID NO:45), GGGVFWQ (SEQ ID NO:61), HGRVRPH (SEQ ID NO:107), VVLVTSS (SEQ ID NO:148), CLHRGNSC (SEQ ID NO:159), CRSWNKADNRSC (SEQ ID NO:160), CGRKSKTVC (SEQ ID NO:199), CKRAVR (SEQ ID NO:20), CRNSWKPNC (SEQ ID NO:21), CPKTRRVPC (SEQ ID NO:17), CSGMARTKC (SEQ ID NO:45), CARPAR (SEQ ID NO:200), CPKRPR (SEQ ID NO:46); tumor blood vessel homing peptide such as: CNGRC (SEQ ID NO:68) and other peptides with the NGR motif (U.S. Pat. Nos. 6,177,542 and 6,576,239; U.S. Patent Application Publication No. 20090257951); RGD peptides, and RGR peptides. Other homing peptides include CSRPRRSEC (SEQ ID NO:108), CSRPRRSVC (SEQ ID NO:109) and CSRPRRSWC (SEQ ID NO:110) (Hoffman et al., Cancer Cell, vol. 4 (2003)), F3 (KDEPQRRSARLSAKPAPPKPEPKPKKAPAKK; (SEQ ID NO:111)), PQRRSARLSA (SEQ ID NO:112), PKRRSARLSA (SEQ ID NO:113) (U.S. Pat. No. 7,544,767), and CGRECPRLCQSSC (SEQ ID NO:62), which home to tumors.

Homing molecules can also be defined by their targets. For example, numerous antigens and proteins are known that can be useful for targeting. Any molecule that can bind, selectively bind, home, selectively, target, selectively target, etc. such target molecules can be used as a homing molecule. For example, antibodies, nucleic acid aptamers, and compounds that can bind to target molecules can be used as homing molecules. Examples of useful target molecules for homing molecules include αv integrins, αvβ3 integrin, αvl5 integrin, α5β1 integrin, aminopeptidase N, tumor endothelial markers (TEMs), endosialin, p32, gC1q receptor, annexin-1, nucleolin, fibronectin ED-B, fibrin-fibronectin complexes, interleukin-11 receptor α, and protease-cleaved collagen IV. These and other examples are described and referred to in Ruoslahti et al., J. Cell Biology, 2010 (doi: 10.1083/jbc.200910104), which is hereby incorporated by reference in its entirety and specifically for its description of and references to target molecules.

The composition, tLyP-1 composition, co-composition, or cargo composition can comprise any number of homing molecules. By way of example, the composition, tLyP-1 composition, co-composition, or cargo composition can comprise at least 1, 5, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 625, 750, 775, 800, 825, 850, 875, 900, 925, 950, 975, 1000, 1100, 1200, 1300, 1400, 1500, 1600, 1700, 1800, 1900, 2000, 2250, 2500, 2750, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 75,000, or 100,000, or more homing molecules. The composition, tLyP-1 composition, co-composition, or cargo composition can also comprise any number in between those numbers listed above.

It is understood that, although many homing and targeting motifs and sequences are shown with cysteine residues at one or both ends, such cysteine residues are generally not required for homing function. Generally, such cysteines are present due to the methods by which the homing and targeting sequences were identified. Such terminal cysteines can be used to, for example, circularize peptides, such as those disclosed herein. For these reasons, it is also understood that cysteine residues can be added to the ends of any of the disclosed peptides.

Useful NGR peptides include peptide such as $X_2CNGRCX_2$ (SEQ ID NO:89), $CX_2(C/X)NGR(C/X)X_2C$ (SEQ ID NO:90), and $CNGRCX_6$ (SEQ ID NO:91) (where "X" is any amino acid), which can be linear or circular. Examples of NGR peptides include CNGRCVSGCAGRC (SEQ ID NO:63), NGRAHA (SEQ ID NO:24), CVLNGRMEC (SEQ ID NO:67), CNGRC (SEQ ID NO:68), ALNGREESP (SEQ ID NO:66), CVLNGRME (SEQ ID NO:87), CKVCNGRCCG (SEQ ID NO:88), CEMCNGRCMG (SEQ ID NO:69), CPLCNGRCAL (SEQ ID NO:70), CPTCNGRCVR (SEQ ID NO:71), CGVCNGRCGL (SEQ ID NO:72), CEQCNGRCGQ (SEQ ID NO:73), CRNCNGRCEG (SEQ ID NO:74), CVLCNGRCWS (SEQ ID NO:75), CVTCNGRCRV (SEQ ID NO:76), CTECNGRCQL (SEQ ID NO:77), CRTCNGRCLE (SEQ ID NO:78), CETCNGRCVG (SEQ ID NO:79), CAVCNGRCGF (SEQ ID NO:80), CRDLNGRKVM (SEQ ID NO:81), CSCCNGRCGD (SEQ ID NO:82), CWGCNGRCRM (SEQ ID NO:83), CPLCNGRCAR (SEQ ID NO:84), CKSCNGRCLA (SEQ ID NO:85), CVPCNGRCHE (SEQ ID NO:86), CQSCNGRCVR (SEQ ID NO:47), CRTCNGRCQV (SEQ ID NO:48), CVQCNGRCAL (SEQ ID NO:49), CRCCNGRCSP (SEQ ID NO:50), CASNNGRVVL (SEQ ID NO:51), CGRCNGRCLL (SEQ ID NO:52), CWLCNGRCGR (SEQ ID NO:53), CSKCNGRCGH (SEQ ID NO:54), CVWCNGRCGL (SEQ ID NO:55), CIRCNGRCSV (SEQ ID NO:56), CGECNGRCVE (SEQ ID NO:57), CEGVNGRRLR (SEQ ID NO:58), CLSCNGRCPS (SEQ ID NO:59), CEVCNGRCAL (SEQ ID NO:60).

Useful peptides for tumor targeting include, for example, iRGD, LyP-1, iNGR, and RGR peptides. The prototypic tumor-homing CendR peptide, iRGD, which was used in generating the results described herein. LyP-1 has tumor-penetrating properties. This peptide has a unique target within tumors; it preferentially accumulates in the hypoxic/low nutrient areas of tumors (Laakkonen et al., 2002; 2004; Karmali et al., 2009). CRGRRST (RGR; Joyce et al., 2003) is a peptide that has been successfully used in targeting a cytokine antibody combination into tumors (Hamzah et al., 2008). This peptide is linear, which simplifies the synthesis. NGR peptides home to angiogenic vasculature, including angiogenic vasculature associated with tumors, and $\alpha_v$ integrin and $\alpha_5\beta_1$ integrin (U.S. Pat. Nos. 6,576,239 and 6,177,542 and U.S. Patent Application Publication No. 20090257951). Like LyP-1, RGR is at least to some extent tumor type-specific (Joyce et al., 2003), but the tumor types recognized by the two peptides seem to be partially different, which may be an advantage in testing combinations with the pan-tumor iRGD.

RGD peptides are peptides that contain the RGD (Arg-Gly-Asp) motif and that home to angiogenesis and tumor vasculature. NGR peptides are peptides that contain the NGR (Asn-Gly-Arg) motif and that home to angiogenesis and tumor vasculature. Examples of NGR peptides include CNGRCVSGCAGRC (SEQ ID NO:63), NGRAHA (SEQ ID NO:24), CVLNGRMEC (SEQ ID NO:67), and CNGRC (SEQ ID NO:68). GSL peptides are peptides that contain the GSL (Gly-Ser-Leu) motif and that home to tumor vasculature. Examples of a GSL peptide include CGSLVRC (SEQ ID NO:65) and CLSGSLSC (SEQ ID NO:64).

Internalizing RGD (iRGD) refers to peptides that combine an RGD motif and a CendR element. For example, cyclic RGD peptide having the sequence CRGDK/RGPD/EC (SEQ ID NO:11) is exceptionally effective in orchestrating extravasation and spreading of linked payloads within tumor tissue, and subsequently internalizing within tumor cells. The iRGD peptide incorporates two functional elements: the RGD motif that gives tumor specificity (Pierschbacher and Ruoslahti, E. Cell attachment activity of fibronectin can be duplicated by small synthetic fragments of the molecule. Nature 309, 30-33 (1984); Ruoslahti (2003); Eliceiri and Cheresh (2001); Ruoslahti (2002); Arap et al. (1998); Curnis et al. (2004); Sipkins et al. (1998); Murphy et al. (2008)), and a CendR motif that mediates penetration. iRGD readily adheres to cultured cells expressing av integrins, and is internalized far more effectively than other RGD peptides. Internalization was dependent on expression of neuropilin-1, the receptor for the CendR motif. iRGD coupled to a payload of fluorescein, phage, or artificial nanoparticles, accumulated around tumor vessels in vivo, spread through the tumor interstitium, and became internalized within tumor cells in various tumor models. Systemic administration of iRGD micelles labeled with a near infrared dye produced a strong and specific tumor signal in whole body imaging of mice. The CendR element in iRGD is an activatable CendR element that is activated, likely by cleavage after the Lys/Arg, to allow the peptide to mediate internalization.

Internalizing NGR (iNGR) refers to peptides that combine a NGR motif and a CendR element. For example, NGR peptide having the sequence K/RNGR can be effective in orchestrating extravasation and spreading of linked payloads within tumor tissue, and subsequently internalizing within tumor cells. The iNGR peptide incorporates two functional elements: the NGR motif that gives tumor specificity, and a CendR motif that mediates penetration. Another example of an iNGR peptide is NGRAHA (SEQ ID NO:24). The CendR element in the iNGR peptide NGRAHA (SEQ ID NO:24) is an activatable CendR element that is activated, likely by cleavage after the Arg, to allow the peptide to mediate internalization.

Accessory molecules can be any molecule, compound, component, etc. that has a useful function and that can be used in combination with a tLyP-1 composition, tLyP-1 conjugate, tLyP-1 molecule, tLyP-1 protein, tLyP-1 peptide, composition, co-composition, and/or cargo composition. Examples of useful accessory molecules include homing molecules, targeting molecules, affinity ligands, cell penetrating molecules, endosomal escape molecules, subcellular targeting molecules, nuclear targeting molecules. Different accessory molecules can have similar or different functions from each other.

Molecules that target, home, or have affinity for certain molecules, structures, cells, tissues, etc. are particularly useful as accessory molecules. In addition to the homing peptides described elsewhere herein, there are numerous molecules and compounds known that have affinity for particular target molecules, structures, cells, tissues, etc. and can aid in accumulating and/or directing the disclosed components and compositions to desired targets. For convenience, such affinity effects can be referred to as homing. Descriptions of homing and homing effects elsewhere herein can be applied to these molecules.

An affinity ligand is a molecule that interacts specifically with a particular molecule, moiety, cell tissue, etc. The molecule, moiety, cell tissue, etc. that interacts specifically with an affinity ligand is referred to herein as a target or target molecule, moiety, cell tissue, etc. It is to be understood that the term target molecule refers to both separate molecules and to portions of such molecules, such as an epitope of a protein, that interacts specifically with an affinity ligand. Antibodies, either member of a receptor/ligand pair, synthetic polyamides (Dervan and Burli, *Sequence-specific DNA recognition by polyamides*. Curr Opin Chem Biol, 3(6):688-93 (1999); Wemmer and Dervan, *Targeting the minor groove of DNA*. Curr Opin Struct Biol, 7(3):355-61 (1997)), and other molecules with specific binding affinities are examples of affinity ligands.

An affinity ligand that interacts specifically with a particular target molecule is said to be specific for that target molecule. For example, where the affinity ligand is an antibody that binds to a particular antigen, the affinity ligand is said to be specific for that antigen. The antigen is the target molecule. The affinity ligand can also be referred to as being specific for a particular target molecule. Examples of useful affinity ligands are antibodies, ligands, binding proteins, receptor proteins, haptens, aptamers, carbohydrates, lectins, folic acid, synthetic polyamides, and oligonucleotides. Useful binding proteins include DNA binding proteins. Useful DNA binding proteins include zinc finger motifs, leucine zipper motifs, and helix-turn-helix motifs. These motifs can be combined in the same affinity ligand.

Antibodies are useful as the affinity ligands. Antibodies can be obtained commercially or produced using well established methods. For example, Johnstone and Thorpe, *Immunochemistry In Practice* (Blackwell Scientific Publications, Oxford, England, 1987) on pages 30-85, describe general methods useful for producing both polyclonal and monoclonal antibodies. The entire book describes many general techniques and principles for the use of antibodies in assay systems. Numerous antibodies and other affinity ligands are known that bind to particular proteins, carbohydrates, glycoproteins, molecules, cells, tissues, etc. Such antibodies can be used in the disclosed components and compositions.

Examples of cell penetrating peptides are described in, for example, U.S. Patent Application Publication Nos. 20100061942, 20100061932, 20100048487, 20100022466, 20100016215, 20090280058, 20090186802, 20080234183, 20060014712, 20050260756, and 20030077289, which are hereby incorporated by reference in their entirety and specifically for their description of cell penetrating peptides and motifs. Examples of endosomal escape molecules are described in, for example, U.S. Patent Application Publication Nos. 20090325866, 20090317802, 20080305119, 20070292920, 20060147997, 20050038239, 20040219169, 20030148263, 20030082143, 20020132990, and 20020068272, which are hereby incorporated by reference in their entirety and specifically for their description of endosomal escape molecules and motifs. Examples of subcellular targeting molecules are described in, for example, U.S. Patent Application Publication Nos. 2009031733, 20090258926, 20090176660, 20080311136, 20070287680, 20070157328, 20070111270, 20070111251, 20060257942, 20060154340, 20060014712, 20050281805, 20050233356, 20040005309, 20030082176, and 20010021500, which are hereby incorporated by reference in their entirety and specifically for their description of subcellular targeting molecules and motifs. Examples of nuclear targeting molecules are described in, for example, U.S. Patent Application Publication Nos. 10100143454, 20100099627, 20090305329, 20090176710, 20090087899, 20070231862, 20070212332, 20060242725, 20060233807, 20060147922, 20060070133, 20060051315, 20050147993, 20050071088, 20030166601, 20030125283, 20030083261, 20030003100, 20020068272, and 20020055174, which are hereby incorporated by reference in their entirety and specifically for their description of nuclear targeting molecules and motifs.

As disclosed herein, the term "co-composition" refers to any composition of matter that can be used with the tLyP-1 peptide. Similarly, the term "cargo composition" refers to any composition of matter that can be used with the tLyP-1 peptide. Generally, for example, a co-composition or cargo composition can be any composition to be internalized and/or to penetrate into cells and/or tissues. For example, a co-composition or cargo composition can be a molecule, a conjugate, an association of molecules, a composition, a mixture. Examples of co-compositions and cargo compositions include, but are not limited to, cancer chemotherapeutic agents, cytotoxic agents, anti-inflammatory agents, anti-arthritic agents, polypeptides, nucleic acid molecules, small molecules, nanoparticles, microparticles, fluorophores, fluorescein, rhodamine, a radionuclide, Lutetium-177 ($^{177}$Lu), Rhenium-188 ($^{188}$Re), Gallium-68 ($^{68}$Ga), Yttrium-90 ($^{90}$Y), Technetium-99m ($^{99m}$Tc), Holmium-166 ($^{166}$Ho), Iodine-131 ($^{131}$I), Indium-111 ($^{111}$In), Flourine-18 ($^{18}$F), Carbon-11 ($^{11}$C), Nitrogen-13 ($^{13}$N), Oxygen-15 ($^{15}$O), Bromine-75 ($^{75}$Br), Bromine-76 ($^{76}$Br), Iodine-124 ($^{124}$I), Thalium-201 ($^{201}$Tl), Technetium-99 ($^{99}$Tc), Iodine-123 ($^{123}$I), an anti-angiogenic agents, pro-angiogenic agents, or a combination thereof.

The disclosed tLyP-1 components can be used with any therapeutic agents since they represent a general mode and platform for aiding in delivery of therapeutic agents to cells and tissues. Thus, any therapeutic agent can be used in or with the disclosed compositions. Comprehensive lists of therapeutic agents and drugs can be found in a number of places, such as the Orange Book and other lists maintained by the U.S. Food and Drug Administration (information available at websites fda.gov/Drugs/InformationOnDrugs/ucm129662.htm and fda.gov/Drugs/InformationOnDrugs/ApprovedDrugs/default.htm) and similar lists maintained by other countries, and at clinicaltrials.gov/ (for drugs and therapeutic agents undergoing clinical trials).

Co-compositions and cargo compositions can be moieties. As used herein, the term "moiety" is used broadly to mean a physical, chemical, or biological material that generally imparts a biologically useful function to a linked co-composition or a linked cargo composition. A moiety can be any natural or nonnatural material including, without limitation, a biological material, such as a cell, phage or other virus; an organic chemical such as a small molecule; a nanoparticle, a radionuclide; a nucleic acid molecule or oligonucleotide; a polypeptide; or a peptide. For example, moieties that affect the target, such as moieties with therapeutic effect, or that facilitate detection, visualization or imaging of the target, such as fluorescent molecule or radionuclides.

Components of the disclosed co-compositions and cargo compositions can be combined, linked and/or coupled in any suitable manner. For example, moieties and other molecules can be associated covalently or non-covalently, directly or indirectly, with or without a linker moiety.

In some embodiments, a co-composition or cargo composition can comprise a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab; paclitaxel such as Abraxane; Doxil.

A co-composition or cargo composition can comprise a therapeutic agent. Useful therapeutic agents can be, for example, a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed compositions and methods.

In some forms, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon-α. (IFN-α); interferon-γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art. It is understood that these and other polypeptides with biological activity can be a "therapeutic polypeptide."

A therapeutic agent useful in the disclosed co-compositions and cargo compositions can be an anti-angiogenic agent. As used herein, the term "anti-angiogenic agent" means a molecule that reduces or prevents angiogenesis, which is the growth and development of blood vessels. The co-compositions and cargo compositions can be used to treat or diagnose any disease, condition, or disorder associated with angiogenesis. For example, macular degeneration and diabetic vascular complications can be diagnosed and/or treated. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Some other examples of useful therapeutic agents include nitrogen mustards, nitrosoureas, ethyleneimine, alkane sulfonates, tetrazine, platinum compounds, pyrimidine analogs, purine analogs, antimetabolites, folate analogs, anthracyclines, taxanes, *vinca* alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Chlomaphazine, Cholophosphamide, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Estramustine, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, mechlorethamine oxide hydrochloride, Melphalan, Mercaptopurine, Methotrexate, Mitomycin, Mitotane, Mitoxantrone, Novembiehin, Oxaliplatin, Paclitaxel, Pamidronate, Pentostatin, Phenesterine, Plicamycin, Prednimustine, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Trofosfamide, Vinblastine, Vincristine, Vindesine, Vinorelbine, VP-16, and Xeloda. Alkylating agents such as Thiotepa and; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above. Useful co-compositions and cargo compositions include, for example, doxorubicin, Herceptin, and liposomal doxorubicin.

The co-composition or cargo composition can also comprise a boron containing compound. Boron containing compounds have received increasing attention as therapeutic agents over the past few years as technology in organic synthesis has expanded to include this atom (Boron Therapeutics on the horizon, Groziak, M. P.; American Journal of Therapeutics (2001) 8, 321-328). The most notable boron containing therapeutic is the boronic acid bortezomib which was recently launched for the treatment of multiple myeloma. This breakthrough demonstrates the feasibility of using boron containing compounds as pharmaceutical agents. Boron containing compounds have been shown to have various biological activities including herbicides (Organic boron compounds as herbicides. Barnsley, G. E.; Eaton, J. K.; Airs, R. S.; (1957), DE 1016978 19571003), boron neutron capture therapy (Molecular Design and Synthesis of B-10 Carriers for Neutron Capture Therapy. Yamamoto, Y.; Pure Appl. Chem., (1991) 63, 423-426), serine protease inhibition (Borinic acid inhibitors as probes of the factors involved in binding at the active sites of subtilisin Carlsberg and .alpha.-chymotrypsin. Simpelkamp, J.; Jones, J. B.; Bioorganic & Medicinal Chemistry Letters, (1992), 2(11), 1391-4; Design, Synthesis and Biological Evaluation of Selective Boron-containing Thrombin Inhibitors. Weinand, A.; Ehrhardt, C.; Metternich, R.; Tapparelli, C.; Bioorganic and Medicinal Chemistry, (1999), 7, 1295-1307), acetylcholinesterase inhibition (New, specific and reversible bifunctional alkylborinic acid inhibitor of acetylcholinesterase. Koehler, K. A.; Hess, G. P.; Biochemistry (1974), 13, 5345-50) and as antibacterial agents (Boron-Containing Antibacterial Agents: Effects on Growth and Morphology of Bacteria Under Various Culture Conditions. Bailey, P. J.; Cousins, G.; Snow, G. A.; and White, A. J.; Antimicrobial Agents and Chemotherapy, (1980), 17, 549-553). The boron containing compounds with antibacterial activity can be sub-divided into two main classes, the diazaborinines, which have been known since the 1960's, and dithienylborinic acid complexes. This latter class has been expanded to include many different diarylborinic acid complexes with potent antibacterial activity (Preparation of diarylborinic acid esters as DNA methyl transferase inhibitors. Benkovic, S. J.; Shapiro, L.; Baker, S. J.; Wahnon, D. C.; Wall, M.; Shier, V. K.; Scott, C. P.; Baboval, J.; PCT Int. Appl. (2002), WO 2002044184).

The co-composition or cargo composition can also have one or more isotopes. Such isotopes can be useful, for example, as a therapeutic agent, as a detectable agent, or both. Examples of useful isopes include Lutetium-177 ($^{177}$Lu), Rhenium-188 ($^{188}$Re), Gallium-68 ($^{68}$Ga), Yttrium-90 ($^{90}$Y), Technetium-99m ($^{99m}$Tc), Holmium-166 ($^{166}$Ho), Iodine-131 ($^{131}$I), Indium-111 ($^{111}$In)Flourine-18 ($^{18}$F), Carbon-11 ($^{11}$C) Nitrogen-13 ($^{13}$N), Oxygen-15 ($^{15}$O), Bromine-75 ($^{75}$Br), Bromine-76 ($^{76}$Br), Iodine-124 ($^{124}$I), Thalium-201 ($^{201}$Tl), Technetium-99 ($^{99}$Tc), and Iodine-123 ($^{123}$I).

The co-composition or cargo composition can also comprise a detectable agent. A variety of detectable agents are useful in the disclosed methods. As used herein, the term "detectable agent" refers to any molecule which can be detected. Useful detectable agents include moieties that can be administered in vivo and subsequently detected. Detectable agents useful in the disclosed compositions and imaging methods include yet are not limited to radiolabels and fluorescent molecules. The detectable agent can be, for example, any moiety that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrast agent. The contrast agent can be, for example, Feridex. In some embodiments, for instance, the detectable agent comprises a tantalum compound. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, iron oxide and Gd can be used as a non-radioactive detectable agent in certain embodiments. Detectable agents can also include radioactive isotopes, enzymes, fluorophores, and quantum dots (Qdot®). For example, the detection moiety can be an enzyme, biotin, metal, or epitope tag. Other known or newly discovered detectable markers are contemplated for use with the provided compositions. In some embodiments, for instance, the detectable agent comprises a barium compound, e.g., barium sulfate.

The detectable agent can be (or the co-composition or cargo composition can include) one or more imaging agents. Examples of imaging agents include radiologic contrast agent, such as diatrizoic acid sodium salt dihydrate, iodine, and barium sulfate, a fluorescing imaging agent, such as Lissamine Rhodamine PE, a fluorescent or non-fluorescent stain or dye, for example, that can impart a visible color or that reflects a characteristic spectrum of electromagnetic radiation at visible or other wavelengths, for example, infrared or ultraviolet, such as Rhodamine, a radioisotope, a positron-emitting isotope, such as $^{18}$F or $^{124}$I (although the short half-life of a positron-emitting isotope may impose some limitations), a metal, a ferromagnetic compound, a paramagnetic compound, such as gadolinium, a superparamagnetic compound, such as iron oxide, and a diamagnetic compound, such as barium sulfate. Imaging agents can be selected to optimize the usefulness of an image produced by a chosen imaging technology. For example, the imaging agent can be selected to enhance the contrast between a feature of interest, such as a gastrointestinal polyp, and normal gastrointestinal tissue. Imaging can be accomplished using any suitable imaging techniques such as X-Ray, computed tomography (CT), MRI, Positron Emission Tomography (PET) or SPECT. In some forms, the co-composition or cargo composition can be coupled to a nuclear medicine imaging agent such as Indium-III or Technetium-99, to PET imaging agents, or to MRI imaging agents such as nanoparticles.

Examples of imaging techniques include magnetic resonance imaging (MRI), computerized tomography (CT), single photon emission computerized tomography (SPECT), and positron emission tomography (PET). Imaging agents generally can be classified as either being diagnostic or therapeutic in their application. Because of radiation's damaging effect on tissues, it is useful to target the biodistribution of radiopharmaceuticals as accurately as possible. PET can use imaging agents labeled with, for example, the positron-emitters such as $^{18}$F, $^{11}$C, $^{13}$N and $^{15}$O, $^{75}$Br, $^{76}$Br and $^{124}$I. SPECT can use imaging agents labeled with, for example, the single-photon-emitters such as $^{201}$Tl, $^{99}$Tc, $^{123}$I, and $^{131}$I.

Glucose-based and amino acid-based compounds can be used as imaging agents. Amino acid-based compounds are more useful in analyzing tumor cells, due to their faster uptake and incorporation into protein synthesis. Of the amino acid-based compounds, $^{11}$C- and $^{18}$F-containing compounds have been used with success. $^{11}$C-containing radiolabeled amino acids suitable for imaging include, for example, L[1-$^{11}$C]leucine (Keen et al. J. Cereb. Blood Flow Metab. 1989 (9):429-45), L[1-$^{11}$C]tyrosine (Wiesel et al. J. Nucl. Med. 1991 (32):2041-49), L[methyl-$^{11}$C]methionine (Comar et al. Eur. J. Nucl. Med. 1976 (1):11-14) and L[1-$^{11}$C]methionine (Bolster et al. Appl. Radiat. Isot. 1986 (37):1069-70).

PET involves the detection of gamma rays in the form of annihilation photons from short-lived positron emitting radioactive isotopes including, but not limited to, $^{18}$F with a half-life of approximately 110 minutes, $^{11}$C with a half-life of approximately 20 minutes, $^{13}$N with a half-life of approximately 10 minutes and $^{15}$O with a half-life of approximately 2 minutes, using the coincidence method. For PET imaging studies, compounds such as [$^{11}$C]meta-hydroxyephedrine (HED) and 2-[$^{18}$F]fluoro-2-deoxy-D-glucose (FDG) can be used. SPECT can use longer-lived isotopes including, but not limited to, $^{99m}$Tc with a half-life of approximately 6 hours and $^{201}$Tl with a half-life of approximately 74 hours. Radio-iodinated meta-iodobenzylguanidine (MIBG) is a radiotracing agent that can be used in nuclear medicine imaging studies.

The disclosed tLyP-1 compositions and co-compositions and cargo compositions can be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

The tLyP-1 compositions and co-compositions and cargo compositions can be used therapeutically in combination with a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

The preparation can be administered to a subject or organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to a subject or organism.

Herein the term "active ingredient" refers to the preparation accountable for the biological effect. For example tLyP-1 peptides, tLyP-1 compositions, tLyP-1 conjugates, tLyP-1 molecules, tLyP-1 proteins, compositions, co-compositions, and cargo compositions that have a biological effect can be considered active ingredients.

As used herein, the phrases "physiologically acceptable carrier" and "pharmaceutically acceptable carrier" which can be interchangeably used refer to a carrier or a diluent that does not cause significant irritation to a subject or organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in Remington's Pharmaceutical Sciences, Mack Publishing Co., Easton, Pa., latest edition, which is incorporated herein by reference.

Any suitable route of administration can be used for the disclosed compositions. Routes of administration can, for example, include topical, enteral, local, systemic, or parenteral. For example, administration can be intratumoral, peritumoral, epicutaneous, inhalational, enema, conjunctival, eye drops, ear drops, alveolar, nasal, intranasal, vaginal, intravaginal, transvaginal, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc.

For homing to cells and tissue, particularly suitable routes of administration include parenteral, either local or systemic. For example, particularly suitable routes of administration for homing to cells and tissues include intravenous, injection, infusion, intraarterial, intramuscular, intratumoral, peritumoral, intracerebral, intraventricular, intracerebroventricular, intracardiac, subcutaneous, intraosseous, intradermal, intrathecal, intraperitoneal, intravesical, intramedullar, intraocular, intracranial, intracisternal, epidural, peridural, and intravitreal. The disclosed compositions can be used in and with any other procedure. For example, the disclosed compositions can be administered as part of HIPEC therapy. In HIPEC a heated sterile solution containing a composition of interest is continuously circulated throughout the peritoneal cavity.

Pharmaceutical compositions can be manufactured by processes well known in the art, e.g., by means of conventional mixing, dissolving, granulating, dragee-making, levigating, emulsifying, encapsulating, entrapping or lyophilizing processes.

Pharmaceutical compositions for use in the disclosed methods thus can be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients can be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

The preparations described herein can be formulated for parenteral administration, e.g., by bolus injection or continuous infusion. Formulations for injection can be presented in unit dosage form, e.g., in ampoules or in multidose containers with optionally, an added preservative. The compositions can be suspensions, solutions or emulsions in oily or aqueous vehicles, and can contain formulatory agents such as suspending, stabilizing and/or dispersing agents.

Pharmaceutical compositions for parenteral administration include aqueous solutions of the active preparation in water-soluble form. Additionally, suspensions of the active ingredients can be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions can contain substances, which increase the viscosity of the suspension, such as sodium carboxymethyl cellulose, sorbitol or dextran. Optionally, the suspension can also contain suitable stabilizers or agents which increase the solubility of the active ingredients to allow for the preparation of highly concentrated solutions.

Alternatively, the active ingredient can be in powder form for constitution with a suitable vehicle, e.g., sterile, pyrogen-free water based solution, before use.

The disclosed compositions can be provided in any suitable formulation. For example, solid, liquid, solution, gel, slow release, timed release, etc.

Pharmaceutical compositions for use in the disclosed methods include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the disclosed methods, the therapeutically effective amount or dose can be estimated initially from in vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl et al in The Pharmacological Basis of Therapeutics, Ch. 1 p. 1. (1975)).

Dosage amount and interval can be adjusted individually to provide plasma of antibodies which are sufficient to prevent or reduce viral entry (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma levels, target site measurements, or other suitable measure above the MEC for 10-90% of the time, preferable between 30-90% and most preferably 50-90%.

Depending on the severity and responsiveness of the condition to be treated, dosing can be of a single or a plurality of administrations, with course of treatment lasting from several days to several weeks or until cure is effected, diminution of the disease state is achieved, or other therapeutic effect is achieved.

The amount of a composition to be administered will, of course, be dependent on the subject being treated, the severity of the affliction, the manner of administration, the judgment of the prescribing physician, etc.

The co-composition or cargo composition can be a microparticle or a nanoparticle, such as a nanosphere, nanoshell, nanoworm, heat generating nanoshell, and the like. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with, for example, a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

Fatty acids (i.e., lipids) that can be conjugated to the disclosed tLyP-1 compositions and co-compositions and cargo compositions include those that allow the efficient incorporation of the peptide into liposomes. Generally, the fatty acid is a polar lipid. Thus, the fatty acid can be a phospholipid. The provided compositions can comprise either natural or synthetic phospholipid. The phospholipids can be selected from phospholipids containing saturated or unsaturated mono or disubstituted fatty acids and combinations thereof. These phospholipids can be, for example, dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Alabaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

The other molecules, elements, moieties, etc. can be covalently linked to or non-covalently associated with, for example, the disclosed co-compositions, cargo compositions, tLyP-1 composition, protein, peptide, or amino acid sequence. Such molecules, elements, moieties, etc. can be linked, for example, to the amino terminal end of the disclosed protein, peptide, amino acid sequence, or tLyP-1 peptide; to an internal amino acid of the disclosed protein, peptide, amino acid sequence, or tLyP-1 peptide; to the carboxy terminal end of the disclosed protein, peptide, or amino acid sequence; to the protein, peptide, amino acid sequence on the N terminal side of the tLyP-1 peptide; via a linker to the disclosed protein, peptide, amino acid sequence, or tLyP-1 peptide; or a combination. The disclosed tLyP-1 compositions can further comprise a linker connecting such molecules, elements, moieties, etc. and disclosed tLyP-1 composition, protein, peptide, amino acid sequence, or tLyP-1 peptide. The disclosed tLyP-1 composition, protein, peptide, amino acid sequence, or tLyP-1 peptide can also be conjugated to a coating molecule such as bovine serum albumin (BSA; see Tkachenko et al., (2003) J Am Chem Soc, 125, 4700-4701) that can be used to coat nanoparticles, nanoworms, nanoshells, and the like with the protein, peptide, amino acid sequence, or tLyP-1 peptide.

Protein crosslinkers that can be used to crosslink other molecules, elements, moieties, etc. to the disclosed co-compositions, cargo compositions, tLyP-1 compositions, proteins, peptides, amino acid sequences, etc. are known in the art and are defined based on utility and structure and include DSS (Disuccinimidylsuberate), DSP (Dithiobis(succinimidylpropionate)), DTSSP (3,3'-Dithiobis(sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-p-hydroxybenzimidate hydrochloride, 98%), DMA (Dimethyladipimidate hydrochloride).

Components of co-compositions or cargo composition can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide] (Avanti Polar Lipids) by making use of a free cysteine sulfhydryl group on the component. The reaction can be performed, for example, in aqueous solution at room temperature for 4 hours. This coupling chemistry can be used to couple components of co-compositions and cargo compositions.

The disclosed compounds, components, and compositions can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., 2001). The particles can have surface modifications, for example, for reticuloendothelial system avoidance (PEG) and homing (homing molecules), endosome escape (pH-sensitive peptide; for example, Pirello et al., 2007), a detectable agent, a therapeutic compound, or a combination. To accommodate all these functions on one particle, optimization studies can be conducted to determine what proportion of the available linking sites at the surface of the particles any one of these elements should occupy to give the best combination of targeting and payload delivery. The cell internalization and/or tissue penetration of such co-compositions and cargo compositions can be mediated by the disclosed tLyP-1 peptides, amino acid sequences, proteins, molecules, conjugates, and compositions.

The tLyP-1 peptides, amino acid sequences, proteins, molecules, conjugates, and compositions themselves can be coupled to other components as disclosed herein using any known technique or the techniques described herein (although generally not, as described elsewhere herein, to the disclosed co-compositions). A maleimide function can also be used as a coupling group. These chemistries can be used to couple tLyP-1 peptides, amino acid sequences, proteins, molecules, conjugates, and compositions to each other and to other components.

tLyP-1 peptides, amino acid sequences, and proteins can also be coupled to other components using, for example, maleimide coupling. By way of illustration, tLyP-1 peptides, amino acid sequences, and proteins can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide] (Avanti Polar Lipids) by making use of a free cysteine sulfhydryl group on the tLyP-1 peptides, amino acid sequence, or protein. The reaction can be performed, for example, in aqueous solution at room temperature for 4 hours. This coupling chemistry can be used to couple the disclosed tLyP-1 peptides, amino acid sequences, and proteins to many other components, molecules and compositions.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. In particular, pets and livestock can be a subject. The subject can be an invertebrate, such as a worm or an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In the context of endometriosis and endometriosis cells, it is understood that a subject is a subject that has or can have endometriosis and/or endometriosis cells.

Tumor-penetrating tLyP-1 peptides can be used to augment tumor imaging and tumor treatment with anti-cancer drugs. The effect of tLyP-1 peptides on imaging can be tested. For example, optical imaging with, for example, near infrared fluorphores using a Kodak IN VIVO Fx imager and Li-Cor Odyssey imager (e.g. Simberg et al., 2007; Sugahara et al., 2009), and MRI imaging can be used. For MRI imaging, the co-composition or cargo composition can be an MRI contrast agent such as Feridex iron oxide nanoparticles and gadolinium compounds. These compounds can be injected into tumor-bearing mice, for example, with and without a tumor-homing tLyP-1 peptide or a combination of peptides, followed by imaging. The results can be use to determine effectiveness of treatments and to assess different treatment protocols for using tLyP-1 peptides with therapeutics as the co-composition or cargo composition.

Combinations of different tLyP-1 peptides and different co-compositions and/or cargo compositions can be tested for optimal accumulation and distribution of the co-composition or cargo composition in the target cells and tissue by, for example, varying the dose of the drug and using the dose of the peptide that gives the maximal effect. The disclosed results show that tLyP-1-drug combinations can reduce the amount of drug needed and therefore, the side effects, while producing the same anti-tumor effect. tLyP-1 peptides can also produce effects not achievable by using the co-composition or cargo composition alone. For example, use of tLyP-1 peptides can allow higher concentrations of the co-composition or cargo composition in cells and tissues that is otherwise possible. In such cases, the effectiveness of the co-composition or cargo composition can be beyond that obtainable with conventional therapy.

As defined herein, a C-terminal element (CendR element) refers to either an arginine, a lysine, or a lysine-glycine (for a type 1 CendR element), or a histidine or an amino acid sequence having the sequence $X_1X_2X_3X_4$, where $X_1$ can be R, K or H, where $X_4$ can be R, K, H, or KG, and where $X_2$ and $X_3$ can each be, independently, any amino acid (for a type 2 CendR element).

Type 1 CendR elements are a C-terminal arginine, a C-terminal lysine, or a C-terminal lysine-glycine pair, where glycine is at the furthest C-terminal position. In other words, in the case where a lysine is on the C terminus end, the CendR element can remain functional with a glycine on the C terminus side of the lysine. However, it is not necessary to have glycine on the end in order for the lysine residue to be functional as a C-terminal element, so that lysine can be present without glycine and still be functional. The converse is not true, however, in that glycine cannot function as a C-terminal element without the presence of lysine adjacent to it. Arginine does not require either lysine or glycine to function as a C-terminal element, as long as it remains in the furthest C-terminal position.

Type 2 CendR elements are C-terminal histidine and amino acid sequences having the sequence $X_1X_2X_3X_4$, where $X_1$ can be R, K or H, where $X_4$ can be R, K, H, or KG, and where $X_2$ and $X_3$ can each be, independently, any amino acid. Such CendR elements can be referred to as type 2 CendR elements. The $X_2$ and $X_3$ amino acids can be selected for specific purposes. For example, $X_2$, $X_3$, or both can be chosen to form all or a portion of a protease recognition sequence. This would be useful, for example, to specify or enable cleavage of a peptide having the CendR element as a latent or cryptic CendR element that is activated by cleavage following the $X_4$ amino acid. Examples of such amino acid choices are shown in Tables 1 and 2. The $X_1$, $X_2$ and $X_3$ amino acids can also be selected, for example, to recruit additional proteins to NRP-1 molecules at the cell surface. This can be applied, for example, to modulate the selectivity and internalization and/or tissue penetration potency of CendR elements (and the compositions, conjugates, proteins, and peptides containing CendR elements). The $X_2$ and $X_3$ amino acids can also be selected to prevent protease cleavage within the $X_1$-$X_4$ motif. For example, $X_2$ and/or $X_3$ can be proline, which reduces or eliminates protease cleavage, such as by carboxypeptidase, between the proline and the next downstream amino acid. As another example, one or more of the bonds between $X_1$, $X_2$, $X_3$, and/or $X_4$ can be modified to reduce or eliminate protease cleavage at those bonds. Optionally, certain amino acids can also be excluded from use for $X_2$, $X_3$, or both. For example, if desired, G and D can be excluded from simultaneous use as $X_2$ and $X_3$, respectively. Some type 2 CendR elements can also be described as R/K/HXXR/K/H, R/KXXR/K, and R/K/HXXKG.

For the sake of convenience, amino acid motifs that would constitute a CendR element if an arginine, lysine, lysine-glycine pair, or histidine were at the C-terminus and where the exposure in the future of the arginine, lysine, lysine-glycine pair, or histidine at the C-terminus is planned or intended, can be referred to as CendR elements or latent CendR elements.

CendR elements are described in U.S. Patent Application Publication Nos. 20090226372, 20090226372, 20090246133, and 20100322862. U.S. Patent Application Publication Nos. 20090226372, 20090226372, 20090246133, and 20100322862 are hereby incorporated herein by reference in their entirety, and specifically for their description of CendR elements.

EXAMPLE

The following example is put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: A Truncated Form of LyP-1 is Internalized into Cells Through the CendR Internalization Pathway This example describes the properties of a truncated form of LyP-1, in which CendR motif is exposed (CGNKRTR; tLyP-1; SEQ ID NO:4), and inhibition of the CendR receptor, neuropilin-1 to show that LyP-1 and tLyP-1 internalized into cells through the CendR internalization pathway.

A. Materials and Methods

1. Antibodies and Purified Proteins

The following purified proteins were used for phage binding assays: recombinant human NRP1 (R&D) and recombinant human NRP2 Fc chimera (R&D). The ligand-blocking polyclonal antibodies, goat anti-rat NRP1 and goat anti-human NRP2, were purchased from R&D. Goat IgG (AbCam) was used as control. For immunofluorescence, the primary antibodies were: (1) monoclonal rat anti-mouse CD31 (BD Biosciences) (2) polyclonal rabbit anti-human NRP1 (Chemicon) (3) polyclonal rabbit anti-human NRP2 (Novus Biologicals) and (4) polyclonal rabbit anti-T7 phage (Teesalu et al, 2009). The following secondary antibodies were used for detection: donkey anti-goat 488/546, goat anti-rat 546 and goat anti-rabbit 488/546 (Invitrogen).

2. Cell Lines and Tumors

MDA-MB-435, DU145 and PPC1 cells were cultured in DMEM (Gibco), and 4T1 cells in IMDM (Gibco). Media were supplemented with 10% fetal bovine serum (FBS) and 1% penicillin-streptomycin (Gibco). Cells were maintained at 37° C./5% $CO_2$.

To produce 4T1 tumors, BALB/c mice were orthotopically injected into the mammary fat pad with $10^6$ cells suspended in 100 μL of PBS. To produce MDA-MB-435 breast tumors, BALB/C athymic nude mice were orthotopically injected into the mammary fat pad with $2 \times 10^6$ cells suspended in 100 μL of PBS.

Before any surgical procedure, mice were anesthetized with i.p. injections of xylazine (10 mg/kg) and ketamine (50 mg/kg). Animal experimentation was performed according to procedures approved by the Animal Research Committees at the University of California, Santa Barbara.

3. Peptides and Peptide-Conjugated Nanoworms

The peptides were synthesized on a microwave-assisted automated peptide synthesizer (Liberty; CEM, Matthews, N.C.) following Fmoc/t-Bu strategy on rink amide resin with HBTU activator, collidine activator base and 5% piperazine for deprotection. Fluorescein and biotin tags were incorporated during the synthesis at the N-terminus of the sequence. Cleavage using a 95% TFA followed by purification gave peptides with >90% purity.

Tetrameric peptides were obtained by conjugation with neutravidin (NA, Pierce). NA was dissolved at 5 mg/mL in Millipore water with 5% glycerol, heated to 37° C. for 1 h, sonicated and filtered. Biotinylated peptide stocks were prepared in water shortly before use, sonicated, and added at equal volume to the NA for a final concentration of 250 μM peptide and 40 μM NA. Conjugates were used after 30 min with no additional purification.

Nanoworms coated with peptides were prepared as previously described (Agemy et al, 2010; Park et al, 2009). Amine groups on the nanoworms were pegylated with maleimide-5KPEG-NHS (JenkemTechnology, China). Peptides were conjugated to the nanoparticles through a thioether bond between the cysteine thiol from the peptide sequence and the maleimide on the functionalized particles through a Michael addition reaction.

4. In Vitro Phage Binding and Internalization

Microtiter wells (Costar) were coated with 5 μg/mL of purified NRP1 or NRP2, blocked with PBS supplemented with 0.5% BSA and incubated with $10^8$ plaque-forming units (pfu) of phage in 100 μL of PBS/0.05% Tween 20 for 20 h at 37° C. After six washes in PBS/0.05% Tween 20, bound phage was eluted with 200 μL of 1 M Tris-HCl (pH 7.5)/0.5% SDS for 30 min and quantified by a plaque assay (titration).

To measure phage binding on cells, $2 \times 10^5$ suspended cells were incubated with $7 \times 10^8$ pfu/mL of T7 phage in DMEM/BSA 1% for 1 h at 4° C. Ligand-blocking antibodies or control goat IgG isotype (10 μg/sample) were added 30 min prior to phage incubation. The cells were washed four times with DMEM/BSA 1%, and lysed with lysogeny broth containing 1% Nonidet P-40 (LB/NP40) before phage titration.

5. Phage, Nanoworm, and Peptide Homing In Vivo.

Normal BALB/c mice were intravenously injected with $10^{10}$ pfu of phage, which were allowed to circulate for 15 min. The mice were then perfused through the heart with PBS containing 1% BSA and tissues were collected and homogenized in 1 mL of LB/NP40 for titration.

4T1 tumor bearing BALB/c mice and MDA-MB-435 tumor bearing nude mice were intravenously injected with respectively 150 μL and 100 μL of 1 mM FAM-labeled synthetic peptides. After 1 h circulation, mice were perfused and tissues were collected and observed under UV light (Illuma—tool Bright Light System LT-9900) and processed for immunofluorescence analysis.

Peptide-nanoworms (5 mg iron/kg mouse) were intravenously injected in 4T1 tumor-bearing mice and allowed to circulate for 30 min to 16 h. After perfusion, organs were harvested and processed for immunofluorescence analysis.

6. Immunofluorescence

Tissues were fixed with 4% paraformaldehyde (PFA) and cryoprotected in 30% sucrose before OCT (Sakura) embedding and freezing. Tissues were sectioned at 7 μm and stained with primary antibodies at 4° C. overnight. Secondary antibodies were incubated for 1 h at 37° C. Stained tissue sections were mounted in Vectorshield DAPI-containing mounting media (Vector Laboratories) and examined on a Fluoview 500 confocal microscope (Olympus America). To quantify the homing area of peptide-nanoworms, 10 fields/tumor cryosections were analyzed with Image J.

Cells were grown on collagen I-coated coverslips (BD Biosciences) for 24-72 h. After 4% PFA fixation, cells were stained with antibodies following the same procedure as for tumor sections, and mounted in DAPI-containing mounting media. For phage binding assay, $10^9$ pfu of phage in cell culture medium were incubated for 1-2 h. When neutravidin-peptide inhibitors were used, they were added to the cell medium 30 min prior to phage incubation. Neutravidin alone, at the maximum concentration used in the assay, was used as a control. Cells were examined on a Fluoview 500 confocal microscope (Olympus America).

7. Statistical Analysis

Data were analyzed by two-tailed Student's t test.

B. Results

1. LyP-1 is a Cryptic CendR Peptide

Figure 6:
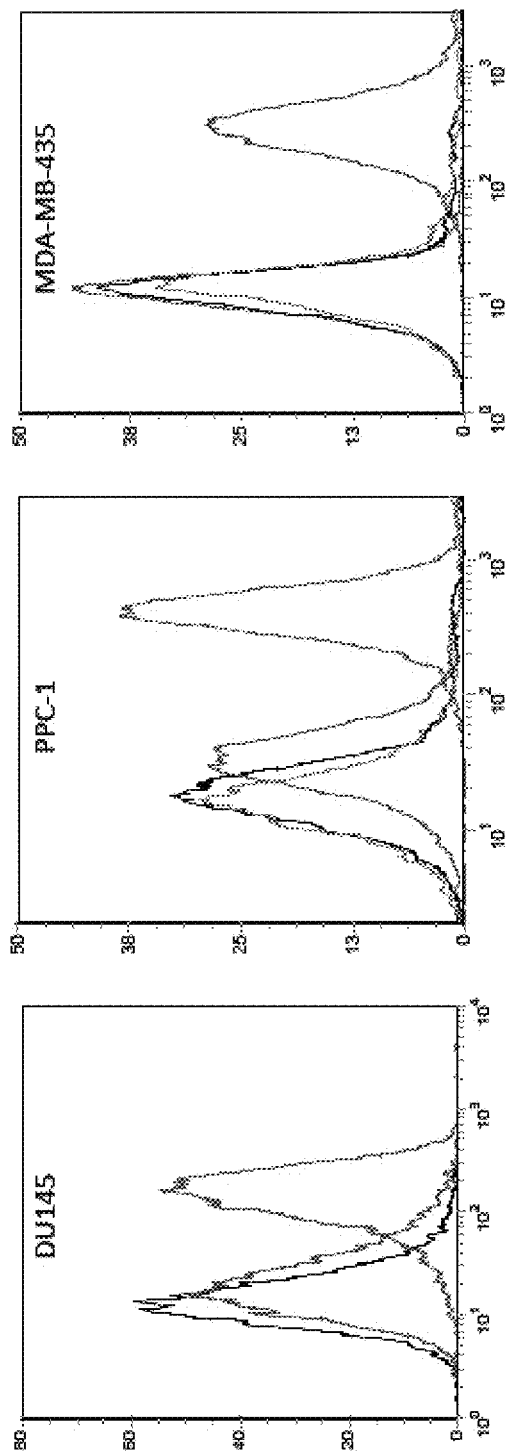
FIG. 6 shows Neuropilin expression in cancer cell lines. Fluorescence-activated cell sorting (FACS) analysis was done on live human tumor cells to detect cell-surface expression of NRP1 and NRP2. Approximately $10^6$ cells were stained with mouse anti-NRP1 (monoclonal, Miltenyi), mouse anti-NRP2 (monoclonal, R&D), or mouse IgG (BD PharMingen) at 4° C. DU145 prostate carcinoma cells expressed exclusively NRP1 (line that peaks about 200), whereas MDA-MB-435 breast tumor cells expressed only NRP2 (line that peaks about 300). PPC1 prostate tumor cells, while expressing very high levels of NRP1 (line that peaks about 500), also expressed low levels of NRP2 (line that peaks between 30-40). Representative of 3 experiments.

The role of the CendR motif in the LyP-1 peptide was investigated by testing the binding of phage displaying the predicted active CendR fragment CGNKRTR (tLyP-1 for truncated LyP-1; SEQ ID NO:4) and other truncated forms of LyP-1 to cultured tumor cells. DU145 prostate carcinoma cells were used, which express NRP1, but not NRP2 (FIG. 6). As these peptides could have other receptors on the DU145 cells, inhibition of cell binding by a function-blocking anti-NRP1 antibody was used as an indicator of NRP1 dependence of phage binding. The antibody inhibited the cell binding of the tLyP-1 phage by about 70% (FIG. 1A). A similar degree of inhibition was obtained for the phage expressing the prototypic CendR peptide, RPARPAR (SEQ ID NO:9). The NRP1 antibody did not significantly inhibit the low binding of the other truncated forms of LyP-1 (FIG. 1B). Thus, a single or double basic residue at the C-terminus, as in CGNK (amino acids 1-4 of SEQ ID:10) or CGNKR (amino acids 1-5 of SEQ ID NO:10), was not enough to confer significant ability to bind to NRP1. CGNKRTRG (amino acids 1-8 of SEQ ID NO:10) showed a mild reproducible decrease in DU145 cell binding upon anti-NRP1 treatment, indicating that the presence of the glycine residue C-terminal of the CendR motif is compatible with NRP1 binding. This is supported by recent modeling studies showing that glycine-containing peptides ($G_7$ (SEQ ID NO:104), $G_3RG_3$ (SEQ ID NO:105), and $G_4RG_2$ SEQ ID NO:106) were able to dock in NRP1 binding pocket without major deformation of the receptor structure (Haspel et al, 2011). In contrast, the binding of full-length LyP-1 to the cells was not inhibited by the anti-NRP1, suggesting that the peptide has to be processed into its CendR form to be able to bind to NRP1.

Figure 1C:
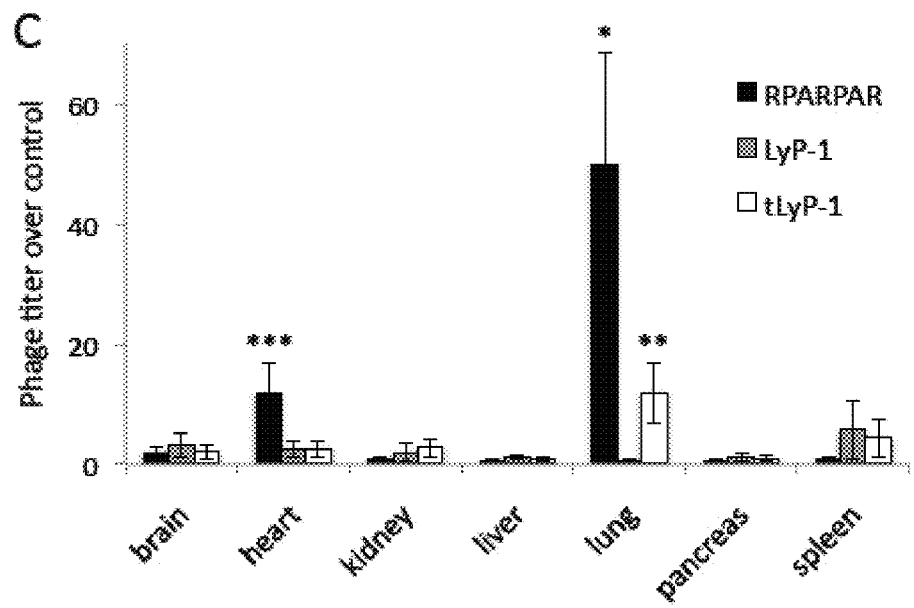

The distribution of intravenously administered tLyP-1 phage in normal mice after 15 minutes circulation was analyzed, and observed that it showed some accumulation in the lungs (FIG. 1C). This finding agrees with previously described accumulation of CendR phage in the lungs, presumably because it is the first vascular bed encountered by intravenously injected substances (Teesalu et al, 2009). Taken together, the binding and inhibition results, and the in vivo phage distribution strongly suggest that tLyP-1 is an active CendR peptide.

2. NRP1 Binds tLyP-1 Phage and Mediates Internalization of the Phage

Figure 2:
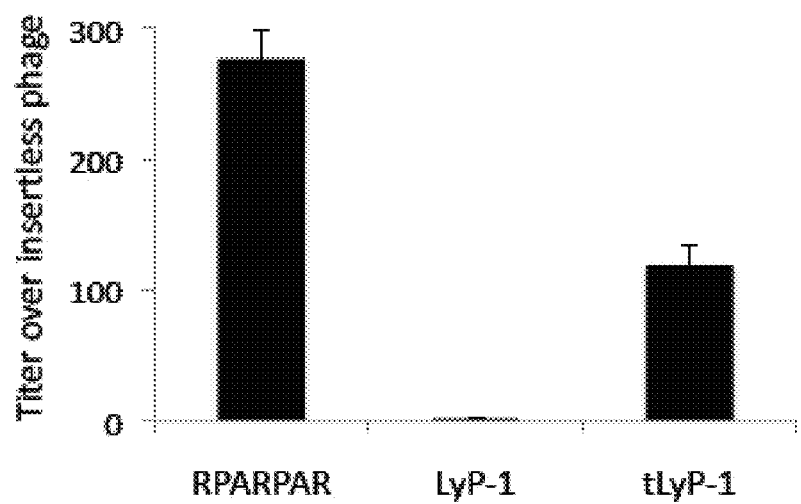
FIG. 2 shows NRP1 binds tLyP-1 and mediates its internalization. Purified NRP1 was coated on microtiter wells and the binding of insertless, RPARPAR (SEQ ID NO:9), LyP-1 and tLyP-1 phage was tested. Binding is expressed as fold over control phage (RPARPAR/insertless=276, LyP-1/insertless=1.6, tLyP-1/insertless=119±SEM, n=3/group).

The binding of tLyP-1 to purified NRP1 was then tested. The tLyP-1 phage bound to immobilized NRP1 about 120 times more than insertless control phage, whereas phage expressing intact LyP-1 showed no binding (FIG. 2). RPARPAR phage exhibited a 280-fold binding ratio over the control phage, presumably because its affinity for NRP-1 is higher than that of tLyP-1. The tLyP-1 and RPARPAR phage, but not LyP-1 phage, bound to and were internalized into cultured PPC1 cells, which express high levels of NRP1 (FIG. 6). Inside these cells, tLyP-1 co-localized with NRP1 in vesicular structures, suggesting that the two proteins were co-internalized upon interaction. tLyP-1 internalization into the PPC1 cells was inhibited in a dose-dependent manner by oligomeric RPARPAR peptide, further showing that tLyP-1 internalization follows the CendR pathway.

Confocal microscope images were made of PPC1 cells incubated in the presence of $10^9$ pfu of insertless, RPARPAR (SEQ ID NO:9), LyP-1 or tLyP-1 phage. Phage were detected by staining with anti-T7 phage polyclonal antibody. Nuclei were stained with DAPI. Confocal microscope image was made of PPC1 cells incubated with tLyP-1 phage. Cells were co-stained for NRP1 and nuclei were stained with DAPI. Co-localization between tLyP-1 phage and NRP1 was observed. After 30 min pre-incubation with increasing concentrations of neutravidin-RPARPAR peptide (SEQ ID NO:9), PPC1 cells were incubated with tLyP-1 phage for 2 h. Non-conjugated neutravidin was used as a control. Nuclei were stained with DAPI. Cells were analyzed by confocal microscopy.

3. NRP2 Binds CendR Peptides and Mediates their Internalization

Figures 3A, 3B:
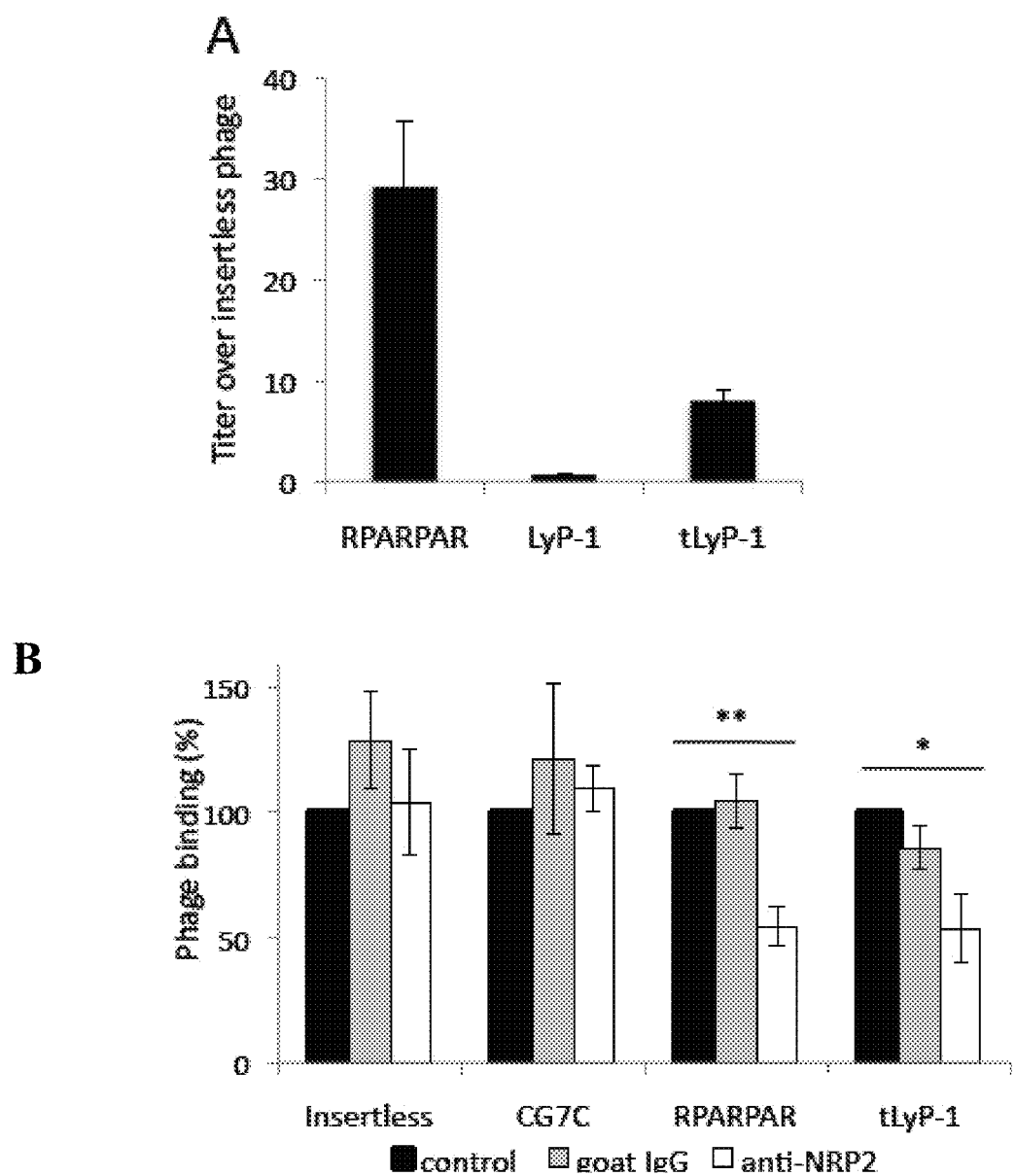
FIGS. 3A and 3B show NRP2 binds tLyP-1 and mediates its internalization. A. Purified NRP2 was coated on microtiter wells and the binding of insertless, RPARPAR (SEQ ID NO:9), LyP-1 and tLyP-1 phage was tested. Binding is expressed as fold over control phage (RPARPAR/insertless=29, LyP-1/insertless=0.6, tLyP-1/insertless=8±SEM, n=3/group). B. MDA-MB-435 cells were incubated with phage at 4° C. to assess NRP2 binding. Ligand-blocking anti-NRP2 inhibited binding of both CGNKRTR (SEQ ID NO:4) and RPARPAR phage (SEQ ID NO:9), whereas goat IgG had no effect. Insertless and CG7C control phage binding was not inhibited. Binding is expressed as percentage of binding in control conditions. (mean±SEM; n=4/group; * p<0.05; **, p<0.01).

NRP2 involvement in the CendR pathway has not been addressed. Given the similarities in tissue and cell distribution of LyP-1 and NRP2, and the homology between NRP1 and NRP2, it was realized that NRP2 could be a CendR receptor.

tLyP-1 phage bound to purified NRP2 about 8 times more than insertless phage (FIG. 3A). As observed for NRP1 binding, RPARPAR phage exhibited higher level of binding to NRP2 than tLyP-1 (binding ratio over control: 29). Binding of both peptides was higher to NRP1 than to NRP2, suggesting that CendR peptides preferentially bind to NRP1. LyP-1 phage did not bind to NRP2 (binding ratio over control: 0.6). tLyP-1 phage also bound and internalized into cultured MDA-MB-435 cells, which express NRP2 but not NRP1 (FIG. 6). It co-localized with NRP2 inside the cells. A confocal microscope image was made of MDA-MB-435 cells cultured for 2 h in presence of tLyP-1 phage. Cells were co-stained for NRP2 and nuclei were stained with DAPI. Co-localization between tLyP-1 phage and NRP2 was observed. tLyP-1 phage internalization into MDA-MB-435 cells was lower than into PPC1 cells, possibly due to the weaker affinity of for NRP2 than for NRP1, or/and to lower total NRP expression in the MDA-MB-435 cells. Using a function-blocking antibody against NRP2, it was confirmed that tLyP-1 phage directly bound to NRP2 in MDA-MB-435 cells (FIG. 3B). The anti-NRP2 antibody also inhibited RPARPAR phage binding, and oligomeric RPARPAR peptide blocked the binding and internalization of phage tLyP-1 in the cells, further demonstrating the role of NRP2 in the CendR pathway. After 30 min pre-incubation with increasing concentrations of neutravidin-RPARPAR peptide, MDA-MB-435 cells were incubated with tLyP-1 phage for 2 h. Non-conjugated neutravidin was used as a control. Nuclei were stained with DAPI.

4. LyP-1 Internalization Uses the CendR Pathway

Having established that tLyP-1, but not LyP-1, binds to NRP1 and NRP2, but both peptides internalize into tumor cells, it was realized that LyP-1 is converted into tLyP-1 and that the two peptides are taken up by cells through the CendR pathway. The effect of an excess of tLyP-1 on LyP-1 internalization was tested. Oligomeric tLyP-1 peptide dose-dependently and fully inhibited LyP-1 phage internalization, consistent with a common internalization pathway and the cleavage of LyP-1 into tLyP-1. After 30 min pre-incubation with increasing concentrations of neutravidin-tLyP-1 peptide, MDA-MB-435 cells were incubated with LyP-1 phage for 2 h. Phage were stained with anti-T7 antibody. Nuclei were stained with DAPI.

Figure 7:
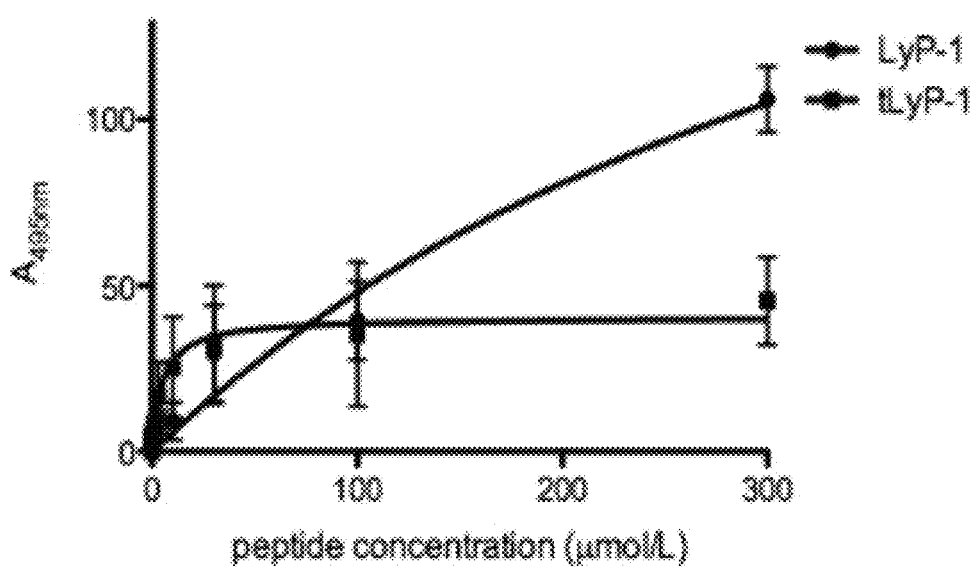
FIG. 7 shows tLyP-1 binding to LyP-1 receptor p32. Binding of FAM-tLyP-1 and FAM-LyP-1 to p32 was measured by an ELISA-based assay. Microtiter wells coated with 3 µg/mL of purified p32 (Fogal et al, 2008) were incubated with increasing concentrations of FAM-peptides at 37° C. for 1 h. After washing with cold PBS added with 0.01% Tween 20 and 0.2 M NaCl, fluorescence was read at 495 nm. Note that p32 bound weakly to p32 compared to LyP-1.

The MDA-MB-435 cells express the cell surface LyP-1 primary receptor p32 (Fogal et al, 2008). To test whether internalization of tLyP-1 and LyP-1 could occur through this receptor, tLyP-1 capacity to bind p32 was explored. A saturation assay performed with fluorescein-labeled peptides (FAM-peptides) and purified p32, showed low binding of tLyP-1 to p32, whereas robust binding was seen with FAM-LyP-1 (FIG. 7). Moreover, affinity chromatography of 4T1 breast tumor extracts on tLyP-1 revealed no binding of p32 to the tLyP-1 affinity matrix (data not shown). Thus, only the intact LyP-1 peptide binds to p32.

Figure 4:
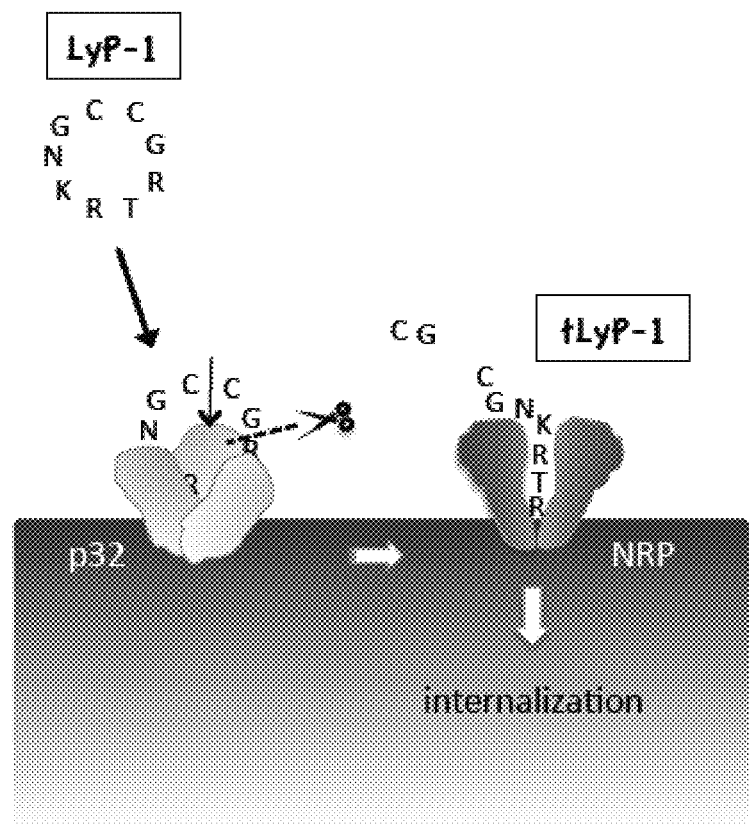
FIG. 4 shows LyP-1 is a cryptic CendR peptide. Cyclic LyP-1 (SEQ ID NO:10) concentrates at the surface of tumor cells by binding to its primary receptor p32. LyP-1 is then proteolytically cleaved into the linear truncated form, tLyP-1 (SEQ ID NO:4), which diminishes its affinity for p32. The exposed C-terminal CendR motif becomes active and triggers binding to NRP1 and/or NRP2, and subsequent cell internalization.

The existence of a common internalization pathway for LyP-1 and tLyP-1, and the lack of tLyP-1 binding to p32 support the idea that LyP-1 follows a CendR pathway in the same manner documented for the iRGD peptide (Sugahara et al., 2009): LyP-1 first binds to cell surface p32 in tumors, which triggers a protease cleavage into the tLyP-1 form and a shift from p32 to NRP1/2, made possible by the loss of affinity for p32 and newly acquired affinity for the NRPs. The NRP binding then activates the Cend cell internalization pathway (FIG. 4).

5. tLyP-1 Specifically Homes to 4T1 Tumors

Given the high NRP expression in the majority of tumors (Ellis et al, 2006; Guttmann-Raviv et al, 2006, Bagri et al, 2009), tissue distribution of intravenously injected tLyP-1 in mice bearing orthotopic 4T1 breast cancers was studied. This tumor was selected because the 4T1 cells over-express both NRP1 and NRP2. Confocal microscope images were made of mouse 4T1 tumor cells stained with anti-NRP1 (polyclonal, Chemicon) and anti-NRP2 (polyclonal, Invitrogen) antibodies. 4T1 cells express both NRPs. Tumors examined 1 hour after the injection of FAM-tLyP-1 were strongly fluorescent under UV light. Normal tissues were negative, with the exception of the kidneys, which reflects the clearance of the peptide through this organ. A control peptide, FAM-ARALPSQRSR (Laakkonen et al, 2002), did not accumulate in the tumors. Similar results were obtained in another tumor model, human MDA-MB-435 breast cancer xenografts. Confocal microscopy confirmed the selective accumulation of FAM-tLyP-1 in 4T1 tumor tissue, and revealed extensive spreading of the label within the tumor.

150 µl of 1 mM FAM-tLyP-1 or control FAM-ARALP-SQRSR was intravenously injected into 4T1 tumor bearing mice. The peptides were allowed to circulate for 1 h and tumors and organs were collected and viewed under UV light. Strong fluorescence in the tumor from the FAM-tLyP-1 injected mouse was observed compared to the other organs, and the absence of fluorescence in the control panel. FAM-tLyP-1 (100 µl of 1 mM) was intravenously injected into MDA-MB-435 tumor bearing mice. The peptide was allowed to circulate for 45 min, and tumor and organs were collected and viewed under UV light. Fluorescence was only found in the tumor. Confocal microscope images were made of the tumor and of normal organs after 1 h of FAM-tLyP-1 circulation in 4T1 tumor bearing mice.

To evaluate the capacity of tLyP-1 to deliver nanoparticles into the tumors and to penetrate the tumor tissue, FAM-tLyP-1 was conjugated to iron oxide nanoworms (tLyP-1-NWs; dimensions: 30×80-100 nm) (Park et al, 2009; Agemy et al, 2010). Examination of tLyP-1-NW biodistribution showed specific homing of tLyP-1-NWs to the tumors. As reported previously for iron oxide nanoparticles, the NWs non-specifically accumulated in the liver and spleen to a small extent (Thorek et al, 2006), and some were also found in the kidney, presumably reflecting the release of the labeled peptide from the NWs. The accumulation of the NWs in the tumor was observed at all time points studied (from 30 min to overnight circulation). The tLyP-1-NWs also specifically homed to the tumors in a third breast cancer model, human MDA-MB-231 breast cancer xenografts.

NWs conjugated to FAM-LyP-1 and FAM-tLyP-1 peptides were intravenously injected into 4T1 tumor bearing mice (5 mg iron/kg mouse) and allowed to circulate for 4 h. Fluorescence was absent in the lungs. NWs (5 mg iron/kg mouse) conjugated to FAM-tLyP-1 peptide were intravenously injected into 4T1 tumor bearing mice and allowed to circulate for 30 min, 6 h or 16 h. The NWs were still localized and spread in the tumor after extended circulation, whereas their presence decreased over time in other organs involved in non-specific uptake. To produce MDA-MB-231 breast tumors, BALB/C athymic nude mice were orthotopically injected into the mammary fat pad with $5 \times 10^6$ cells suspended in 100 µL of PBS/matrigel (BD Biosciences) (50/50). tLyP-1-NWs (5 mg iron/kg mouse) were intravenously injected into tumor bearing mice. Tumors and organs were collected and processed for immunofluorescence. The NWs were allowed to circulate for 4 h. Strong fluorescence was observed in the tumor compared to the other organs.

6. Comparison of tLyP-1-NWs with LyP-1-NWs and RPARPAR-NWs

The tissue distribution profile of tLyP-1-NW was comparable to that of the parental LyP-1-NW with respect to tumor-specific homing, but their spreading patterns were different. After 4 hours of circulation, tLyP-1-NWs showed a significantly wider distribution in the tumor tissue than LyP-1-NWs; the fluorescent surface in the tumor was with about 4 times larger in the tLyP-1 tumors. Confocal microscope images were made of tLyP-1-NW in comparison with blood vessels and NRPs. Blood vessels were stained with anti-CD31 antibody. Co-localization between the NWs and the blood vessels was observed. The label in the tumor tissue spread over time. After 4 hours of circulation, tLyP-1-NW were co-localized with the NRP.

Figure 5:
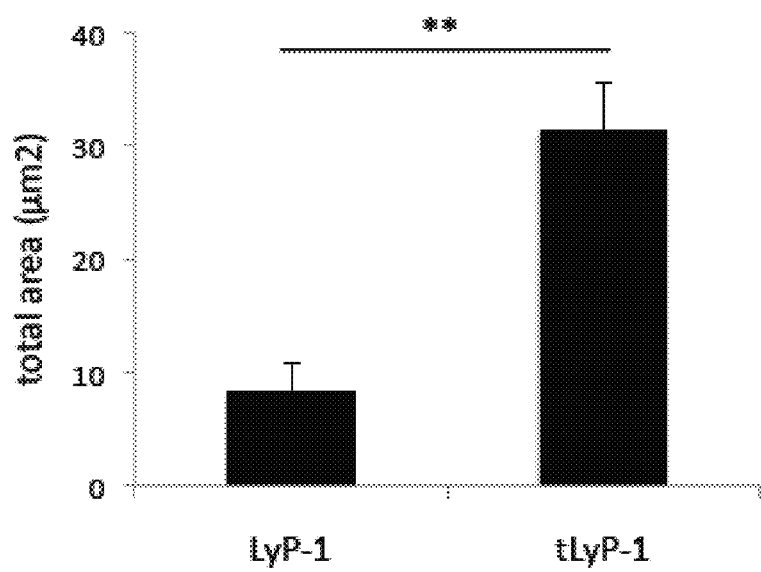
FIG. 5 shows comparison of tLyP-1-NW homing with LyP-1-NW and RPARPAR-NW homing (SEQ ID NO:9). Fluorescence of 10 fields/tumor was quantified with Image J. (mean±SEM; n=3/group; **, p<0.01).

The enhanced penetration properties of tLyP-1-NW are attributable to the exposed CendR motif. The distribution of the tLyP-1-NWs was strikingly different from NWs coated with the prototypic CendR, RPARPAR. Besides extensive tumor accumulation, RPARPAR-NWs were also present in each of the other tissues examined (FIG. 5). The accumulation of the RPARPAR-NWs in the liver, spleen and kidney was higher than that of tLyP-1-NWs or LyP-1-NWs. In addition, the RPARPAR-NWs were present in the heart, lungs and pancreas, which were negative for tLyP-1-NWs. Thus, tLyP-1, even though it is an active CendR peptide, is a specific tumor homing peptide, possibly because of its lower affinity for NRP receptors compared to RPARPAR. 7. tLyP-1-NW Extravasate into Regions Positive for NRP1 and NRP2

To assess tLyP-1-NW tumor penetration over time, tumor sections were analyzed after different circulation times, and blood vessels were stained with an anti-CD31 antibody. After 30 minutes of circulation, tLyP-1-NW fluorescence co-localized to a high extent with the CD31 staining, showing that the NWs were mainly inside the blood vessels or associated with the blood vessel walls. After 4 hours, most of the NWs had extravasated and penetrated the tumor tissue, with only a small fraction still associated with the blood vessels. Similar extravasation pattern was also observed in MDA-MB-231 breast cancer xenografts. The NWs were allowed to circulate for 30 min or 4 h. Blood vessels were stained with an anti-CD31 antibody. Extravasation in the tumor parenchyma increased over time.

tLyP-1-NWs were present in tumor regions where NRP1 and NRP2 were abundantly expressed, and co-localization with anti-NRP1 and anti-NRP2 immunostaining was observed. tLyP-1-NWs were still seen in the tumor after overnight circulation, whereas the non-specific accumulation in the liver, spleen and kidney was no longer detectable. At this time point, the tLyP-1-NW signal no longer co-localized with tumor blood vessels and spread wider in the tumor tissue. These results show that tLyP-1 is a specific tumor-homing peptide, with higher penetration capacities than LyP-1.

The ability of tLyP-1 to trigger tumor penetration of a co-administered compound by activating the CendR pathway was also tested. tLyP-1 peptide was injected together with a tumor-homing peptide (CGKRK; SEQ ID NO:1) that is unable to get out of blood vessels by itself (Hoffmann et al., 2003; Agenmy et al., 2011). Confocal microscopy analyses revealed enhanced tumor penetration of CGKRK (CGKRK; SEQ ID NO:1) when injected with tLyP-1. Thus, tLyP-1 can also induce penetration of a co-administered compound.

Throughout this application, various publications are referenced. The disclosures of these publications in their entireties are hereby incorporated by reference into this application in order to more fully describe the state of the art to which this invention pertains.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. An isolated peptide, wherein the C-terminal end of the peptide consists of the amino acid sequence CGNKRTR (SEQ ID NO:4).

2. An activatable peptide comprising a tLyP-1 peptide and a blocking group, wherein the tLyP-1 peptide comprises the amino acid sequence CGNKRTR (SEQ ID NO:4) at the C-terminal end of the tLyP-1 peptide, wherein the C-terminal end of the tLyP-1 peptide is blocked by the blocking group, wherein the blocking group is coupled to the terminal carboxy group of the tLyP-1 peptide, wherein the blocking group can be removed in vivo to expose the terminal carboxy group of the tLyP-1 peptide, wherein the activatable peptide is not displayed by a phage display phage, wherein the activatable peptide does not comprise the amino acid sequence CGNKRTRGC (SEQ ID NO:10).

3. The activatable peptide of claim 2, wherein the bond coupling the blocking group and the terminal carboxyl group is cleavable by a cleaving agent, wherein following cleavage, the terminal carboxy group of the C-terminal end of the tLyP-1 peptide is unblocked.

4. The activatable peptide of claim 2, wherein the blocking group does not consist of two amino acids or the blocking group is an amino acid linker when the blocking group comprises an amino acid.

5. A composition comprising the activatable peptide of claim 2 and a carrier, vehicle, or both.

6. The composition of claim 5 further comprising a co-composition, wherein the activatable peptide and the co-composition are not covalently coupled to each other and are not non-covalently associated with each other, wherein the activatable peptide and the co-composition being not non-covalently associated with each other means that no atom covalently coupled to the activatable peptide is involved in a non-covalent bond with an atom covalently coupled to the co-composition.

7. The composition of claim 5, wherein the activatable peptide selectively homes to a tumor.

8. The composition of claim 7, wherein the activatable peptide selectively homes to tumor vasculature.

9. The composition of claim 6, wherein the co-composition comprises a therapeutic agent.

10. The composition of claim 6, wherein the co-composition comprises a detection agent.

11. The composition of claim 6, wherein the co-composition comprises a carrier, vehicle, or both.

12. The composition of claim 6, wherein the co-composition comprises a surface molecule, one or more homing molecules, and a plurality of membrane perturbing molecules, wherein the homing molecules selectively home to tumor vasculature.

13. The composition of claim 12, wherein one or more of the homing molecules comprise the amino acid sequence CGKRK (SEQ ID NO:1) or the amino acid sequence CRKDKC (SEQ ID NO:2).

14. The composition of claim 12, wherein one or more of the homing molecules comprise the amino acid sequence CGKRK (SEQ ID NO:1).

15. The composition of claim 12, wherein one or more of the membrane perturbing molecules comprise the amino acid sequence $_D$(KLAKLAK)$_2$ (SEQ ID NO:3), (KLAKLAK)$_2$ (SEQ ID NO:3), (KLAKKLA)$_2$ (SEQ ID NO:5), (KAAKKAA)$_2$ (SEQ ID NO:6), or (KLGKKLG)$_3$ (SEQ ID NO:7).

16. The composition of claim 12, wherein the surface molecule comprises a nanoparticle, a nanoworm, a liposome, a micelle, a phospholipid, a polymer, a microparticle, or a fluorocarbon microbubble.

17. The composition of claim 5 further comprising one or more moieties.

18. The composition of claim 17, wherein at least one of the moieties is a therapeutic agent.

19. The composition of claim 18, wherein the therapeutic agent is paclitaxel.

20. The composition of claim 17, wherein at least one of the moieties is a detectable agent.

21. The composition of claim 12, wherein one or more of the homing molecules comprise the amino acid sequence CGKRK (SEQ ID NO:1), wherein one or more of the membrane perturbing molecules comprise the amino acid sequence $_D$(KLAKLAK)$_2$ (SEQ ID NO:3), wherein one or more of the homing molecules are indirectly conjugated to the surface molecule via a linker, and wherein one or more of the membrane perturbing molecules are indirectly conjugated to the surface molecule via a linker.

22. The composition of claim 21, wherein at least one of the linkers comprises polyethylene glycol.

23. The composition of claim 16, wherein the nanoworm is an iron oxide nanoworm.

24. The composition of claim 16, wherein the nanoparticle is an iron oxide nanoparticle or an albumin nanoparticle.

25. A composition comprising an activatable peptide, a carrier, vehicle, or both, and a cargo composition,
  wherein the activatable peptide comprises a tLyP-1 peptide and a blocking group, wherein the tLyP-1 peptide comprises the amino acid sequence CGNKRTR (SEQ ID NO:4) at the C-terminal end of the tLyP-1 peptide, wherein the C-terminal end of the tLyP-1 peptide is blocked by the blocking group, wherein the blocking group is coupled to the terminal carboxy group of the tLyP-1 peptide, wherein the blocking group can be removed in vivo to expose the terminal carboxy group of the tLyP-1 peptide, wherein the activatable peptide is not displayed by a phage display phage, wherein the activatable peptide does not comprise the amino acid sequence CGNKRTRGC (SEQ ID NO:10), and wherein either:
  (a) the activatable peptide and the cargo composition are covalently coupled to each other; or
  (b) the activatable peptide and the cargo composition are non-covalently associated with each other.

26. The composition of claim 25, wherein the cargo composition comprises a surface molecule, one or more homing molecules, and a plurality of membrane perturbing molecules, wherein the homing molecules selectively home to tumor vasculature.

27. The compositon of claim 25, wherein the cargo composition comprises a therapeutic agent.

28. The compositon of claim 25, wherein the cargo composition comprises a detection agent.

29. The compositon of claim 25, wherein the cargo composition comprises a carrier, vehicle, or both.

30. An isolated peptide comprising the amino acid sequence CGNKRTR (SEQ ID NO:4) at the C-terminal end of the peptide, wherein the C-terminal end of the peptide is blocked by a blocking group coupled to the terminal carboxy group, wherein the blocking group does not comprise an amino acid, wherein the activatable peptide does not comprise the amino acid sequence CGNKRTRGC (SEQ ID NO:10).

31. An isolated peptide comprising the amino acid sequence CGNKRTR (SEQ ID NO:4) at the C-terminal end of the peptide, wherein the C-terminal end of the peptide is blocked by a blocking group coupled to the terminal arginine of SEQ ID NO:4, and wherein the blocking group does not comprise an amino acid.

32. The activatable peptide of claim 31, wherein the bond coupling the blocking group and the terminal arginine of SEQ ID NO:4 is cleavable by a cleaving agent, wherein following cleavage, the terminal arginine of SEQ ID NO:4 is unblocked.

33. A method of enhancing internalization, penetration, or both of a co-composition into or through a cell, tissue, or both, the method comprising:
    exposing the cell, tissue, or both to the co-composition and a tLyP-1 composition, thereby enhancing internalization, penetration, or both of the co-composition into or through the cell, tissue, or both,
    wherein the tLyP-1 composition comprises the peptide of claim 1 and a carrier, vehicle, or both, wherein, prior to exposing the cell, tissue, or both, the tLyP-1 composition and the co-composition are not covalently coupled to each other and are not non-covalently associated with each other, wherein the peptide and the co-composition being not non-covalently associated with each other means that no atom covalently coupled to the peptide is involved in a non-covalent bond with an atom covalently coupled to the co-composition.

34. The method of claim 33, wherein the cell, tissue, or both is in a subject.

35. The method of claim 34, wherein the cell, tissue, or both are exposed to the tLyP-1 composition and the co-composition by administering the tLyP-1 composition and the co-composition to the subject.

36. The method of claim 35, wherein the tLyP-1 composition and the co-composition are administered to the subject simultaneously.

37. The method of claim 36, wherein the tLyP-1 composition and the co-composition are administered to the subject in a single composition comprising the tLyP-1 composition and the co-composition.

38. The method of claim 35, wherein the tLyP-1 composition and the co-composition are administered to the subject in separate compositions.

39. The method of claim 35, wherein the tLyP-1 composition and the co-composition are administered to the subject at different times.

40. The method of claim 38, wherein the tLyP-1 composition and the co-composition are administered to the subject by separate routes.

41. The method of claim 33, wherein the tLyP-1 composition and the co-composition are not bound to each other.

42. A method of enhancing internalization, penetration, or both of a cargo composition into or through a cell, tissue, or both, the method comprising:
    exposing the cell, tissue, or both to the cargo composition and a tLyP-1 composition, thereby enhancing internalization, penetration, or both of the cargo composition into or through the cell, tissue, or both,
    wherein the tLyP-1 composition comprises the peptide of claim 1 and a carrier, vehicle, or both,
    wherein either:
    (a) the tLyP-1 composition and the cargo composition are covalently coupled to each other; or
    (b) the tLyP-1 composition and the cargo composition are non-covalently associated with each other.

43. The method of claim 42, wherein the cell, tissue, or both is in a subject.

44. The method of claim 43, wherein the cell, tissue, or both are exposed to the tLyP-1 composition and the cargo composition by administering the tLyP-1 compositon and the cargo composition to the subject.

45. A method of enhancing internalization, penetration, or both into or through a cell, tissue, or both, the method comprising:
    exposing the cell, tissue, or both to a tLyP-1 composition, thereby enhancing internalization, penetration, or both into or through the cell, tissue, or both,
    wherein the tLyP-1 composition comprises the peptide of claim 1 and a carrier, vehicle, or both.

46. A method of enhancing internalization, penetration, or both into or through a cell, tissue, or both, the method comprising:
    exposing the cell, tissue, or both to a tLyP-1 composition, thereby enhancing internalization, penetration, or both into or through the cell, tissue, or both, wherein the tLyP-1 composition comprises the composition of claim 5.

47. The method of claim 46, wherein the cell, tissue, or both is in a subject, wherein the cell, tissue, or both are exposed to the tLyP-1 composition by administering the tLyP-1 composition to the subject.

* * * * *

UNITED STATES PATENT AND TRADEMARK OFFICE
CERTIFICATE OF CORRECTION

PATENT NO. : 10,179,801 B2
APPLICATION NO. : 13/594194
DATED : January 15, 2019
INVENTOR(S) : Erkki Ruoslahti et al.

It is certified that error appears in the above-identified patent and that said Letters Patent is hereby corrected as shown below:

In the Claims

Claim 2, Column 183, Line 14, replace "phage display phage" with --phage display--.
Claim 25, Column 184, Line 39, replace "phage display phage" with --phage display--.
Claim 27, Column 184, Line 52, replace "compositon" with --composition--.
Claim 28, Column 184, Line 54, replace "compositon" with --composition--.
Claim 29, Column 184, Line 56, replace "compositon" with --composition--.
Claim 32, Column 185, Line 5, replace "activatable peptide" with --isolated peptide--.
Claim 44, Column 186, Line 23, replace "compositon" with --composition--.

Signed and Sealed this
Eighteenth Day of June, 2019

Andrei Iancu
*Director of the United States Patent and Trademark Office*

SEQUENCE LISTING

<160> NUMBER OF SEQ ID NOS: 200

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence

<400> SEQUENCE: 1

Cys Gly Lys Arg Lys
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic sequence

<400> SEQUENCE: 2

Cys Arg Lys Asp Lys Cys
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(14)
<223> OTHER INFORMATION: D-enantiomer

<400> SEQUENCE: 3

Lys Leu Ala Lys Leu Ala Lys Lys Leu Ala Lys Leu Ala Lys
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic sequence

<400> SEQUENCE: 4

Cys Gly Asn Lys Arg Thr Arg
1               5

<210> SEQ ID NO 5
<211> LENGTH: 14
<212> TYPE: PRT
<213> ORGANISM: Artificial Sequence
<220> FEATURE:
<223> OTHER INFORMATION: Synthetic sequence

<400> SEQUENCE: 5

Lys Leu Ala Lys Lys Leu Ala Lys Leu Ala Lys Lys Leu Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic sequence

```
<400> SEQUENCE: 6

Lys Ala Ala Lys Lys Ala Ala Lys Ala Ala Lys Lys Ala Ala
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Synthetic sequence

<400> SEQUENCE: 7

Lys Leu Gly Lys Lys Leu Gly Lys Leu Gly Lys Lys Leu Gly Lys Leu
1               5                   10                  15

Gly Lys Lys Leu Gly
            20

<210> SEQ ID NO 8
<211> LENGTH: 24
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (8)..(24)
<223> OTHER INFORMATION: Xaa can be any naturally occurring amino acid

<400> SEQUENCE: 8

Cys Gly Asn Lys Arg Thr Arg Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 9
<211> LENGTH: 7
<212> TYPE: PRT
<213> ORGANISM: Artificial Sequence
<220> FEATURE:
<223> OTHER INFORMATION: Synthetic sequence

<400> SEQUENCE: 9

Arg Pro Ala Arg Pro Ala Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic sequence

<400> SEQUENCE: 10

Cys Gly Asn Lys Arg Thr Arg Gly Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (5)..(5)
<223> OTHER INFORMATION: X = K or R
<220> FEATURE:
```

```
<221> NAME/KEY: SITE
<222> LOCATION: (8)..(8)
<223> OTHER INFORMATION: X = D or E

<400> SEQUENCE: 11

Cys Arg Gly Asp Xaa Gly Pro Xaa Cys
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic sequence

<400> SEQUENCE: 12

Cys Arg Glu Lys Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (7)..(7)
<223> OTHER INFORMATION: X = K or H

<400> SEQUENCE: 13

Cys Gly Asn Lys Arg Thr Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic sequence

<400> SEQUENCE: 14

Cys Gly Asn Lys Arg Thr Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic sequence

<400> SEQUENCE: 15

Cys Gly Asn Lys Arg Thr His
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic sequence

<400> SEQUENCE: 16

Cys Arg Ser Thr Arg Ala Asn Pro Cys
1               5
```

```
<210> SEQ ID NO 17
<211> LENGTH: 9
<212> TYPE: PRT
<213> ORGANISM: Artificial Sequence
<220> FEATURE:
<223> OTHER INFORMATION: Synthetic sequence

<400> SEQUENCE: 17

Cys Pro Lys Thr Arg Arg Val Pro Cys
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic sequence

<400> SEQUENCE: 18

Cys Gly Asn Lys Arg Thr Lys Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (7)..(7)
<223> OTHER INFORMATION: X = R or K or H

<400> SEQUENCE: 19

Cys Gly Asn Arg Arg Thr Xaa
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic sequence

<400> SEQUENCE: 20

Cys Lys Arg Ala Val Arg
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic sequence

<400> SEQUENCE: 21

Cys Arg Asn Ser Trp Lys Pro Asn Cys
1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic sequence

<400> SEQUENCE: 22

Arg Arg Arg Lys
```

```
<210> SEQ ID NO 23
<211> LENGTH: 5
<212> TYPE: PRT
<213> ORGANISM: Artificial Sequence
<220> FEATURE:
<223> OTHER INFORMATION: Synthetic sequence

<400> SEQUENCE: 23

Arg Gly Ser Ser Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic sequence

<400> SEQUENCE: 24

Asn Gly Arg Ala His Ala
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (7)..(7)
<223> OTHER INFORMATION: X  = R or K

<400> SEQUENCE: 25

Cys Gly Asn Arg Arg Thr Xaa
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (7)..(7)
<223> OTHER INFORMATION: X = R or H

<400> SEQUENCE: 26

Cys Gly Asn Arg Arg Thr Xaa
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (7)..(7)
<223> OTHER INFORMATION: X = K or H

<400> SEQUENCE: 27

Cys Gly Asn Arg Arg Thr Xaa
1               5
```

```
<210> SEQ ID NO 28
<211> LENGTH: 7
<212> TYPE: PRT
<213> ORGANISM: Artificial Sequence
<220> FEATURE:
<223> OTHER INFORMATION: Synthetic sequence

<400> SEQUENCE: 28

Cys Gly Asn Arg Arg Thr Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic sequence

<400> SEQUENCE: 29

Cys Gly Asn Arg Arg Thr Lys
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic sequence

<400> SEQUENCE: 30

Cys Gly Asn Arg Arg Thr His
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic sequence

<400> SEQUENCE: 31

Cys Gly Asn Arg Arg Thr Lys Gly
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (7)..(7)
<223> OTHER INFORMATION: X = R or K or H

<400> SEQUENCE: 32

Cys Gly Asn His Arg Thr Xaa
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (7)..(7)
```

```
<223> OTHER INFORMATION: X = R or K

<400> SEQUENCE: 33

Cys Gly Asn His Arg Thr Xaa
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (7)..(7)
<223> OTHER INFORMATION: X = R or H

<400> SEQUENCE: 34

Cys Gly Asn His Arg Thr Xaa
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (7)..(7)
<223> OTHER INFORMATION: X = K or H

<400> SEQUENCE: 35

Cys Gly Asn His Arg Thr Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic sequence

<400> SEQUENCE: 36

Cys Gly Asn His Arg Thr Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic sequence

<400> SEQUENCE: 37

Cys Gly Asn His Arg Thr Lys
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic sequence

<400> SEQUENCE: 38

Cys Gly Asn His Arg Thr His
1               5
```

```
<210> SEQ ID NO 39
<211> LENGTH: 8
<212> TYPE: PRT
<213> ORGANISM: Artificial Sequence
<220> FEATURE:
<223> OTHER INFORMATION: Synthetic sequence

<400> SEQUENCE: 39

Cys Gly Asn His Arg Thr Lys Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or K or H

<400> SEQUENCE: 40

Cys Gly Asn Xaa Arg Thr Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or K

<400> SEQUENCE: 41

Cys Gly Asn Xaa Arg Thr Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or H

<400> SEQUENCE: 42

Cys Gly Asn Xaa Arg Thr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = K or H

<400> SEQUENCE: 43
```

```
Cys Gly Asn Xaa Arg Thr Arg
1               5
```

<210> SEQ ID NO 44
<211> LENGTH: 7
<212> TYPE: PRT
<213> ORGANISM: Artificial Sequence
<220> FEATURE:
<223> OTHER INFORMATION: Synthetic sequence

<400> SEQUENCE: 44

```
Cys Gly Asn Arg Arg Thr Arg
1               5
```

<210> SEQ ID NO 45
<211> LENGTH: 9
<212> TYPE: PRT
<213> ORGANISM: Artificial Sequence
<220> FEATURE:
<223> OTHER INFORMATION: Synthetic sequence

<400> SEQUENCE: 45

```
Cys Ser Gly Met Ala Arg Thr Lys Cys
1               5
```

<210> SEQ ID NO 46
<211> LENGTH: 6
<212> TYPE: PRT
<213> ORGANISM: Artificial Sequence
<220> FEATURE:
<223> OTHER INFORMATION: Synthetic sequence

<400> SEQUENCE: 46

```
Cys Pro Lys Arg Pro Arg
1               5
```

<210> SEQ ID NO 47
<211> LENGTH: 10
<212> TYPE: PRT
<213> ORGANISM: Artificial Sequence
<220> FEATURE:
<223> OTHER INFORMATION: Synthetic sequence

<400> SEQUENCE: 47

```
Cys Gln Ser Cys Asn Gly Arg Cys Val Arg
1               5                   10
```

<210> SEQ ID NO 48
<211> LENGTH: 10
<212> TYPE: PRT
<213> ORGANISM: Artificial Sequence
<220> FEATURE:
<223> OTHER INFORMATION: Synthetic sequence

<400> SEQUENCE: 48

```
Cys Arg Thr Cys Asn Gly Arg Cys Gln Val
1               5                   10
```

<210> SEQ ID NO 49
<211> LENGTH: 10
<212> TYPE: PRT
<213> ORGANISM: Artificial Sequence
<220> FEATURE:
<223> OTHER INFORMATION: Synthetic sequence

<400> SEQUENCE: 49

```
Cys Val Gln Cys Asn Gly Arg Cys Ala Leu
```

```
<210> SEQ ID NO 50
<211> LENGTH: 10
<212> TYPE: PRT
<213> ORGANISM: Artificial Sequence
<220> FEATURE:
<223> OTHER INFORMATION: Synthetic sequence

<400> SEQUENCE: 50

Cys Arg Cys Cys Asn Gly Arg Cys Ser Pro
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic sequence

<400> SEQUENCE: 51

Cys Ala Ser Asn Asn Gly Arg Val Val Leu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic sequence

<400> SEQUENCE: 52

Cys Gly Arg Cys Asn Gly Arg Cys Leu Leu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic sequence

<400> SEQUENCE: 53

Cys Trp Leu Cys Asn Gly Arg Cys Gly Arg
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic sequence

<400> SEQUENCE: 54

Cys Ser Lys Cys Asn Gly Arg Cys Gly His
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic sequence

<400> SEQUENCE: 55

Cys Val Trp Cys Asn Gly Arg Cys Gly Leu
1               5                   10
```

```
<210> SEQ ID NO 56
<211> LENGTH: 10
<212> TYPE: PRT
<213> ORGANISM: Artificial Sequence
<220> FEATURE:
<223> OTHER INFORMATION: Synthetic sequence

<400> SEQUENCE: 56

Cys Ile Arg Cys Asn Gly Arg Cys Ser Val
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic sequence

<400> SEQUENCE: 57

Cys Gly Glu Cys Asn Gly Arg Cys Val Glu
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic sequence

<400> SEQUENCE: 58

Cys Glu Gly Val Asn Gly Arg Arg Leu Arg
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic sequence

<400> SEQUENCE: 59

Cys Leu Ser Cys Asn Gly Arg Cys Pro Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic sequence

<400> SEQUENCE: 60

Cys Glu Val Cys Asn Gly Arg Cys Ala Leu
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Synthetic sequence

<400> SEQUENCE: 61

Gly Gly Gly Val Phe Trp Gln
1               5
```

```
<210> SEQ ID NO 62
<211> LENGTH: 13
<212> TYPE: PRT
<213> ORGANISM: Artificial Sequence
<220> FEATURE:
<223> OTHER INFORMATION: Synthetic sequence

<400> SEQUENCE: 62

Cys Gly Arg Glu Cys Pro Arg Leu Cys Gln Ser Ser Cys
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetic sequence

<400> SEQUENCE: 63

Cys Asn Gly Arg Cys Val Ser Gly Cys Ala Gly Arg Cys
1               5                   10

<210> SEQ ID NO 64
<211> LENGTH: 8
<212> TYPE: PRT
<213> ORGANISM: Artificial Sequence
<220> FEATURE:
<223> OTHER INFORMATION: Synthetic sequence

<400> SEQUENCE: 64

Cys Leu Ser Gly Ser Leu Ser Cys
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic sequence

<400> SEQUENCE: 65

Cys Gly Ser Leu Val Arg Cys
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic sequence

<400> SEQUENCE: 66

Ala Leu Asn Gly Arg Glu Glu Ser Pro
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic sequence

<400> SEQUENCE: 67

Cys Val Leu Asn Gly Arg Met Glu Cys
1               5
```

```
<210> SEQ ID NO 68
<211> LENGTH: 5
<212> TYPE: PRT
<213> ORGANISM: Artificial Sequence
<220> FEATURE:
<223> OTHER INFORMATION: Synthetic sequence

<400> SEQUENCE: 68

Cys Asn Gly Arg Cys
1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic sequence

<400> SEQUENCE: 69

Cys Glu Met Cys Asn Gly Arg Cys Met Gly
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic sequence

<400> SEQUENCE: 70

Cys Pro Leu Cys Asn Gly Arg Cys Ala Leu
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic sequence

<400> SEQUENCE: 71

Cys Pro Thr Cys Asn Gly Arg Cys Val Arg
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic sequence

<400> SEQUENCE: 72

Cys Gly Val Cys Asn Gly Arg Cys Gly Leu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic sequence

<400> SEQUENCE: 73

Cys Glu Gln Cys Asn Gly Arg Cys Gly Gln
1               5                   10

<210> SEQ ID NO 74
```

```
<211> LENGTH: 10
<212> TYPE: PRT
<213> ORGANISM: Artificial Sequence
<220> FEATURE:
<223> OTHER INFORMATION: Synthetic sequence

<400> SEQUENCE: 74

Cys Arg Asn Cys Asn Gly Arg Cys Glu Gly
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic sequence

<400> SEQUENCE: 75

Cys Val Leu Cys Asn Gly Arg Cys Trp Ser
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic sequence

<400> SEQUENCE: 76

Cys Val Thr Cys Asn Gly Arg Cys Arg Val
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic sequence

<400> SEQUENCE: 77

Cys Thr Glu Cys Asn Gly Arg Cys Gln Leu
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic sequence

<400> SEQUENCE: 78

Cys Arg Thr Cys Asn Gly Arg Cys Leu Glu
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Synthetic sequence

<400> SEQUENCE: 79

Cys Glu Thr Cys Asn Gly Arg Cys Val Gly
1               5                   10

<210> SEQ ID NO 80
<211> LENGTH: 10
```

```
<212> TYPE: PRT
<213> ORGANISM: Artificial Sequence
<220> FEATURE:
<223> OTHER INFORMATION: Synthetic sequence

<400> SEQUENCE: 80

Cys Ala Val Cys Asn Gly Arg Cys Gly Phe
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic sequence

<400> SEQUENCE: 81

Cys Arg Asp Leu Asn Gly Arg Lys Val Met
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic sequence

<400> SEQUENCE: 82

Cys Ser Cys Cys Asn Gly Arg Cys Gly Asp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic sequence

<400> SEQUENCE: 83

Cys Trp Gly Cys Asn Gly Arg Cys Arg Met
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic sequence

<400> SEQUENCE: 84

Cys Pro Leu Cys Asn Gly Arg Cys Ala Arg
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic sequence

<400> SEQUENCE: 85

Cys Lys Ser Cys Asn Gly Arg Cys Leu Ala
1               5                   10

<210> SEQ ID NO 86
<211> LENGTH: 10
<212> TYPE: PRT
```

```
<213> ORGANISM: Artificial Sequence
<220> FEATURE:
<223> OTHER INFORMATION: Synthetic sequence

<400> SEQUENCE: 86

Cys Val Pro Cys Asn Gly Arg Cys His Glu
1               5                   10

<210> SEQ ID NO 87
<211> LENGTH: 8
<212> TYPE: PRT
<213> ORGANISM: Artificial Sequence
<220> FEATURE:
<223> OTHER INFORMATION: Synthetic sequence

<400> SEQUENCE: 87

Cys Val Leu Asn Gly Arg Met Glu
1               5

<210> SEQ ID NO 88
<211> LENGTH: 10
<212> TYPE: PRT
<213> ORGANISM: Artificial Sequence
<220> FEATURE:
<223> OTHER INFORMATION: Synthetic sequence

<400> SEQUENCE: 88

Cys Lys Val Cys Asn Gly Arg Cys Cys Gly
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 89

Xaa Xaa Cys Asn Gly Arg Cys Xaa Xaa
1               5

<210> SEQ ID NO 90
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: SITE
<222> LOCATION: (4)..(4)
<223> OTHER INFORMATION: X = C or any amino acid
<220> FEATURE:
<221> NAME/KEY: SITE
<222> LOCATION: (8)..(8)
<223> OTHER INFORMATION: X = C or any amino acid
<220> FEATURE:
<221> NAME/KEY: misc_feature
<222> LOCATION: (9)..(10)
<223> OTHER INFORMATION: Xaa can be any naturally occurring amino acid
```

```
<400> SEQUENCE: 90

Cys Xaa Xaa Xaa Asn Gly Arg Xaa Xaa Xaa Cys
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (6)..(11)
<223> OTHER INFORMATION: Xaa can be any naturally occurring amino acid

<400> SEQUENCE: 91

Cys Asn Gly Arg Cys Xaa Xaa Xaa Xaa Xaa Xaa
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or K or H

<400> SEQUENCE: 92

Cys Gly Asn Xaa Arg Thr Lys
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or K

<400> SEQUENCE: 93

Cys Gly Asn Xaa Arg Thr Lys
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R ro H

<400> SEQUENCE: 94

Cys Gly Asn Xaa Arg Thr Lys
1               5

<210> SEQ ID NO 95
<211> LENGTH: 7
<212> TYPE: PRT
<213> ORGANISM: Artificial Sequence
```

```
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = K or H

<400> SEQUENCE: 95

Cys Gly Asn Xaa Arg Thr Lys
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or K

<400> SEQUENCE: 96

Cys Gly Asn Xaa His Arg Thr His
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or K

<400> SEQUENCE: 97

Cys Gly Asn Xaa Arg Thr His
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or H

<400> SEQUENCE: 98

Cys Gly Asn Xaa Arg Thr His
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = K or H

<400> SEQUENCE: 99

Cys Gly Asn Xaa Arg Thr His
1               5
```

```
<210> SEQ ID NO 100
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or K or H

<400> SEQUENCE: 100

Cys Gly Asn Xaa Arg Thr Lys Gly
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or K

<400> SEQUENCE: 101

Cys Gly Asn Xaa Arg Thr Lys Gly
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = R or H

<400> SEQUENCE: 102

Cys Gly Asn Xaa Arg Thr Lys Gly
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: (4)..(4)
<223> OTHER INFORMATION: X = K or H

<400> SEQUENCE: 103

Cys Gly Asn Xaa Arg Thr Lys Gly
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic sequence

<400> SEQUENCE: 104
```

```
Gly Gly Gly Gly Gly Gly Gly
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic sequence

<400> SEQUENCE: 105

Gly Gly Gly Arg Gly Gly Gly
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic sequence

<400> SEQUENCE: 106

Gly Gly Gly Gly Arg Gly Gly
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic sequence

<400> SEQUENCE: 107

His Gly Arg Val Arg Pro His
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic sequence

<400> SEQUENCE: 108

Cys Ser Arg Pro Arg Arg Ser Glu Cys
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic sequence

<400> SEQUENCE: 109

Cys Ser Arg Pro Arg Arg Ser Val Cys
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic sequence

<400> SEQUENCE: 110

Cys Ser Arg Pro Arg Arg Ser Trp Cys
```

```
1               5

<210> SEQ ID NO 111
<211> LENGTH: 31
<212> TYPE: PRT
<213> ORGANISM: Artificial Sequence
<220> FEATURE:
<223> OTHER INFORMATION: Synthetic sequence

<400> SEQUENCE: 111

Lys Asp Glu Pro Gln Arg Arg Ser Ala Arg Leu Ser Ala Lys Pro Ala
1               5                   10                  15

Pro Pro Lys Pro Glu Pro Lys Pro Lys Ala Pro Ala Lys Lys
            20                  25                  30

<210> SEQ ID NO 112
<211> LENGTH: 10
<212> TYPE: PRT
<213> ORGANISM: Artificial Sequence
<220> FEATURE:
<223> OTHER INFORMATION: Synthetic sequence

<400> SEQUENCE: 112

Pro Gln Arg Arg Ser Ala Arg Leu Ser Ala
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic sequence

<400> SEQUENCE: 113

Pro Lys Arg Arg Ser Ala Arg Leu Ser Ala
1               5                   10

<210> SEQ ID NO 114
<211> LENGTH: 9
<212> TYPE: PRT
<213> ORGANISM: Artificial Sequence
<220> FEATURE:
<223> OTHER INFORMATION: Synthetic sequence

<400> SEQUENCE: 114

Cys Asn Ser Arg Leu His Leu Arg Cys
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic sequence

<400> SEQUENCE: 115

Cys Glu Asn Trp Trp Gly Asp Val Cys
1               5

<210> SEQ ID NO 116
<211> LENGTH: 21
<212> TYPE: PRT
<213> ORGANISM: Artificial Sequence
<220> FEATURE:
<223> OTHER INFORMATION: Synthetic sequence

<400> SEQUENCE: 116
```

Trp Arg Cys Val Leu Arg Glu Gly Pro Ala Gly Gly Cys Ala Trp Phe
1               5                   10                  15

Asn Arg His Arg Leu
            20

<210> SEQ ID NO 117
<211> LENGTH: 9
<212> TYPE: PRT
<213> ORGANISM: Artificial Sequence
<220> FEATURE:
<223> OTHER INFORMATION: Synthetic sequence

<400> SEQUENCE: 117

Cys Leu Ser Ser Arg Leu Asp Ala Cys
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic sequence

<400> SEQUENCE: 118

Cys Val Leu Arg Gly Gly Arg Cys
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic sequence

<400> SEQUENCE: 119

Cys Asn Ser Arg Leu Gln Leu Arg Cys
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic sequence

<400> SEQUENCE: 120

Cys Gly Val Arg Leu Gly Cys
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic sequence

<400> SEQUENCE: 121

Cys Lys Asp Trp Gly Arg Ile Cys
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic sequence

```
<400> SEQUENCE: 122

Cys Leu Asp Trp Gly Arg Ile Cys
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic sequence

<400> SEQUENCE: 123

Cys Thr Arg Ile Thr Glu Ser Cys
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic sequence

<400> SEQUENCE: 124

Cys Glu Thr Leu Pro Ala Cys
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic sequence

<400> SEQUENCE: 125

Cys Arg Thr Gly Thr Leu Phe Cys
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic sequence

<400> SEQUENCE: 126

Cys Gly Arg Ser Leu Asp Ala Cys
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic sequence

<400> SEQUENCE: 127

Cys Arg His Trp Phe Asp Val Val Cys
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic sequence
```

```
<400> SEQUENCE: 128

Cys Ala Asn Ala Gln Ser His Cys
1               5

<210> SEQ ID NO 129
<211> LENGTH: 8
<212> TYPE: PRT
<213> ORGANISM: Artificial Sequence
<220> FEATURE:
<223> OTHER INFORMATION: Synthetic sequence

<400> SEQUENCE: 129

Cys Gly Asn Pro Ser Tyr Arg Cys
1               5

<210> SEQ ID NO 130
<211> LENGTH: 20
<212> TYPE: PRT
<213> ORGANISM: Artificial Sequence
<220> FEATURE:
<223> OTHER INFORMATION: Synthetic sequence

<400> SEQUENCE: 130

Tyr Pro Cys Gly Gly Glu Ala Val Ala Gly Val Ser Ser Val Arg Thr
1               5                   10                  15

Met Cys Ser Glu
            20

<210> SEQ ID NO 131
<211> LENGTH: 20
<212> TYPE: PRT
<213> ORGANISM: Artificial Sequence
<220> FEATURE:
<223> OTHER INFORMATION: Synthetic sequence

<400> SEQUENCE: 131

Leu Asn Cys Asp Tyr Gln Gly Thr Asn Pro Ala Thr Ser Val Ser Val
1               5                   10                  15

Pro Cys Thr Val
            20

<210> SEQ ID NO 132
<211> LENGTH: 7
<212> TYPE: PRT
<213> ORGANISM: Artificial Sequence
<220> FEATURE:
<223> OTHER INFORMATION: Synthetic sequence

<400> SEQUENCE: 132

Cys Leu Pro Val Ala Ser Cys
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic sequence

<400> SEQUENCE: 133

Cys Gly Ala Arg Glu Met Cys
1               5

<210> SEQ ID NO 134
<211> LENGTH: 8
```

```
<212> TYPE: PRT
<213> ORGANISM: Artificial Sequence
<220> FEATURE:
<223> OTHER INFORMATION: Synthetic sequence

<400> SEQUENCE: 134

Cys Lys Gly Arg Ser Ser Ala Cys
1               5

<210> SEQ ID NO 135
<211> LENGTH: 8
<212> TYPE: PRT
<213> ORGANISM: Artificial Sequence
<220> FEATURE:
<223> OTHER INFORMATION: Synthetic sequence

<400> SEQUENCE: 135

Cys Trp Ala Arg Ala Gln Gly Cys
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic sequence

<400> SEQUENCE: 136

Cys Leu Gly Arg Ser Ser Val Cys
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic sequence

<400> SEQUENCE: 137

Cys Thr Ser Pro Gly Gly Ser Cys
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic sequence

<400> SEQUENCE: 138

Cys Met Gly Arg Trp Arg Leu Cys
1               5

<210> SEQ ID NO 139
<211> LENGTH: 8
<212> TYPE: PRT
<213> ORGANISM: Artificial Sequence
<220> FEATURE:
<223> OTHER INFORMATION: Synthetic sequence

<400> SEQUENCE: 139

Cys Val Gly Glu Cys Gly Gly Cys
1               5

<210> SEQ ID NO 140
<211> LENGTH: 7
<212> TYPE: PRT
```

```
<213> ORGANISM: Artificial Sequence
<220> FEATURE:
<223> OTHER INFORMATION: Synthetic sequence

<400> SEQUENCE: 140

Cys Val Ala Trp Leu Asn Cys
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic sequence

<400> SEQUENCE: 141

Cys Arg Arg Phe Gln Asp Cys
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic sequence

<400> SEQUENCE: 142

Cys Leu Met Gly Val His Cys
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic sequence

<400> SEQUENCE: 143

Cys Lys Leu Leu Ser Gly Val Cys
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic sequence

<400> SEQUENCE: 144

Cys Phe Val Gly His Asp Leu Cys
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic sequence

<400> SEQUENCE: 145

Cys Arg Cys Leu Asn Val Cys
1               5

<210> SEQ ID NO 146
<211> LENGTH: 7
<212> TYPE: PRT
<213> ORGANISM: Artificial Sequence
```

```
<220> FEATURE:
<223> OTHER INFORMATION: Synthetic sequence

<400> SEQUENCE: 146

Cys Lys Leu Met Gly Glu Cys
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic sequence

<400> SEQUENCE: 147

Cys Ala Arg Ser Lys Asn Lys Asp Cys
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic sequence

<400> SEQUENCE: 148

Val Val Leu Val Thr Ser Ser
1               5

<210> SEQ ID NO 149
<211> LENGTH: 13
<212> TYPE: PRT
<213> ORGANISM: Artificial Sequence
<220> FEATURE:
<223> OTHER INFORMATION: Synthetic sequence

<400> SEQUENCE: 149

Cys Val Ala Leu Cys Arg Glu Ala Cys Gly Glu Gly Cys
1               5                   10

<210> SEQ ID NO 150
<211> LENGTH: 13
<212> TYPE: PRT
<213> ORGANISM: Artificial Sequence
<220> FEATURE:
<223> OTHER INFORMATION: Synthetic sequence

<400> SEQUENCE: 150

Cys Ser Ser Gly Cys Ser Lys Asn Cys Leu Glu Met Cys
1               5                   10

<210> SEQ ID NO 151
<211> LENGTH: 8
<212> TYPE: PRT
<213> ORGANISM: Artificial Sequence
<220> FEATURE:
<223> OTHER INFORMATION: Synthetic sequence

<400> SEQUENCE: 151

Cys Ile Gly Glu Val Glu Val Cys
1               5

<210> SEQ ID NO 152
<211> LENGTH: 9
<212> TYPE: PRT
<213> ORGANISM: Artificial Sequence
<220> FEATURE:
```

```
<223> OTHER INFORMATION: Synthetic sequence

<400> SEQUENCE: 152

Cys Lys Trp Ser Arg Leu His Ser Cys
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic sequence

<400> SEQUENCE: 153

Cys Trp Arg Gly Asp Arg Lys Ile Cys
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic sequence

<400> SEQUENCE: 154

Cys Glu Arg Val Val Gly Ser Ser Cys
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic sequence

<400> SEQUENCE: 155

Cys Leu Ala Lys Glu Asn Val Val Cys
1               5

<210> SEQ ID NO 156
<211> LENGTH: 13
<212> TYPE: PRT
<213> ORGANISM: Artificial Sequence
<220> FEATURE:
<223> OTHER INFORMATION: Synthetic sequence

<400> SEQUENCE: 156

Cys Gly Phe Glu Cys Val Arg Gln Cys Pro Glu Arg Cys
1               5                   10

<210> SEQ ID NO 157
<211> LENGTH: 8
<212> TYPE: PRT
<213> ORGANISM: Artificial Sequence
<220> FEATURE:
<223> OTHER INFORMATION: Synthetic sequence

<400> SEQUENCE: 157

Cys Gly Phe Glu Leu Glu Thr Cys
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic sequence
```

```
<400> SEQUENCE: 158

Cys Thr Leu Arg Asp Arg Asn Cys
1               5

<210> SEQ ID NO 159
<211> LENGTH: 8
<212> TYPE: PRT
<213> ORGANISM: Artificial Sequence
<220> FEATURE:
<223> OTHER INFORMATION: Synthetic sequence

<400> SEQUENCE: 159

Cys Leu His Arg Gly Asn Ser Cys
1               5

<210> SEQ ID NO 160
<211> LENGTH: 12
<212> TYPE: PRT
<213> ORGANISM: Artificial Sequence
<220> FEATURE:
<223> OTHER INFORMATION: Synthetic sequence

<400> SEQUENCE: 160

Cys Arg Ser Trp Asn Lys Ala Asp Asn Arg Ser Cys
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Synthetic sequence

<400> SEQUENCE: 161

Cys Gly Lys Arg Tyr Arg Asn Cys
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic sequence

<400> SEQUENCE: 162

Cys Leu Arg Pro Tyr Leu Asn Cys
1               5

<210> SEQ ID NO 163
<211> LENGTH: 12
<212> TYPE: PRT
<213> ORGANISM: Artificial Sequence
<220> FEATURE:
<223> OTHER INFORMATION: Synthetic sequence

<400> SEQUENCE: 163

Cys Thr Val Asn Glu Ala Tyr Lys Thr Arg Met Cys
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Synthetic sequence
```

```
<400> SEQUENCE: 164

Cys Arg Leu Arg Ser Tyr Gly Thr Leu Ser Leu Cys
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic sequence

<400> SEQUENCE: 165

Cys Arg Pro Trp His Asn Gln Ala His Thr Glu Cys
1               5                   10

<210> SEQ ID NO 166
<211> LENGTH: 9
<212> TYPE: PRT
<213> ORGANISM: Artificial Sequence
<220> FEATURE:
<223> OTHER INFORMATION: Synthetic sequence

<400> SEQUENCE: 166

Ser Trp Cys Glu Pro Gly Trp Cys Arg
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic sequence

<400> SEQUENCE: 167

Cys Lys Ala Ala Lys Asn Lys
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic sequence

<400> SEQUENCE: 168

Cys Lys Gly Ala Lys Ala Arg
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic sequence

<400> SEQUENCE: 169

Val Gly Val Gly Glu Trp Ser Val
1               5

<210> SEQ ID NO 170
<211> LENGTH: 7
<212> TYPE: PRT
<213> ORGANISM: Artificial Sequence
<220> FEATURE:
<223> OTHER INFORMATION: Synthetic sequence

<400> SEQUENCE: 170
```

Tyr Ser Gly Lys Trp Gly Trp
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic sequence

<400> SEQUENCE: 171

Gly Leu Ser Gly Gly Arg Ser
1               5

<210> SEQ ID NO 172
<211> LENGTH: 7
<212> TYPE: PRT
<213> ORGANISM: Artificial Sequence
<220> FEATURE:
<223> OTHER INFORMATION: Synthetic sequence

<400> SEQUENCE: 172

Leu Met Leu Pro Arg Ala Asp
1               5

<210> SEQ ID NO 173
<211> LENGTH: 7
<212> TYPE: PRT
<213> ORGANISM: Artificial Sequence
<220> FEATURE:
<223> OTHER INFORMATION: Synthetic sequence

<400> SEQUENCE: 173

Leu Pro Arg Tyr Leu Leu Ser
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic sequence

<400> SEQUENCE: 174

Cys Ser Cys Phe Arg Asp Val Cys Cys
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic sequence

<400> SEQUENCE: 175

Cys Arg Asp Val Val Ser Val Ile Cys
1               5

<210> SEQ ID NO 176
<211> LENGTH: 7
<212> TYPE: PRT
<213> ORGANISM: Artificial Sequence
<220> FEATURE:
<223> OTHER INFORMATION: Synthetic sequence

<400> SEQUENCE: 176

Tyr Ser Gly Lys Trp Gly Lys
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic sequence

<400> SEQUENCE: 177

Gly Ile Ser Ala Leu Val Leu Ser
1               5

<210> SEQ ID NO 178
<211> LENGTH: 7
<212> TYPE: PRT
<213> ORGANISM: Artificial Sequence
<220> FEATURE:
<223> OTHER INFORMATION: Synthetic sequence

<400> SEQUENCE: 178

Ser Arg Arg Gln Pro Leu Ser
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic sequence

<400> SEQUENCE: 179

Met Ser Pro Gln Leu Ala Thr
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic sequence

<400> SEQUENCE: 180

Met Arg Arg Asp Glu Gln Arg
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic sequence

<400> SEQUENCE: 181

Gln Val Arg Arg Val Pro Glu
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic sequence

<400> SEQUENCE: 182

Val Arg Arg Gly Ser Pro Gln

```
1               5
```

<210> SEQ ID NO 183
<211> LENGTH: 7
<212> TYPE: PRT
<213> ORGANISM: Artificial Sequence
<220> FEATURE:
<223> OTHER INFORMATION: Synthetic sequence

<400> SEQUENCE: 183

```
Gly Gly Arg Gly Ser Trp Glu
1               5
```

<210> SEQ ID NO 184
<211> LENGTH: 7
<212> TYPE: PRT
<213> ORGANISM: Artificial Sequence
<220> FEATURE:
<223> OTHER INFORMATION: Synthetic sequence

<400> SEQUENCE: 184

```
Phe Arg Val Arg Gly Ser Pro
1               5
```

<210> SEQ ID NO 185
<211> LENGTH: 7
<212> TYPE: PRT
<213> ORGANISM: Artificial Sequence
<220> FEATURE:
<223> OTHER INFORMATION: Synthetic sequence

<400> SEQUENCE: 185

```
Phe Arg Val Arg Gly Ser Pro
1               5
```

<210> SEQ ID NO 186
<211> LENGTH: 7
<212> TYPE: PRT
<213> ORGANISM: Artificial Sequence
<220> FEATURE:
<223> OTHER INFORMATION: Synthetic sequence

<400> SEQUENCE: 186

```
Val Lys Ser Val Cys Arg Thr
1               5
```

<210> SEQ ID NO 187
<211> LENGTH: 7
<212> TYPE: PRT
<213> ORGANISM: Artificial Sequence
<220> FEATURE:
<223> OTHER INFORMATION: Synthetic sequence

<400> SEQUENCE: 187

```
Trp Arg Gln Asn Met Pro Leu
1               5
```

<210> SEQ ID NO 188
<211> LENGTH: 7
<212> TYPE: PRT
<213> ORGANISM: Artificial Sequence
<220> FEATURE:
<223> OTHER INFORMATION: Synthetic sequence

<400> SEQUENCE: 188

```
Ser Arg Arg Phe Val Gly Gly
1               5
```

<210> SEQ ID NO 189
<211> LENGTH: 7
<212> TYPE: PRT
<213> ORGANISM: Artificial Sequence
<220> FEATURE:
<223> OTHER INFORMATION: Synthetic sequence

<400> SEQUENCE: 189

Ala Leu Glu Arg Arg Ser Leu
1               5

<210> SEQ ID NO 190
<211> LENGTH: 7
<212> TYPE: PRT
<213> ORGANISM: Artificial Sequence
<220> FEATURE:
<223> OTHER INFORMATION: Synthetic sequence

<400> SEQUENCE: 190

Ala Arg Arg Gly Trp Thr Leu
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic sequence

<400> SEQUENCE: 191

Ser Met Ser Ile Ala Arg Leu
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic sequence

<400> SEQUENCE: 192

Val Ser Phe Leu Glu Tyr Arg
1               5

<210> SEQ ID NO 193
<211> LENGTH: 7
<212> TYPE: PRT
<213> ORGANISM: Artificial Sequence
<220> FEATURE:
<223> OTHER INFORMATION: Synthetic sequence

<400> SEQUENCE: 193

Arg Gly Arg Trp Leu Ala Leu
1               5

<210> SEQ ID NO 194
<211> LENGTH: 7
<212> TYPE: PRT
<213> ORGANISM: Artificial Sequence
<220> FEATURE:
<223> OTHER INFORMATION: Synthetic sequence

<400> SEQUENCE: 194

Glu Val Arg Ser Arg Leu Ser
1               5

```
<210> SEQ ID NO 195
<211> LENGTH: 7
<212> TYPE: PRT
<213> ORGANISM: Artificial Sequence
<220> FEATURE:
<223> OTHER INFORMATION: Synthetic sequence

<400> SEQUENCE: 195

Val Arg Ala Arg Leu Met Ser
1               5

<210> SEQ ID NO 196
<211> LENGTH: 7
<212> TYPE: PRT
<213> ORGANISM: Artificial Sequence
<220> FEATURE:
<223> OTHER INFORMATION: Synthetic sequence

<400> SEQUENCE: 196

Arg Val Gly Leu Val Ala Arg
1               5

<210> SEQ ID NO 197
<211> LENGTH: 7
<212> TYPE: PRT
<213> ORGANISM: Artificial Sequence
<220> FEATURE:
<223> OTHER INFORMATION: Synthetic sequence

<400> SEQUENCE: 197

Arg Val Arg Leu Val Asn Leu
1               5

<210> SEQ ID NO 198
<211> LENGTH: 5
<212> TYPE: PRT
<213> ORGANISM: Artificial Sequence
<220> FEATURE:
<223> OTHER INFORMATION: Synthetic sequence

<400> SEQUENCE: 198

Cys Arg Pro Pro Arg
1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic sequence

<400> SEQUENCE: 199

Cys Gly Arg Lys Ser Lys Thr Val Cys
1               5

<210> SEQ ID NO 200
<211> LENGTH: 6
<212> TYPE: PRT
<213> ORGANISM: Artificial Sequence
<220> FEATURE:
<223> OTHER INFORMATION: Synthetic sequence

<400> SEQUENCE: 200

Cys Ala Arg Pro Ala Arg
1               5
```